(12) United States Patent
Low et al.

(10) Patent No.: US 9,629,918 B2
(45) Date of Patent: Apr. 25, 2017

(54) FOLATE RECEPTOR ALPHA BINDING LIGANDS

(71) Applicant: PURDUE RESEARCH FOUNDATION, West Lafayette, IN (US)

(72) Inventors: Philip Stewart Low, West Lafayette, IN (US); Balasubramanian Vaitilingam, West Lafayette, IN (US); Venkatesh Chelvam, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/382,177

(22) PCT Filed: Feb. 28, 2013

(86) PCT No.: PCT/US2013/028277
§ 371 (c)(1),
(2) Date: Aug. 29, 2014

(87) PCT Pub. No.: WO2013/130776
PCT Pub. Date: Sep. 6, 2013

(65) Prior Publication Data
US 2015/0023874 A1    Jan. 22, 2015

Related U.S. Application Data

(60) Provisional application No. 61/605,113, filed on Feb. 29, 2012.

(51) Int. Cl.
| | | |
|---|---|---|
| A61K 47/48 | (2006.01) | |
| A61K 31/475 | (2006.01) | |
| A61K 38/06 | (2006.01) | |
| A61K 49/00 | (2006.01) | |
| A61K 51/04 | (2006.01) | |

(52) U.S. Cl.
CPC ...... *A61K 47/48061* (2013.01); *A61K 31/475* (2013.01); *A61K 38/06* (2013.01); *A61K 47/48107* (2013.01); *A61K 49/0052* (2013.01); *A61K 51/0459* (2013.01)

(58) Field of Classification Search
None
See application file for complete search history.

(56) References Cited

U.S. PATENT DOCUMENTS

| | | |
|---|---|---|
| 7,128,893 B2 | 10/2006 | Leamon et al. |
| 2001/0031252 A1 | 10/2001 | Low et al. |
| 2003/0086900 A1 | 5/2003 | Low et al. |
| 2004/0033195 A1 | 2/2004 | Leamon et al. |
| 2005/0002942 A1 | 1/2005 | Vlahov et al. |
| 2010/0323973 A1 | 12/2010 | Leamon et al. |

FOREIGN PATENT DOCUMENTS

| | | |
|---|---|---|
| EP | 1900752 A1 | 3/2008 |
| EP | 2258401 | 12/2010 |
| WO | WO02085908 | 10/2002 |
| WO | WO03097647 | 11/2003 |
| WO | WO2005080431 A2 | 9/2005 |
| WO | WO2006012527 | 2/2006 |
| WO | WO2007022493 A2 | 2/2007 |
| WO | WO2010033733 | 3/2010 |
| WO | WO2010033733 A1 | 4/2010 |
| WO | WO2010102238 A1 | 9/2010 |
| WO | WO2011069116 A1 | 6/2011 |

OTHER PUBLICATIONS

McMahon et al (2000).*
Pinedo et al (2000).*
PCT Search Report and Written Opinion for PCT/US2013/028277, completed Apr. 2, 2013.
Bhattacharya, D., et al. "Folate Receptor Targeted, Carboxymethyl Chitosan Functionalized Iron Oxide Nanoparticles: A Novel Ultradispersed Nanoconjugates for Bimodal Imaging", 2011, vol. 3, No. 4, pp: 1653-1662, abstract only.
Angela Coliva et al, "90Y Labeling of monoclonal antibody MOv18 and preclinical validation for radioimmunotherapy of human ovarian carcinomas", Cancer Immunology Immunotherapy (2005), vol. 54, No. 12, p. 1200-1213.
K. M. Maziarz et al, "Complete Mapping of Divergent Amino Acids Responsible for Differential Ligand Binding of Folate Receptors α and β ", Journal of Biological Chemistry, (1999), vol. 274, No. 16, p. 11086-11091.
Xin W et al, "Differential stereospecificities and affinities of folate receptor isoforms for folate compounds and antifolates", Biochemical Pharmacology, vol. 44, No. 9, (1992), p. 1898-1901.

* cited by examiner

*Primary Examiner* — Paul V Ward
(74) *Attorney, Agent, or Firm* — Barnes & Thornburg LLP

(57) ABSTRACT

The invention described herein pertains to targeted drug delivery conjugates comprising folate receptor α (FR-α) selective binding ligands and methods for diagnosing, monitoring, and eliminating pathological cells that express FR-α.

20 Claims, 19 Drawing Sheets

IC$_{50}$ of DMTHF-EC-119-TubH in IGROV Cell line

- ▲ DMTHF-EC-119-TubH a
- ■ COMPETITION b

FIG. 18

IC$_{50}$ of DMTHF-EC-119-DAVBH in IGROV Cell line

- ▲ DMTHF-EC-119-DAVBH a
- ■ COMPETITION b

FIG. 19

FOLATE RECEPTOR ALPHA BINDING LIGANDS

CROSS-REFERENCE TO RELATED APPLICATIONS

This application is a national stage entry under 35 USC§371(b) of International Application No. PTC / S2013/028277, filed Feb. 28, 2013, and claims the benefit, under 35 U.S.C.§119(e), of U.S. Provisional Application No. 61/605,113, filed Feb. 29, 2012, the disclosures of both of which are incorporated by reference here in their entirety.

TECHNICAL FIELD

The invention described herein pertains to targeted drug delivery conjugates comprising folate receptor α (FR-α) selective binding ligands and methods for diagnosing, monitoring, and eliminating pathological cells that express FR-α.

BACKGROUND AND SUMMARY OF THE INVENTION

Cancer is a leading cause of death in the United States, second only to heart disease, killing more than half a million Americans per year. Importantly, many of these cancer-related deaths are thought to be preventable if improved methods for early detection of the disease can be developed. One method of detection of the disease is imaging cancer cells or tumors by radiographraphy or photoluminescence (e.g. fluorescence). However, most methods for cancer tumor imaging either lack the sensitivity to detect early malignant loci or do not distinguish between tumor masses and sites of inflammation. For example, $^{18}$F-fluorodeoxyglucose ($^{18}$F-FDG) not only effectively images cancer, but also accumulates at sites of infection and immune-mediated inflammation, complicating the determination of whether an imaged mass derives from a tumor or inflamed tissue (e.g. rheumatoid arthritis, Crohn's disease, ulcerative colitis, asthma, and the like). Folate uptake by cancer cells and activated macrophages involves different isoforms of the same receptor (i.e. FR-α and FR-β, respectively). These two isoforms are only 76% homologous and structural differences between the two isoforms might allow selective binding. Consequently, there is a need for targeting ligands with increased selectivity for either FR-α or FR-β. Folate receptor binding ligands with increased selectivity for folate receptor-α have been discovered that are useful for preferential targeting of folate receptor ligand binding conjugates to cells expressing, over-expressing, or selectively expressing FR-α. Illustratively, an $N^5,N^{10}$-dimethylated derivative of tetrahydrofolic acid (DMTHF) displays increased selectivity for FR-α over FR-β. It has also been found that a $^{99m}$Tc chelate conjugate of DMTHF allows selective imaging of cancer tissue in animals containing both solid tumors and one of multiple types of inflammatory disease.

In one embodiment of the invention, a folate receptor alpha selective binding ligand drug conjugate of the formula

B-L-D or a pharmaceutically acceptable salt thereof, wherein
B is a folate receptor alpha selective binding ligand;
L is a linker or is absent; and
D represents one or more drugs independently selected from the group consisting of a diagnostic agent, a therapeutic agent, and a imaging agent is described.

In another embodiment, a pharmaceutical composition is described comprising an imaging effective or therapeutically effective amount of one or more of the folate receptor alpha selective binding ligand drug conjugates described herein.

In another embodiment, a method for imaging cancer cells in a patient is described, the method comprising administering an imaging effective amount of any one of the folate receptor alpha selective binding ligand drug conjugates described herein to the patient; and imaging the cancer cells.

In another embodiment, a method for treating a patient in need of relief from cancer is described, the method comprising the step of administering to the patient a therapeutically effective amount of any one or more of the folate receptor alpha selective binding ligand drug conjugates described herein.

BRIEF DESCRIPTION OF THE DRAWINGS

FIG. 8-1 Biodistribution studies of EC20-$^{99m}$Tc (hatched bars) and $^{99m}$Tc-DMTHF-chelate (solid bars) in C57BL/6J mice injected with cardiotoxin to develop muscle trauma (n=5).

FIG. 12-1 Flow cytometry analysis: (a) binding of DMTHF-DyLight™ 680 to FR-α positive KB cells; (b) binding of DMTHF-DyLight™ 680 to FR-β positive rat peritoneal macrophages; (c) binding of folate-DyLight™ 680 to FR-β positive rat peritoneal macrophages; (d) binding of folate-Oregon Green™ 488 to FR-β positive human peripheral blood monocytes, and (e) binding of DMTHF-Oregon Green™ 488 to FR-β positive human peripheral blood monocytes.

FIG. 12-2 Confocal fluorescence microscopy of KB cells incubated with $N^5,N^{10}$-dimethyl-tetrahydro-folate (DMTHF)-Dylight™ 680 conjugate or DMTHF-Dylight™ 680+100 fold excess folic acid for 1 h at 37° C. Cells were visualized at $\lambda_{em}$=700 nm; $\lambda_{ex}$=635 nm.

FIG. 14-1 Overlay of fluorescent image with white light image of Balb/C mice bearing M109 tumors and induced ulcerative colitis, 4 h after administration of folate-Dylight™ 680 (i) and DMTHF-Dylight™ 680 (ii) respectively. (a) Arrows=solid tumor xenografts, (b) Dorsal side imaging of the mice, (c) White light images of ROI of different tissues/organs and (d) Fluorescent image of ROI of different tissues/organs.

FIG. 14-2 Shows a comparison of uptake of folate-Dylight™ 680 and DMTHF-Dylight™ 680 in the colon of Balb/C mice bearing M109 tumors and induced ulcerative colitis, as in FIG. 14-1.

FIG. 18 Dose-dependent in vitro cytotoxicity study of DMTHF-EC-119-tubulysin B hydrazide ($IC_{50}$ is about 120 μM) in IGROV cells (a human ovarian cancer cell line). a) Triangles indicate treatment with an increasing concentration of drug conjugate DMTHF-EC-119-tubulysin B hydrazide; b) squares indicate treatment of IGROV cells pretreated with 100 μM folic acid for 1 h prior to addition of DMTHF-EC-119-tubulysin B hydrazide.

FIG. 19 Dose-dependent in vitro cytotoxicity study of DMTHF-EC-119-desacetylvinblastine hydrazide ($IC_{50}$ is about 1 μM) in IGROV cells (a human ovarian cancer cell line). a) Triangles indicate treatment with an increasing concentration of drug conjugate DMTHF-EC-119-desacetylvinblastine hydrazide; b) squares indicate treatment of IGROV cells pretreated with 100 μM folic acid for 1 h prior to addition of DMTHF-EC-119-desacetylvinblastine hydrazide.

DETAILED DESCRIPTION

Figure 1:
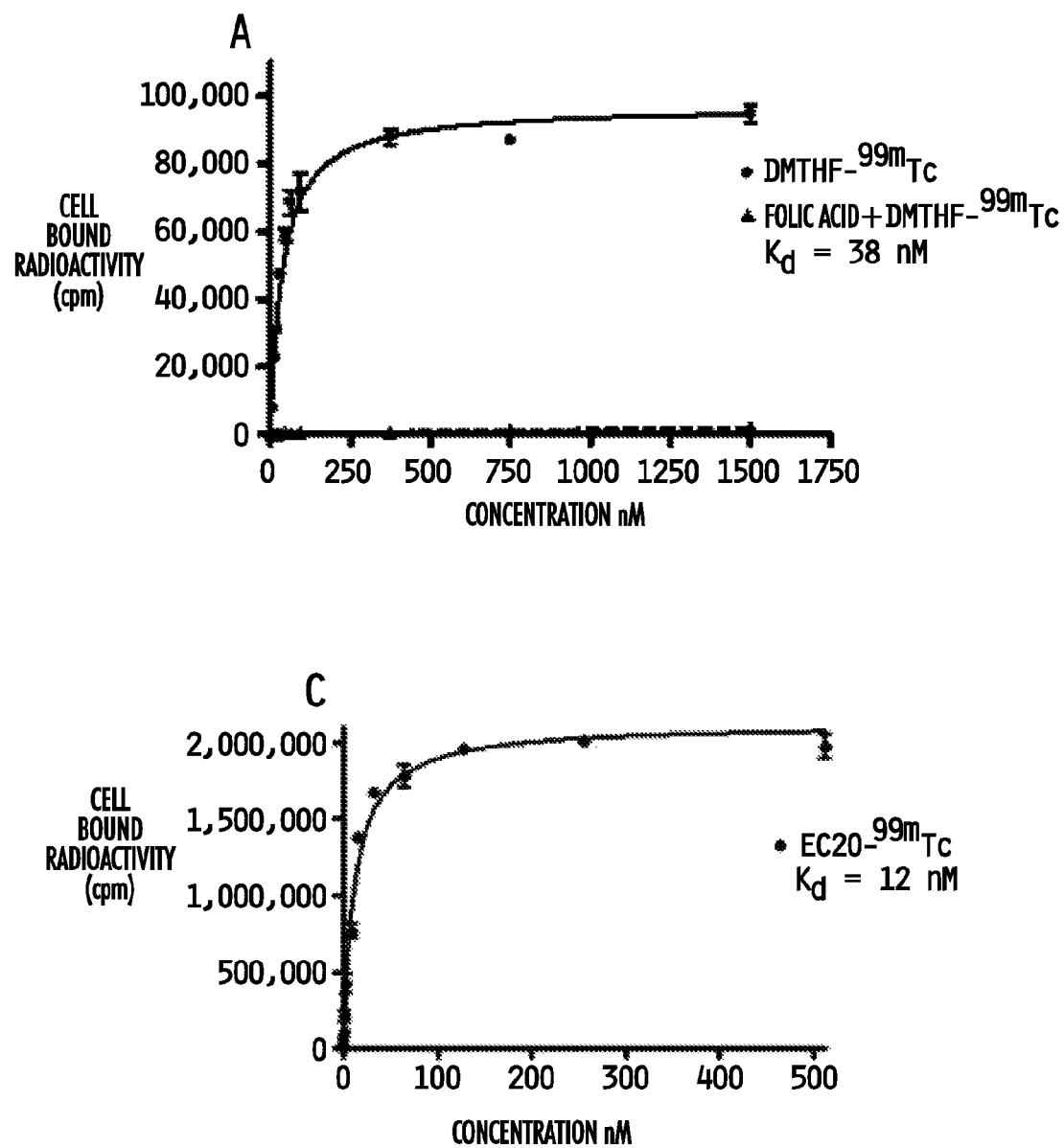
FIG. 1 Binding affinity of (A) DMTHF-$^{99m}$Tc for FR-α positive KB cells in culture in the absence (■) and presence (▲) of 100-fold excess free folic acid; error bars SD (n=3); (C) EC20-$^{99m}$Tc for FR-α positive KB cells - - - .

Unlike many other cancer imaging modalities, where selective imaging of malignant over inflamed tissues is intrinsically difficult (e.g. FDG-PET, $^{11}$C-choline, etc.), folate uptake by cancer cells and activated macrophages involves different isoforms of the same receptor (i.e. FR-α and FR-β, respectively). These two isoforms are only 76% homologous and structural differences between the two isoforms might allow selective binding of folate to one form over the other.

In one aspect, a folate receptor alpha (FR-α) selective binding ligand (B) is a ligand that binds to the FR-α with a Kd that is not more than 2.5-fold higher than the Kd for binding of folate to the FR-α and that binds to the folate receptor beta (FR-β) with a Kd that is at least 5-fold greater than the Kd for the binding of folate to the FR-β.

In another aspect, a FR-α selective binding ligand (B) is a ligand for which the ratio of its binding Kd for the FR-α to the binding Kd for folate binding to the FR-α ($Kd_\alpha$-B/$Kd_\alpha$-folate) is not more than about 2, 2.5, or 3; and for which the ratio of its binding Kd for the FR-β to the Kd for folate binding to the FR-β ($Kd_\beta$-B/$Kd_\beta$-folate) is at least about 3, 4, or 5.

In another aspect, a FR-α selective binding ligand (B) is a ligand that binds to the FR-α with a Kd that is at least 5-fold lower than the Kd for the binding of folate to the FR-α and that binds to the FR-β with a Kd that is at least equal to the Kd for the binding of folate to the FR-β.

In another aspect, a FR-α selective binding ligand (B) is a ligand for which the ratio of its binding Kd for the FR-α to the binding Kd for folate binding to the FR-α (Kd$_α$-B/Kd$_α$-folate) is less than from about 0.25 to about 0.1; and for which the ratio of its binding Kd for the FR-β to the Kd for folate binding to the FR-β (Kd$_β$-B/Kd$_β$-folate) is at least from about 1 to about 4.

It is understood that selective binding of the conjugates described herein to cells or tissues expressing, over-expressing, or selectively expressing FR-α relative to cells or tissues expressing, over-expressing, or selectively expressing FR-β may result from an increased affinity of the FR-α selective binding ligand drug conjugate for FR-α relative to binding of folate to FR-α or a decreased affinity for FR-β relative to binding of folate to FR-β, or a combination thereof.

As used herein the term "drug" includes imaging agents, diagnostic agents, and therapeutic agents.

Several embodiments of the invention are described by the following enumerated clauses:

1. A folate receptor alpha selective binding ligand drug conjugate of the formula

B-L-D or a hydrate, a solvate, a prodrug, a crystalline form, an amorphous form, or a pharmaceutically acceptable salt thereof, wherein B is a folate receptor alpha selective binding ligand;
L is a linker or is absent, wherein the linker is a chain of atoms selected from C, N, O, S, Si, and P; and
D represents one or more drugs independently selected from the group consisting of a diagnostic agent, a therapeutic agent, and a imaging agent.

2. The conjugate of clause 1 wherein the drug is a therapeutic agent.

3. The conjugate of clause 1 wherein the drug is an imaging agent.

4. The conjugate of clause 1 wherein the drug is a diagnostic agent.

5. The conjugate of any one of clauses 1 to 4 wherein B has the formula

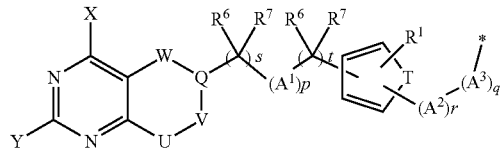

wherein * indicates the point of attachment to the linker;

X and Y are each-independently selected from the group consisting of halo, $R^2$, $OR^2$, $SR^3$, and $NR^4R^5$;

U, V, and W represent divalent moieties each independently selected from the group consisting of —($R^{6a}$)C═, —N═, —($R^{6a}$)C($R^{7a}$)—, and —N($R^{4a}$)—; Q is selected from the group consisting of C and CH; T is selected from the group consisting of S, O, $NR^{4b}$, and —HC═CH—;

$A^1$ and $A^2$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4b}$)S(O)$_2$—, —C($R^{6b}$)($R^{7b}$)—, —N(C≡CH)—, —N(CH$_2$C≡CH)—, $C_1$-$C_{12}$ alkylene, and $C_1$-$C_{12}$ alkyeneoxy, where Z is oxygen or sulfur;

$A^3$ is an amino acid; q is an integer from 0 to 3

$R^1$ is selected from the group consisting of hydrogen, halo, $C_1$-$C_{12}$ alkyl, and $C_1$-$C_{12}$ alkoxy; $R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group; $R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group; and p, r, s and t are each independently either 0 or 1.

5.1. The conjugate of any one of clauses 1 to 4 wherein B has the formula

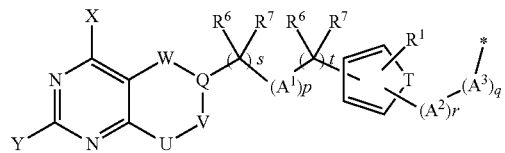

wherein * indicates the point of attachment to the linker;

X and Y are each-independently selected from the group consisting of halo, $R^1$, $OR^2$, $SR^3$, and $NR^4R^5$;

U, V, and W represent divalent moieties each independently selected from the group consisting of —($R^{6a}$)C($R^{7a}$)—, and —N($R^{4a}$)—; Q is CH; T is selected from the group consisting of S, O, $NR^{4b}$, and —HC═CH—;

$A^1$ and $A^2$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4b}$)S(O)$_2$—, —C($R^{6b}$)($R^{7b}$)—, —N(C≡CH)—, —N(CH$_2$C≡CH)—, $C_1$-$C_{12}$ alkylene, and $C_1$-$C_{12}$ alkyeneoxy, where Z is oxygen or sulfur;

$A^3$ is an amino acid; q is an integer from 0 to 3

$R^1$ is hydrogen or halo or is selected from the group consisting of, $C_1$-$C_{12}$ heteroalkyl, and $C_1$-$C_{12}$ alkoxy; $R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group; $R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group; and p, r, s and t are each independently either 0 or 1.

6. The conjugate of clause 5 or 5.1 wherein X is OH; and Y is NH$_2$.

7. The conjugate of clause 5, 5.1 or 6 wherein W and U are —N($R^{4a}$)—; Q is CH; V is CH$_2$; $A^1$ is —N($R^{4b}$)—; s is 1; p is 1; and t is 0.

7.1. The conjugate of any one of clauses 5 to 6 wherein W and U are —N($R^{4a}$)—; Q is CH; V is CH$_2$; $A^1$ is —N($R^{4b}$)—; s is 1; p is 1; and t is 0.

8. The conjugate of any one of clauses 5 to 7 wherein $R^{4a}$ and $R^{4b}$ are alkyl or heteroalkyl.

9. The conjugate of any one of clauses 5 to 8 wherein $R^{4a}$ and $R^{4b}$ are methyl.

10. The conjugate of any one of clauses 1 to 9 wherein the linker includes a releasable linker.

11. The conjugate of any one of clauses 1 to 9 wherein the linker does not include a releasable linker.

11.1. The conjugate of any one of clauses 1 to 11 wherein the linker comprises an amino acid selected from the group consisting of asparagine, aspartic acid, cysteine, glutamic acid, lysine, glutamine, arginine, serine, ornithine, and threonine.

12. The conjugate of any one of clauses 1, 3, or 5 to 11.1 wherein the drug is an imaging agent.

13. The conjugate of clause 12 wherein the imaging agent is a positron-emitting radioisotope attached to the linker selected from group consisting of $^{34}$Cl, $^{45}$Ti, $^{51}$Mn, $^{61}$Cu, $^{63}$Zn, $^{68}$Ga, $^{11}$C, $^{13}$N, $^{15}$O, and $^{18}$F.

14. The conjugate of clause 12 wherein the imaging agent is a radioactive isotope of a metal coordinated to a chelating group, where the radioactive metal isotope is selected from the group consisting of technetium, rhenium, gallium, gadolinium, indium, and copper.

15. The conjugate of clause 14 wherein the radioactive metal isotope is 111In, $^{99m}$Tc, $^{64}$Cu, $^{67}$Cu, $^{67}$Ga, or $^{68}$Ga.

16. The conjugate of clause 14 or 15 wherein the radioactive metal isotope is $^{99m}$Tc.

17. The conjugate of any one of clauses 14 to 16 wherein the chelating group has the formula

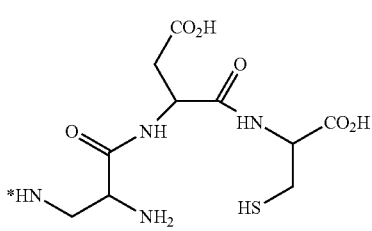

where * indicates that site of attachment of the linker L.

18. The conjugate of clause 12 wherein the imaging agent is a fluorescent dye.

19. The conjugate of clause 18 wherein the fluorescent dye has a formula selected from the group consisting of

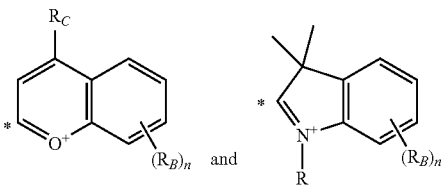

where X is oxygen, nitrogen, or sulfur, and where X is attached to linker L; Y is $OR^a$, $NR^a_2$, or $NR^a_3{}^+$; and Y' is O, $NR^a$, or $NR^a_2{}^+$; where each R is independently selected in each instance from hydrogen, fluoro, sulfonic acid, sulfonate, and salts thereof, and the like; and $R^a$ is hydrogen or alkyl;

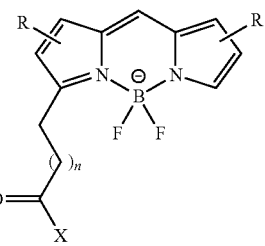

where X is oxygen, nitrogen, or sulfur, and where X is attached to linker L; and each R is independently selected in each instance from hydrogen, alkyl, heteroalkyl, and the like; and n is an integer from 0 to about 4; and

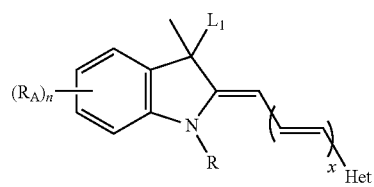

where Het is selected from the group consisting of

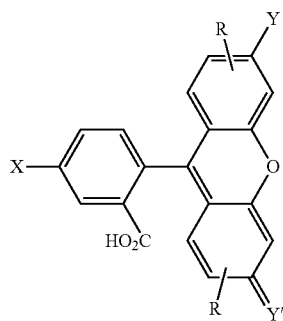

where * is the attachment point; $R_A$ and $R_B$ are independently selected in each instance from the group consisting of alkyl, heteroalkyl, sulfoalkyl, alkylsulfonic acid, alkylsulfonate, or a salt thereof, or an amine or a derivative thereof; $R_C$ is alkyl or heteroalkyl; $L_1$ is an alkylene attached to linker L; R is independently selected in each instance from alkyl, heteroalkyl, or alkylsulfonic acid, or alkylsulfonate, or a salt thereof; n is independently in each instance an integer from 0 to about 3; and x is an integer from about 1 to about 4.

20. The conjugate of clause 18 or 19 wherein the fluorescent dye is selected from the group consisting of an Oregon Green dye, an AlexaFluor dye, a fluorescein, a BODIPY dye, a rhodamine dye, a DyLight dye, CW 800, Texas Red, and phycoerythrin.

20.1. The conjugate of any one of clauses 18 to 19 wherein the fluorescent dye is selected from the group consisting of an Oregon Green dye, an AlexaFluor dye, a fluorescein, a BODIPY dye, a rhodamine dye, a DyLight dye, and phycoerythrin.

20.2. The conjugate of any one of clauses 18 to 20.1 wherein the fluorescent dye is CW 800 or Texas Red.

21. The conjugate of any one of clauses 18 to 20 wherein the fluorescent dye is selected from the group consisting of DyLight 680, DyLight 750, and Oregon Green 488.

21.1. The conjugate of any one of clauses 18 to 20.1 wherein the fluorescent dye is selected from the group consisting of DyLight 680, DyLight 750, and Oregon Green 488.

22. The conjugate of any one of clauses 18 to 21.1 wherein the conjugate has the formula

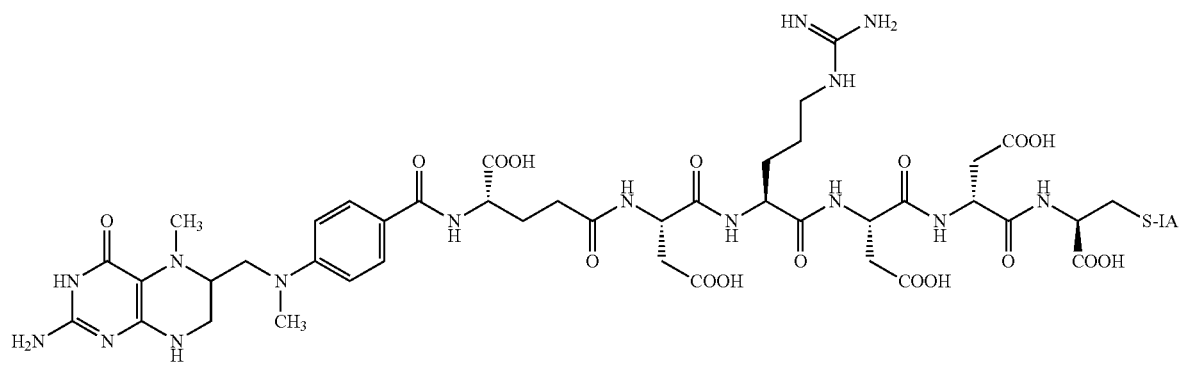

where IA is has the formula

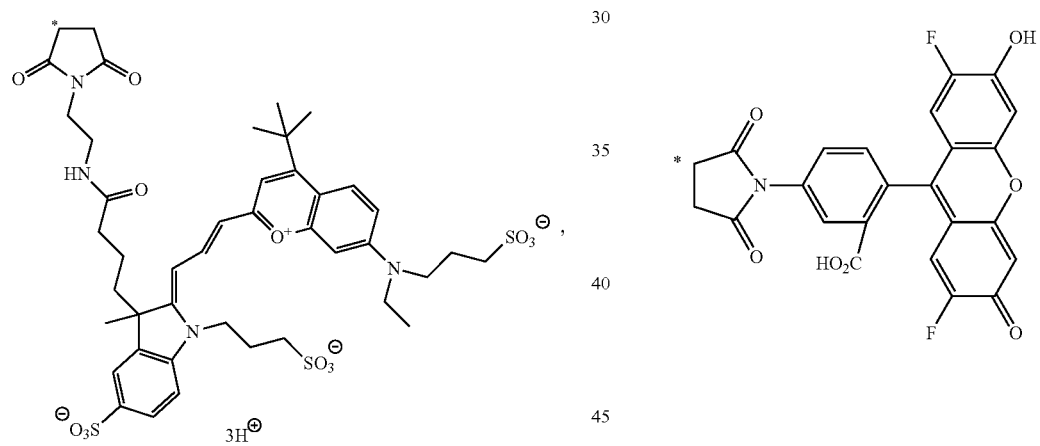

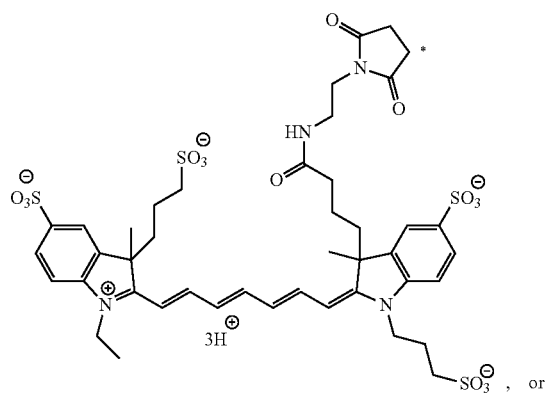

-continued where * indicates the site of attachment.

23. The conjugate of any one of clauses 1, 2, or 5 to 11.1 wherein the drug is a therapeutic agent.

24. The conjugate of clause 23 wherein the therapeutic agent is selected from the group consisting of a vinca alkaloid, a tubulysin, and an analog or derivative thereof.

25. The conjugate of clause 23 or 24 wherein the therapeutic agent is a vinca alkaloid, or an analog or a derivative thereof.

26. The conjugate of clause 23 or 24 wherein the therapeutic agent is a tubulysin, or an analog or a derivative thereof.

27. The conjugate of any one of clauses 23, 24, or 26 wherein the conjugate has the formula

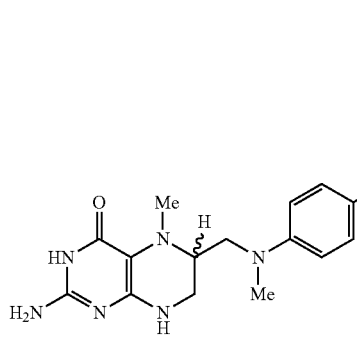
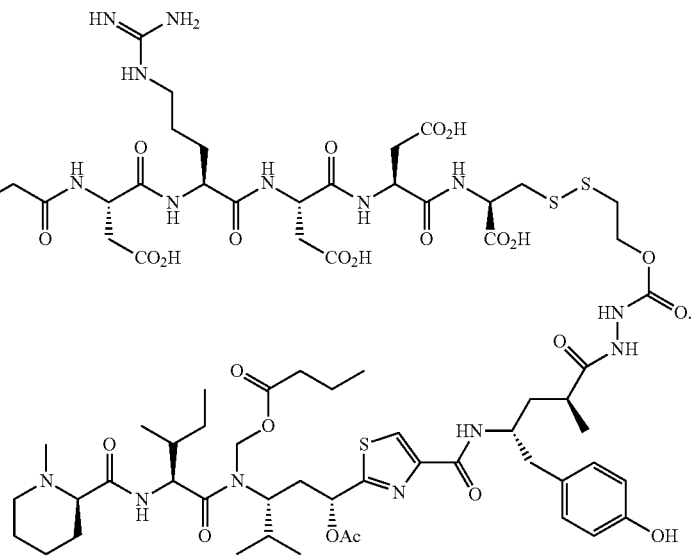

28. The conjugate of any one of clauses 23, 24, or 25 wherein the conjugate has the formula

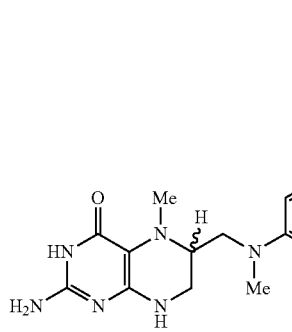

29. A pharmaceutical composition comprising an imaging effective or therapeutically effective amount of one or more of the conjugates of any one of clauses 1 to 28.

30. The composition of clause 29 further comprising one or more carriers, diluents, or excipients, or a combination thereof.

31. The composition of clause 30 in a parenteral dosage form.

32. A method for imaging cancer cells in a patient, the method comprising administering an imaging effective amount of the conjugate of any one of clauses 1-22 or the composition of clauses 29 to 31 to the patient; and imaging the cancer cells.

32.1. A method for imaging cancer cells in a patient, the method comprising administering an imaging effective amount of the conjugate of any one of clauses 1-22 where D is an imaging agent or the composition of clauses 29 to 31 where D is an imaging agent to the patient; and imaging the cancer cells.

33. A method for treating a patient in need of relief from cancer, the method comprising the step of administering to the patient the conjugate of any one of clauses 23 to 28 or the composition of any one of clauses 29 to 31.

34. A method for treating a patient in need of relief from cancer, the method comprising the step of administering to the patient a therapeutically effective amount of the conjugate of any one of clauses 23 to 28 or the composition of any one of clauses 29 to 31 where D is a therapeutic agent.

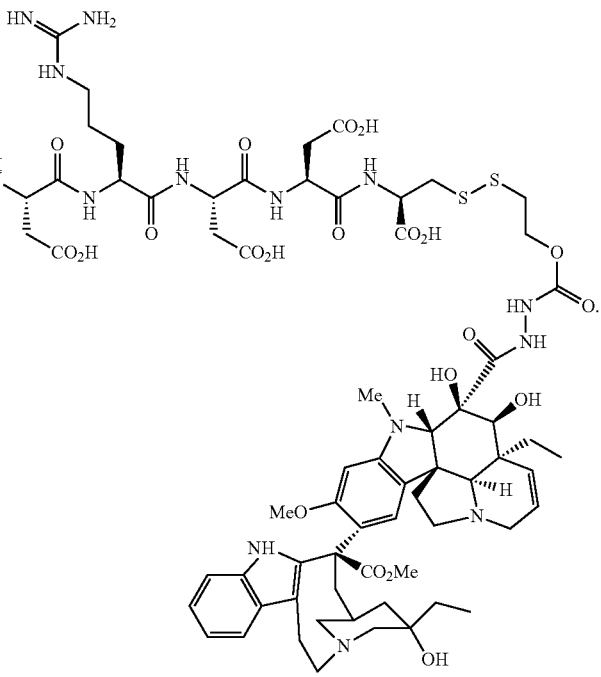

35. The conjugate, composition, or method of any one of claims 1 to 34 wherein the folate receptor alpha selective binding ligand (B) is

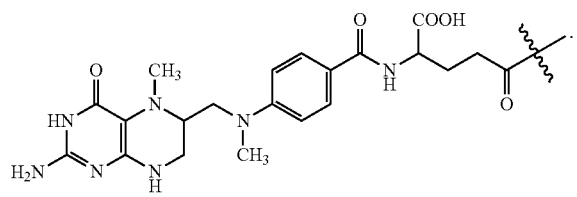 [SMILES: *C(=O)CCC(NC(=O)c1ccc(N(C)CC2CNc3nc(N)[nH]c(=O)c3N2C)cc1)C(=O)O]

It is appreciated that compounds and conjugates described herein may exist in one or more tautomeric forms. It is to be understood that the compounds and conjugates described herein include all tautomeric forms.

In another embodiment, the conjugates described herein include linker moieties covalently attached to the FR-α selective binding ligand (B) and the drug (D). Illustrative linkers (L) are described in U.S. Pat. No. 7,601,332 and in U.S. Patent Publication No. US 2010/0323973, the disclosures of which are incorporated herein by reference, in their entireties.

In another embodiment, the linker (L) is a chain of atoms selected from C, N, O, S, Si, and P. The linker (L) may have a wide variety of lengths, such as in the range from about 7 to about 100. The atoms used in forming the linker (L) may be combined in all chemically relevant ways, such as chains of carbon atoms forming alkylene groups, chains of carbon and oxygen atoms forming polyoxyalkylene groups, chains of carbon and nitrogen atoms forming polyamines, and others. In addition, it is to be understood that the bonds connecting atoms in the chain may be either saturated or unsaturated, such that for example, alkanes, alkenes, alkynes, cycloalkanes, arylenes, imides, and the like may be divalent radicals that are included in the linker (L). In addition, it is to be understood that the atoms forming the linker (L) may also be cyclized upon each other to form divalent cyclic radicals in the linker (L). In each of the foregoing and other linkers (L) described herein the chain forming the linker (L) may be substituted with a wide variety of groups.

In another embodiment, linkers (L) are described that include at least one releasable linker. In one variation, linkers (L) are described that include at least two releasable linkers. In another variation, linkers (L) are described that include at least one self-immolative linker. In another variation, linkers (L) are described that include at least one releasable linker that is not a disulfide. In another embodiment, linkers (L) are described that do not include a releasable linker.

It is appreciated that releasable linkers may be used when the drug (D) to be delivered is advantageously liberated from the binding ligand-linker conjugate so that the free drug (D) will have the same or nearly the same effect at the target as it would when administered without the targeting provided by the conjugates described herein. In another embodiment, the linker is a non-releasable linker. It is appreciated that non-releasable linkers may be used when the drug (D) is advantageously retained by the binding ligand-linker conjugate, such as in imaging and diagnosing uses of the conjugates described herein. It is to be understood that the choice of a releasable linker or a non-releasable linker may be made independently for each application or configuration of the conjugates, without limiting the invention described herein. It is to be further understood that the linkers (L) described herein comprise various atoms, chains of atoms, functional groups, and combinations of functional groups. Where appropriate in the present disclosure, the linker (L) may be referred to by the presence of spacer linkers, releasable linkers, and heteroatoms. However, such references are not to be construed as limiting the definition of the linkers (L) described herein.

The linker (L) comprising spacer and/or releasable linkers (i.e., cleavable linkers) can be any biocompatible linker. The releasable or cleavable linker can be, for example, a linker susceptible to cleavage under the reducing or oxidizing conditions present in or on cells, a pH-sensitive linker that may be an acid-labile or base-labile linker, or a linker that is cleavable by biochemical or metabolic processes, such as an enzyme-labile linker. In one embodiment, the spacer and/or releasable linker comprises about 1 to about 30 atoms, or about 2 to about 20 atoms. Lower molecular weight linkers (L) (i.e., those having an approximate molecular weight of about 30 to about 300) are also described. Precursors to any of the linkers (L) described herein may be selected to have either nucleophilic or electrophilic functional groups, or both, optionally in a protected form with a readily cleavable protecting group to facilitate their use in synthesis of the intermediate species.

The term "releasable linker" as used herein refers to a linker that includes at least one bond that can be broken under physiological conditions (e.g., a pH-labile, acid-labile, oxidatively-labile, or enzyme-labile bond). The cleavable bond or bonds may be present in the interior of a cleavable linker and/or at one or both ends of a cleavable linker. It should be appreciated that such physiological conditions resulting in bond breaking include standard chemical hydrolysis reactions that occur, for example, at physiological pH, or as a result of compartmentalization into a cellular organelle such as an endosome having a lower pH than cytosolic pH. Illustratively, the releasable linkers described herein may undergo cleavage under other physiological or metabolic conditions, such as by the action of a glutathione mediated mechanism. It is appreciated that the lability of the cleavable bond may be adjusted by including functional groups or fragments within the releasable linker that are able to assist or facilitate such bond breakage, also termed anchimeric assistance. The lability of the cleavable bond can also be adjusted by, for example, substitutional changes at or near the cleavable bond, such as including alpha branching adjacent to a cleavable disulfide bond, increasing the hydrophobicity of substituents on silicon in a moiety having a silicon-oxygen bond that may be hydrolyzed, homologating alkoxy groups that form part of a ketal or acetal that may be hydrolyzed, and the like. In addition, it is appreciated that additional functional groups or fragments may be included within the releasable linker that are able to assist or facilitate additional fragmentation of the FR-α selective binding ligand drug conjugates after bond breaking of the releasable linker.

In another embodiment, the linker (L) includes radicals that form one or more spacer linkers and/or releasable linkers that are taken together to form the linkers described herein having certain length, diameter, and/or functional group requirements.

Another illustrative embodiment of the linkers (L) described herein, include releasable linkers that cleave under the conditions described herein by a chemical mechanism involving beta elimination. In one aspect, such releasable linkers include beta-thio, beta-hydroxy, and beta-amino substituted carboxylic acids and derivatives thereof, such as esters, amides, carbonates, carbamates, and ureas. In another aspect, such releasable linkers include 2- and 4-thioarylesters, carbamates, and carbonates.

It is to be understood that releasable linkers may also be referred to by the functional groups they contain, illustratively such as disulfide groups, ketal groups, and the like, as described herein. Accordingly, it is understood that a cleavable bond can connect two adjacent atoms within the releasable linker and/or connect other linkers, or the FR-α selective binding ligand (B), or the therapeutic, diagnostic, or imaging agent, as described herein, at either or both ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as an additional heteroatom, a spacer linker, another releasable linker, the drug (D), or analog or derivative thereof, or the FR-α selective binding ligand (B), or analog or derivative thereof, following breakage of the bond, the releasable linker is separated from the other moiety.

In another embodiment, the releasable and spacer linkers may be arranged in such a way that subsequent to the cleavage of a bond in the releasable linker released functional groups anchimerically assist the breakage or cleavage of additional bonds, as described above. An illustrative embodiment of such a releasable linker or portion thereof includes compounds having the formula:

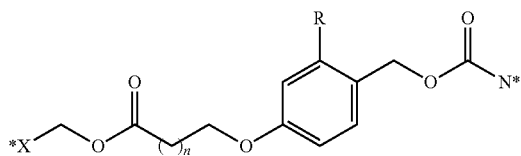

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and the symbol (*) indicates points of attachment for additional spacer or releasable linkers, or heteroatoms, forming the releasable linker, or alternatively for attachment of the drug (D), or analog or derivative thereof, or the FR-α selective binding ligand (B), or analog or derivative thereof. It is appreciated that other substituents may be present on the aryl ring, the benzyl carbon, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically assisted mechanism.

In this embodiment, the hydroxyalkanoic acid, which may cyclize, facilitates cleavage of the methylene bridge, by for example an oxonium ion, and facilitates bond cleavage or subsequent fragmentation after bond cleavage of the releasable linker. Alternatively, acid catalyzed oxonium ion-assisted cleavage of the methylene bridge may begin a cascade of fragmentation of this illustrative releasable linker, or fragment thereof. Alternatively, acid-catalyzed hydrolysis of the carbamate may facilitate the beta elimination of the hydroxyalkanoic acid, which may cyclize, and facilitate cleavage of the methylene bridge, by for example an oxonium ion. It is appreciated that other chemical mechanisms of bond breakage or cleavage under the metabolic, physiological, or cellular conditions described herein may initiate such a cascade of fragmentation. It is appreciated that other chemical mechanisms of bond breakage or cleavage under the metabolic, physiological, or cellular conditions described herein may initiate such a cascade of fragmentation.

Illustrative mechanisms for cleavage of the releasable linkers described herein include the following 1,4 and 1,6 fragmentation mechanisms

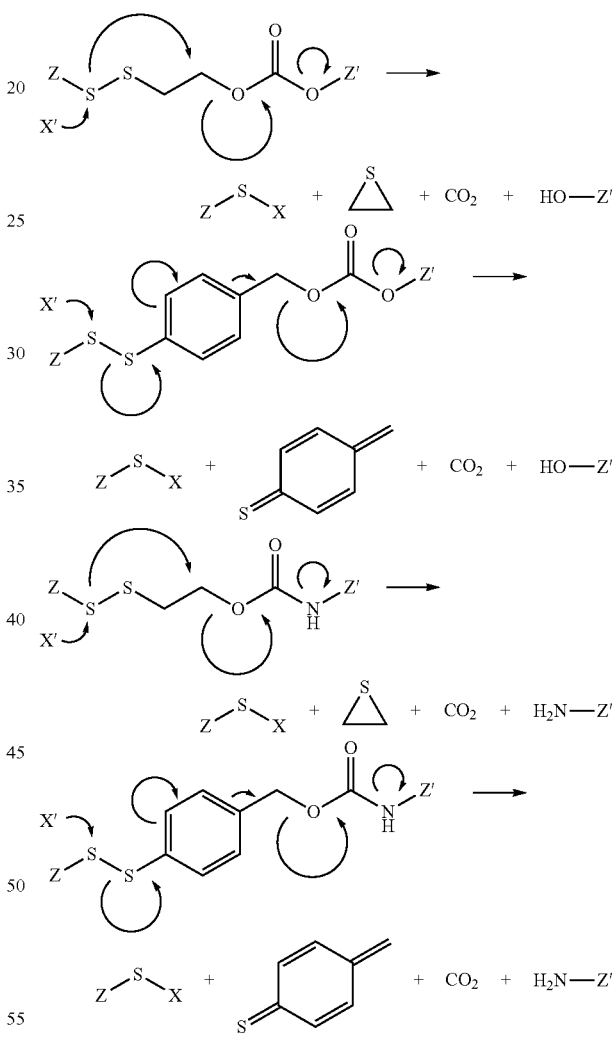

where X is an exogenous or endogenous nucleophile, glutathione, or bioreducing agent, and the like, and either of Z or Z' is a FR-α selective binding ligand, or a drug (e.g. a therapeutic agent, a diagnostic agent, or a imaging agent), or either of Z or Z' is a FR-α selective binding ligand, or a drug connected through other portions of the linker (L). It is to be understood that although the above fragmentation mechanisms are depicted as concerted mechanisms, any number of discrete steps may take place to effect the ultimate fragmentation of the releasable linker to the final products shown.

For example, it is appreciated that the bond cleavage may also occur by acid catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In the case of the benzyl-containing releasable linkers, following an illustrative breaking of the disulfide bond, the resulting phenyl thiolate may further fragment to release a carbonic acid or carbamic acid moiety by forming a resonance stabilized intermediate. In any of these cases, the releasable nature of the illustrative linkers described herein may be realized by whatever mechanism may be relevant to the chemical, metabolic, physiological, or biological conditions present.

Other illustrative mechanisms for bond cleavage of the releasable linker include oxonium-assisted cleavage as follows:

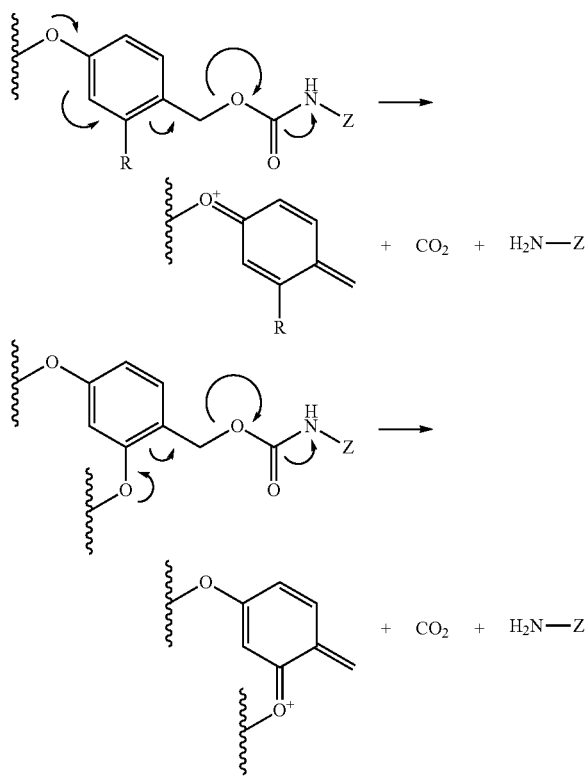

where Z is the FR-α selective binding ligand, or analog or derivative thereof, or the drug, or analog or derivative thereof, or each is a FR-α selective binding ligand or drug moiety in conjunction with other portions of the linker, such as a drug or FR-α selective binding ligand moiety including one or more spacer linkers and/or other releasable linkers. In this embodiment, acid-catalyzed elimination of the carbamate leads to the release of $CO_2$ and the nitrogen-containing moiety attached to Z, and the formation of a benzyl cation, which may be trapped by water, or any other Lewis base.

In one embodiment, the releasable linker includes a disulfide.

In another embodiment, the releasable linker may be a divalent radical comprising alkyleneaziridin-1-yl, alkylenecarbonylaziridin-1-yl, carbonylalkylaziridin-1-yl, alkylenesulfoxylaziridin-1-yl, sulfoxylalkylaziridin-1-yl, sulfonylalkylaziridin-1-yl, or alkylenesulfonylaziridin-1-yl, wherein each of the releasable linkers is optionally substituted with a substituent $X^2$, as defined below.

Additional illustrative releasable linkers include methylene, 1-alkoxyalkylene, 1-alkoxycycloalkylene, 1-alkoxyalkylenecarbonyl, 1-alkoxycycloalkylenecarbonyl, carbonylarylcarbonyl, carbonyl(carboxyaryl)carbonyl, carbonyl(biscarboxyaryl)carbonyl, haloalkylenecarbonyl, alkylene(dialkylsilyl), alkylene(alkylarylsilyl), alkylene(diarylsilyl), (dialkylsilyl)aryl, (alkylarylsilyl)aryl, (diarylsilyl)aryl, oxycarbonyloxy, oxycarbonyloxyalkyl, sulfonyloxy, oxysulfonylalkyl, iminoalkylidenyl, carbonylalkylideniminyl, iminocycloalkylidenyl, carbonylcycloalkylideniminyl, alkylenethio, alkylenearylthio, and carbonylalkylthio, wherein each of the releasable linkers is optionally substituted with a substituent $X^2$, as defined below.

In the preceding embodiment, the releasable linker may include oxygen, and the releasable linkers can be methylene, 1-alkoxyalkylene, 1-alkoxycycloalkylene, 1-alkoxyalkylenecarbonyl, and 1-alkoxycycloalkylenecarbonyl, wherein each of the releasable linkers is optionally substituted with a substituent $X^2$, as defined below, and the releasable linker is bonded to the oxygen to form an acetal or ketal. Alternatively, the releasable linker may include oxygen, and the releasable linker can be methylene, wherein the methylene is substituted with an optionally-substituted aryl, and the releasable linker is bonded to the oxygen to form an acetal or ketal. Further, the releasable linker may include oxygen, and the releasable linker can be sulfonylalkyl, and the releasable linker is bonded to the oxygen to form an alkylsulfonate.

In another embodiment of the above releasable linker embodiment, the releasable linker may include nitrogen, and the releasable linkers can be iminoalkylidenyl, carbonylalkylideniminyl, iminocycloalkylidenyl, and carbonylcycloalkylideniminyl, wherein each of the releasable linkers is optionally substituted with a substituent $X^2$, as defined below, and the releasable linker is bonded to the nitrogen to form an hydrazone. In an alternate configuration, the hydrazone may be acylated with a carboxylic acid derivative, an orthoformate derivative, or a carbamoyl derivative to form various acylhydrazone releasable linkers.

Alternatively, the releasable linker may include oxygen, and the releasable linkers can be alkylene(dialkylsilyl), alkylene(alkylarylsilyl), alkylene(diarylsilyl), (dialkylsilyl)aryl, (alkylarylsilyl)aryl, and (diarylsilyl)aryl, wherein each of the releasable linkers is optionally substituted with a substituent $X^2$, as defined below, and the releasable linker is bonded to the oxygen to form a silanol.

In the above releasable linker embodiment, the drug (D) can include a nitrogen atom, the releasable linker may include nitrogen, and the releasable linkers can be carbonylarylcarbonyl, carbonyl(carboxyaryl)carbonyl, carbonyl(biscarboxyaryl)carbonyl, and the releasable linker can be bonded to the heteroatom nitrogen to form an amide, and also bonded to the drug nitrogen to form an amide.

In the above releasable linker embodiment, the drug (D) can include an oxygen atom, the releasable linker may include nitrogen, and the releasable linkers can be carbonylarylcarbonyl, carbonyl(carboxyaryl)carbonyl, carbonyl (biscarboxyaryl)carbonyl, and the releasable linker can form an amide, and also bonded to the drug oxygen to form an ester.

The substituents $X^2$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the releasable linker can include nitrogen, and the substituent $X^2$ and the releasable linker can form a heterocycle.

The heterocycles can be pyrrolidines, piperidines, oxazolidines, isoxazolidines, thiazolidines, isothiazolidines, pyrrolidinones, piperidinones, oxazolidinones, isoxazolidinones, thiazolidinones, isothiazolidinones, and succinimides.

In one embodiment, the linkers (L) described herein are or include compounds of the following formulae:

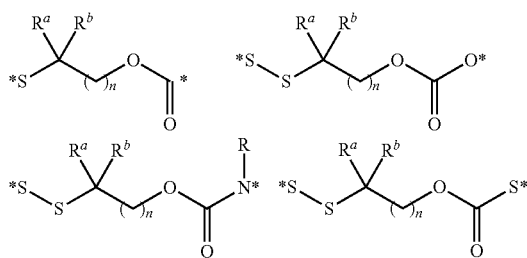

where n is an integer selected from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; R is an optionally substituted alkyl group, an optionally substituted acyl group, or a suitably selected nitrogen protecting group; and (*) indicates points of attachment for the drug (D), FR-α selective binding ligand (B), other linkers, or other parts of the conjugate.

In another embodiment, the linkers (L) described herein are or include compounds of the following formulae

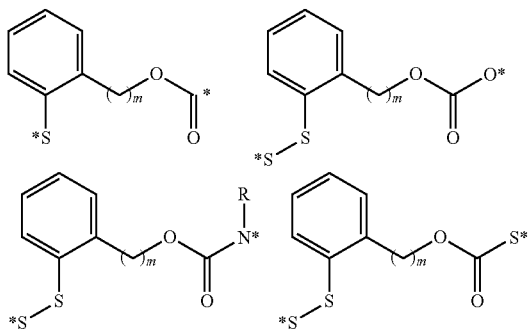

where m is an integer selected from 1 to about 4; R is an optionally substituted alkyl group, an optionally substituted acyl group, or a suitably selected nitrogen protecting group; and (*) indicates points of attachment for the drug (D), FR-α selective binding ligand (B), other linkers, or other parts of the conjugate.

In another embodiment, the linkers described herein are or include compounds of the following formulae

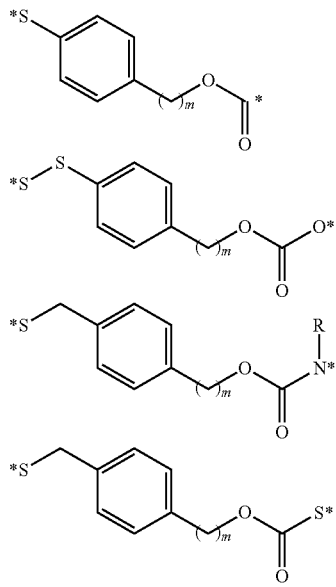

where m is an integer selected from 1 to about 4; R is an optionally substituted alkyl group, an optionally substituted acyl group, or a suitably selected nitrogen protecting group; and (*) indicates points of attachment for the drug (D), FR-α selective binding ligand (B), other linkers, or other parts of the conjugate.

In another embodiment, the linker (L) includes one or more spacer linkers. Such spacer linkers can be 1-alkylenesuccinimid-3-yl, optionally substituted with a substituent $X^1$, as defined below, and the releasable linkers can be methylene, 1-alkoxyalkylene, 1-alkoxycycloalkylene, 1-alkoxyalkylenecarbonyl, 1-alkoxycycloalkylenecarbonyl, wherein each of the releasable linkers is optionally substituted with a substituent $X^2$, as defined below, and wherein the spacer linker and the releasable linker are each bonded to the spacer linker to form a succinimid-1-ylalkyl acetal or ketal.

The spacer linkers can be carbonyl, thionocarbonyl, alkylene, cycloalkylene, alkylenecycloalkyl, alkylenecarbonyl, cycloalkylenecarbonyl, carbonylalkylcarbonyl, 1-alkylenesuccinimid-3-yl, 1-(carbonylalkyl)succinimid-3-yl, alkylenesulfoxyl, sulfonylalkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl)succinimid-3-yl, and 1-(carbonyltetrahydrofuranyl)succinimid-3-yl, wherein each of the spacer linkers is optionally substituted with a substituent $X^1$, as defined below. In this embodiment, the spacer linker may include an additional nitrogen, and the spacer linkers can be alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$, as defined below, and the spacer linker is bonded to the nitrogen to form an amide. Alternatively, the spacer linker may include an additional sulfur, and the spacer linkers can be alkylene and cycloalkylene, wherein each of the spacer linkers is optionally substituted with carboxy, and the spacer linker is bonded to the sulfur to form a thiol. In another embodiment, the spacer linker can include sulfur, and the spacer linkers can be 1-alkylenesuccinimid-3-yl and 1-(carbonylalkyl)succinimid-3-yl, and the spacer linker is bonded to the sulfur to form a succinimid-3-ylthiol.

In an alternative to the above-described embodiments, the spacer linker can include nitrogen, and the releasable linker can be a divalent radical comprising alkyleneaziridin-1-yl, carbonylalkylaziridin-1-yl, sulfoxylalkylaziridin-1-yl, or sulfonylalkylaziridin-1-yl, wherein each of the releasable linkers is optionally substituted with a substituent $X^2$, as defined below. In this alternative embodiment, the spacer linkers can be carbonyl, thionocarbonyl, alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$, as defined below, and wherein the spacer linker is bonded to the releasable linker to form an aziridine amide.

The substituents $X^1$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the spacer linker can include nitrogen, and the substituent $X^1$ and the spacer linker to which they are bound to form an heterocycle.

Additional illustrative spacer linkers include alkyleneamino-alkylenecarbonyl, alkylene-thio-(carbonylalkylsuccinimid-3-yl), and the like, as further illustrated by the following formulae:

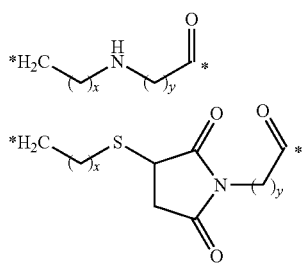

where the integers x and y are 1, 2, 3, 4, or 5:

In another embodiment, linkers (L) that include hydrophilic regions are also described. In one aspect, the hydrophilic region of the linker (L) forms part or all of a spacer linker included in the conjugates described herein. Illustrative hydrophilic spacer linkers are described in U.S. Patent Publication No. US 2010/0323973, the disclosure of which is incorporated herein by reference, in its entirety.

Another illustrative embodiment of the linkers (L) described herein, include releasable linkers that cleave under the conditions described herein by a chemical mechanism involving beta elimination. In one aspect, such releasable linkers include beta-thio, beta-hydroxy, and beta-amino substituted carboxylic acids and derivatives thereof, such as esters, amides, carbonates, carbamates, and ureas. In another aspect, such releasable linkers include 2- and 4-thioarylesters, carbamates, and carbonates.

In another illustrative embodiment, the linker (L) includes one or more amino acids. In one variation, the linker (L) includes a single amino acid. In another variation, the linker (L) includes a peptide having from 2 to about 50, 2 to about 30, or 2 to about 20 amino acids. In another variation, the linker (L) includes a peptide having from about 4 to about 8 amino acids. Such amino acids are illustratively selected from the naturally occurring amino acids, or stereoisomers thereof. The amino acid may also be any other amino acid, such as any amino acid having the general formula:

—N(R)—(CR'R'')$_q$—C(O)— where R is hydrogen, alkyl, acyl, or a suitable nitrogen protecting group, R' and R'' are hydrogen or a substituent, each of which is independently selected in each occurrence, and q is an integer such as 1, 2, 3, 4, or 5. Illustratively, R' and/or R'' independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornithine, threonine, and the like. In one variation, the releasable linker includes at least 2 amino acids selected from asparagine, aspartic acid, cysteine, glutamic acid, lysine, glutamine, arginine, serine, ornithine, and threonine. In another variation, the releasable linker includes between 2 and about 5 amino acids selected from asparagine, aspartic acid, cysteine, glutamic acid, lysine, glutamine, arginine, serine, ornithine, and threonine. In another variation, the releasable linker includes a tripeptide, tetrapeptide, pentapeptide, or hexapeptide consisting of amino acids selected from aspartic acid, cysteine, glutamic acid, lysine, arginine, and ornithine, and combinations thereof.

The term amino acid as used herein refers generally to aminoalkylcarboxylate, where the alkyl radical is optionally substituted, such as with alkyl, hydroxy alkyl, sulfhydrylalkyl, aminoalkyl, carboxyalkyl, and the like, including groups corresponding to the naturally occurring amino acids, such as serine, cysteine, methionine, aspartic acid, glutamic acid, and the like. It is to be understood that such amino acids may be of a single stereochemistry or a particular mixture of stereochemistries, including racemic mixtures.

The term "cycloalkylene" as used herein includes molecular fragments or radicals comprising a bivalent chain of carbon atoms, a portion of which forms a ring. It is to be understood that the term cycloalkyl as used herein includes fragments and radicals attached at either ring atoms or non-ring atoms, such as cycloprop-1,1-diyl, cycloprop-1,2-diyl, cyclohex-1,4-diyl, 3-ethylcyclopent-1,2-diyl, 1-methylenecyclohex-4-yl, and the like.

The terms "heteroalkyl" and "heteroalkylene" as used herein includes molecular fragments or radicals comprising monovalent and divalent, respectively, groups that are formed from a linear or branched chain of carbon atoms and heteroatoms, wherein the heteroatoms are selected from nitrogen, oxygen, and sulfur, such as alkoxyalkyl, alkyleneoxyalkyl, aminoalkyl, alkylaminoalkyl, alkyleneaminoalkyl, alkylthioalkyl, alkylenethioalkyl, alkoxyalkylaminoalkyl, alkylaminoalkoxyalkyl, alkyleneoxyalkylaminoalkyl, and the like.

The term "heterocyclyl" as used herein includes molecular fragments or radicals comprising a monovalent chain of carbon atoms and heteroatoms, wherein the heteroatoms are selected from nitrogen, oxygen, and sulfur, a portion of which, including at least one heteroatom, form a ring, such as aziridine, pyrrolidine, oxazolidine, 3-methoxypyrrolidine, 3-methylpiperazine, and the like. Accordingly, as used herein, heterocyclyl includes alkylheterocyclyl, heteroalkylheterocyclyl, heterocyclylalkyl, heterocyclylheteroalkyl, and the like. It is to be understood that the term heterocyclyl as used herein includes fragments and radicals attached at either ring atoms or non-ring atoms, such as tetrahydrofuran-2-yl, piperidin-1-yl, piperidin-4-yl, piperazin-1-yl, morpholin-1-yl, tetrahydrofuran-2-ylmethyl, piperidin-1-ylethyl, piperidin-4-ylmethyl, piperazin-1-ylpropyl, morpholin-1-ylethyl, and the like.

The term "substituted aryl" or "substituted heteroaryl" as used herein includes molecular fragments or radicals comprising aryl or heteroaryl substituted with one or more substituents, such as alkyl, heteroalkyl, halo, hydroxy, amino, alkyl or dialkylamino, alkoxy, alkylsulfonyl, aminosulfonyl, carboxylate, alkoxycarbonyl, aminocarbonyl, cyano, nitro, and the like. It is to be understood that the alkyl groups in such substituents may be optionally substituted with halo.

The term "iminoalkylidenyl" as used herein includes molecular fragments or radicals comprising a divalent radical containing alkylene as defined herein and a nitrogen atom, where the terminal carbon of the alkylene is double-bonded to the nitrogen atom, such as the formulae —(CH)=N—, —(CH$_2$)$_2$(CH)=N—, —CH$_2$C(Me)=N—, and the like.

The term "amino acid" as used herein includes molecular fragments or radicals comprising an aminoalkylcarboxylate, where the alkyl radical is optionally substituted with alkyl, hydroxy alkyl, sulfhydrylalkyl, aminoalkyl, carboxyalkyl, and the like, including groups corresponding to the naturally occurring amino acids, such as serine, cysteine, methionine, aspartic acid, glutamic acid, and the like.

For example, in one embodiment, amino acid is a divalent radical having the general formula:

where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornithine, threonine, and the like. In one variation, the amino acid may be selected from phenylalanine, tyrosine, and the like, derivatives thereof, and substituted variants thereof.

The terms "arylalkyl" and "heteroarylalkyl" as used herein includes molecular fragments or radicals comprising aryl and heteroaryl, respectively, as defined herein substituted with a linear or branched alkylene group, such as benzyl, phenethyl, α-methylbenzyl, picolinyl, pyrimidinylethyl, and the like.

It is to be understood that the above-described terms can be combined to generate chemically-relevant groups, such as "haloalkoxyalkyl" referring to for example trifluoromethyloxyethyl, 1,2-difluoro-2-chloroeth-1-yloxypropyl, and the like.

The term "amino acid derivative" as used herein refers generally to aminoalkylcarboxylate, where the amino radical or the carboxylate radical are each optionally substituted with alkyl, carboxylalkyl, alkylamino, and the like, or optionally protected; and the intervening divalent alkyl fragment is optionally substituted with alkyl, hydroxy alkyl, sulfhydrylalkyl, aminoalkyl, carboxyalkyl, and the like, including groups corresponding to the side chains found in naturally occurring amino acids, such as are found in serine, cysteine, methionine, aspartic acid, glutamic acid, and the like.

The term "peptide" as used herein includes molecular fragments or radicals comprising a series of amino acids and amino acid analogs and derivatives covalently linked one to the other by amide bonds.

In another embodiment, the linker (L) comprises a spacer linker and a releasable linker taken together to form 3-thiosuccinimid-1-ylalkyloxymethyloxy, where the methyl is optionally substituted with alkyl or substituted aryl.

In another embodiment, the linker (L) comprises a spacer linker and a releasable linker taken together to form 3-thiosuccinimid-1-ylalkylcarbonyl, where the carbonyl forms an acylaziridine with the drug (D), or analog or derivative thereof.

In another embodiment, the linker (L) comprises a spacer linker and a releasable linker taken together to form 1-alkoxycycloalkylenoxy.

In another embodiment, the linker (L) comprises a spacer linker and a releasable linker taken together to form alkyleneaminocarbonyl(dicarboxylarylene)carboxylate.

In another embodiment, the linker (L) comprises a releasable linker, a spacer linker, and a releasable linker taken together to form dithioalkylcarbonylhydrazide, where the hydrazide forms an hydrazone with the drug (D), or analog or derivative thereof.

In another embodiment, the linker (L) comprises a spacer linker and a releasable linker taken together to form 3-thiosuccinimid-1-ylalkylcarbonylhydrazide, where the hydrazide forms an hydrazone with the drug (D), or analog or derivative thereof.

In another embodiment, the linker (L) comprises a spacer linker and a releasable linker taken together to form 3-thioalkylsulfonylalkyl(disubstituted silyl)oxy, where the disubstituted silyl is substituted with alkyl or optionally substituted aryl.

In another embodiment, the linker (L) comprises a plurality of spacer linkers selected from the group consisting of the naturally occurring amino acids and stereoisomers thereof.

In another embodiment, the linker (L) comprises a releasable linker, a spacer linker, and a releasable linker taken together to form 2-dithioalkyloxycarbonyl, where the carbonyl forms a carbonate with the drug (D), or analog or derivative thereof.

In another embodiment, the linker (L) comprises a releasable linker, a spacer linker, and a releasable linker taken together to form 2-dithioarylalkyloxycarbonyl or 4-dithioarylalkyloxycarbonyl, where the carbonyl forms a carbonate with the drug (D), or analog or derivative thereof, and the aryl is optionally substituted.

In another embodiment, the linker (L) comprises a spacer linker and a releasable linker taken together to form 3-thiosuccinimid-1-ylalkyloxyalkyloxyalkylidene, where the alkylidene forms an hydrazone with the drug (D), or analog or derivative thereof, each alkyl is independently selected, and the oxyalkyloxy is optionally substituted with alkyl or optionally substituted aryl.

In another embodiment, the linker (L) comprises a releasable linker, a spacer linker, and a releasable linker taken together to form 2-dithioalkyloxycarbonylhydrazide.

In another embodiment, the linker (L) comprises a releasable linker, a spacer linker, and a releasable linker taken together to form 2-dithioalkylamino, where the amino forms a vinylogous amide with the drug (D), or analog or derivative thereof.

In another embodiment, the linker (L) comprises a releasable linker, a spacer linker, and a releasable linker taken together to form 2-dithioalkylamino, where the amino forms a vinylogous amide with the drug (D), or analog or derivative thereof, and the alkyl is ethyl.

In another embodiment, the linker (L) comprises a releasable linker, a spacer linker, and a releasable linker taken together to form 2-dithioalkylaminocarbonyl, where the carbonyl forms a carbamate with the drug (D), or analog or derivative thereof.

In another embodiment, the linker (L) comprises a releasable linker, a spacer linker, and a releasable linker taken together to form 2-dithioalkylaminocarbonyl, where the carbonyl forms a carbamate with the drug (D), or analog or derivative thereof, and the alkyl is ethyl.

In another embodiment, the linker (L) comprises a releasable linker, a spacer linker, and a releasable linker taken together to form 2-dithioarylalkyloxycarbonyl or 4-dithioarylalkyloxycarbonyl, where the carbonyl forms a carbamate or a carbamoylaziridine with the drug (D), or analog or derivative thereof.

In another embodiment, the linker (L) includes spacer linkers and releasable linkers connected to form a polyvalent 3-thiosuccinimid-1-ylalkyloxymethyloxy group, illustrated by the following formula

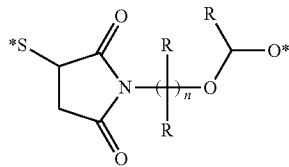

where n is an integer from 1 to 6, the alkyl group is optionally substituted, and the methyl is optionally substituted with an additional alkyl or optionally substituted aryl group, each of which is represented by an independently selected group R. The (*) symbols indicate points of attachment of the linker fragment to other parts of the conjugates described herein.

In another embodiment, the linker includes spacer linkers and releasable linkers connected to form a polyvalent 3-thiosuccinimid-1-ylalkylcarbonyl group, illustrated by the following formula

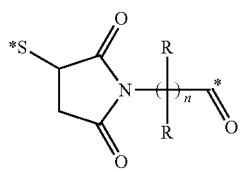

where n is an integer from 1 to 6, and the alkyl group is optionally substituted. The (*) symbols indicate points of attachment of the linker fragment to other parts of the conjugates described herein. In another embodiment, the linker includes spacer linkers and releasable linkers connected to form a polyvalent 3-thioalkylsulfonylalkyl(disubstituted silyl)oxy group, where the disubstituted silyl is substituted with alkyl and/or optionally substituted aryl groups.

In another embodiment, the linker (L) includes spacer linkers and releasable linkers connected to form a polyvalent dithioalkylcarbonylhydrazide group, or a polyvalent 3-thiosuccinimid-1-ylalkylcarbonylhydrazide, illustrated by the following formulae

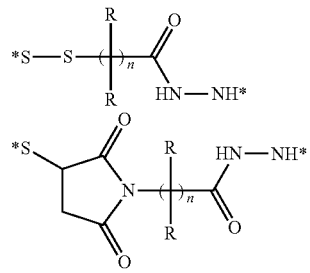

where n is an integer from 1 to 6, the alkyl group is optionally substituted, and the hydrazide forms an hydrazone with B, D, or another part of the linker (L). The (*) symbols indicate points of attachment of the linker fragment to other parts of the conjugates described herein.

In another embodiment, the linker (L) includes spacer linkers and releasable linkers connected to form a polyvalent 3-thiosuccinimid-1-ylalkyloxyalkyloxyalkylidene group, illustrated by the following formula

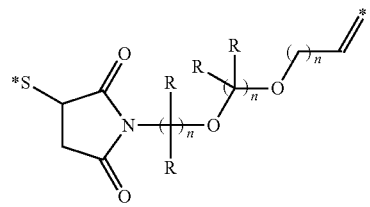

where each n is an independently selected integer from 1 to 6, each alkyl group independently selected and is optionally substituted, such as with alkyl or optionally substituted aryl, and where the alkylidene forms an hydrazone with B, D, or another part of the linker (L). The (*) symbols indicate points of attachment of the linker fragment to other parts of the conjugates described herein.

Additional illustrative linkers (L) are described in WO 2006/012527, the disclosure of which is incorporated herein by reference. Each of the spacer and releasable linkers described herein can be bivalent. In addition, the connections between spacer linkers, releasable linkers, drugs (D) and FR-α selective binding ligand (B) may occur at any atom found in the various spacer linkers, releasable linkers, drugs (D), and FR-α selective binding ligand (B).

The drug (D) can include a nitrogen atom, and the releasable linker can be haloalkylenecarbonyl, optionally substituted with a substituent $X^2$, and the releasable linker is bonded to the drug (D) nitrogen to form an amide.

The drug (D) can include an oxygen atom, and the releasable linker can be haloalkylenecarbonyl, optionally substituted with a substituent $X^2$, and the releasable linker is bonded to the drug (D) oxygen to form an ester.

The drug (D) can include a double-bonded nitrogen atom, and in this embodiment, the releasable linkers can be alkylenecarbonylamino and 1-(alkylenecarbonylamino)succinimid-3-yl, and the releasable linker can be bonded to the drug (D) nitrogen to form an hydrazone.

The drug (D) can include a sulfur atom, and in this embodiment, the releasable linkers can be alkylenethio and carbonylalkylthio, and the releasable linker can be bonded to the drug (D) sulfur to form a disulfide.

In one illustrative embodiment, the drug (D) is an imaging agent. In another illustrative variation, the drug (D) is a diagnostic agent. In another illustrative variation, the drug (D) is a therapeutic agent.

In one aspect, the imaging agent is a radioisotope covalently attached to the linker (L). In another embodiment, the imaging agent may include a positron-emitting radioisotope having a suitable half-life and toxicity profile. In various embodiments, the radioisotope is selected from group consisting of $^{34}Cl$, $^{45}Ti$, $^{51}Mn$, $^{61}Cu$, $^{63}Zn$, $^{68}Ga$, $^{11}C$, $^{13}N$, $^{15}O$, and $^{18}F$. In one illustrative embodiment, the radioisotope is $^{18}F$. In another aspect, the imaging agent is a radioactive isotope, such as a radioactive isotope of a metal, coordinated to a chelating group. Illustrative radioactive metal isotopes include technetium, rhenium, gallium, gadolinium, indium, copper, and the like, including isotopes $^{111}In$, $^{99m}Tc$, $^{64}Cu$, $^{67}Cu$, $^{67}Ga$, $^{68}Ga$, and the like. Additional illustrative examples of radionuclide imaging agents are described in U.S. Pat. No. 7,128,893, the disclosure of which is incorporated herein by reference. Additional illustrative chelating groups are tripeptide or tetrapeptides, including but not limited to tripeptides having the formula:

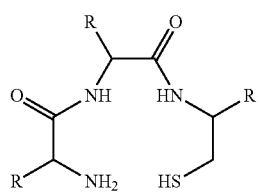

wherein R is independently selected in each instance from hydrogen, or alkyl, heteroalkyl, cycloalkyl, heterocyclyl, alkenyl, alkynyl, aryl, heteroaryl, arylalkyl, heteroarylalkyl, carboxylic acid or a derivative thereof, and the like, each of which is optionally substituted. It is to be understood that one R includes a heteroatom, such as nitrogen, oxygen, or sulfur, and is the point of attachment of linker L. Illustratively, the following chelating groups are described:

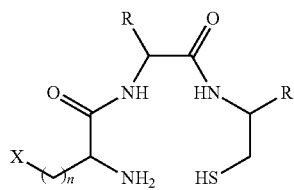

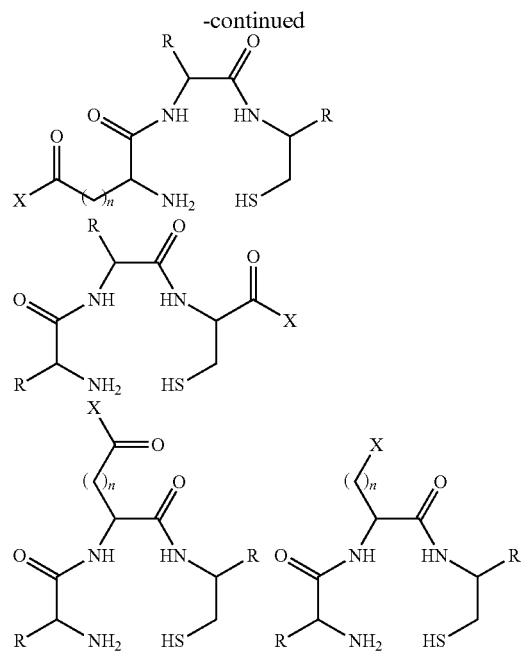

where X is oxygen, nitrogen, or sulfur, and where X is attached to linker L, and n is an integer from 1 to about 5.

In another illustrative embodiment, the chelating group is:

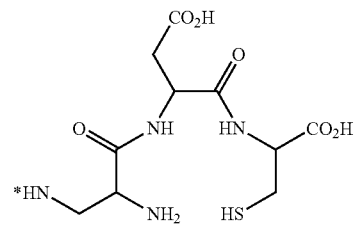

where * indicates that site of attachment of the linker L.

In another aspect, the imaging agent is a fluorescent agent. Fluorescent agents include Oregon Green fluorescent agents, including but not limited to Oregon Green 488, Oregon Green 514, and the like, AlexaFluor fluorescent agents, including but not limited to AlexaFluor 488, AlexaFluor 647, and the like, fluorescein, and related analogs, BODIPY fluorescent agents, including but not limited to BODIPY F1, BODIPY 505, and the like, rhodamine fluorescent agents, including but not limited to tetramethylrhodamine, and the like, DyLight fluorescent agents, including but not limited to DyLight 680, DyLight 750, DyLight 800, and the like, CW 800, Texas Red, phycoerythrin, and others. Illustrative fluorescent agents are shown in the following illustrative general structures:

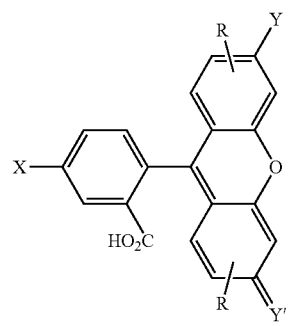

where X is oxygen, nitrogen, or sulfur, and where X is attached to linker L; Y is $OR^a$, $NR^a_2$, or $NR^a_3{}^+$; and Y' is O, $NR^a$, or $NR^a_2{}^+$; where each R is independently selected in each instance from hydrogen, fluoro, sulfonic acid, sulfonate, and salts thereof, and the like; and $R^a$ is hydrogen or alkyl.

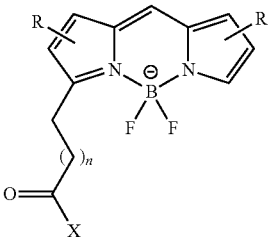

where X is oxygen, nitrogen, or sulfur, and where X is attached to linker L; and each R is independently selected in each instance from hydrogen, alkyl, heteroalkyl, and the like; and n is an integer from 0 to about 4.

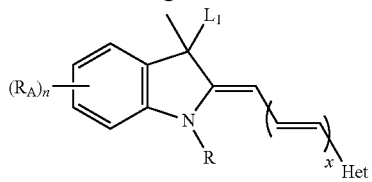

where Het is selected from the group consisting of

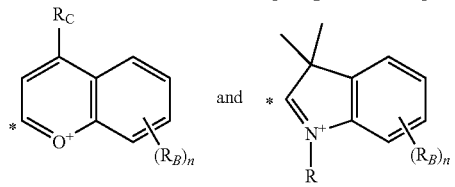

where * is the attachment point; where $R_A$ and $R_B$ are independently selected in each instance from alkyl, heteroalkyl, alkylsulfonic acid, alkylsulfonate, or a salt thereof, or an amine or a derivative thereof; $R_C$ is alkyl or heteroalkyl; $L_1$ is an alkylene attached to linker L; R is independently selected in each instance from alkyl, heteroalkyl, or alkylsulfonic acid, or alkylsulfonate, or a salt thereof; n is independently in each instance an integer from 0 to about 3; and x is an integer from about 1 to about 4. In another aspect, the infrared dye is IRDye®800CW

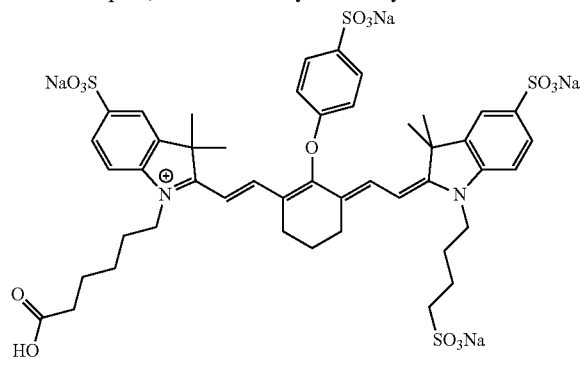

IRDye® 800 CW carboxylate

In another aspect, the imaging agent is a PET imaging agent, or a FRET imaging agent. PET imaging agents include $^{18}$F, $^{11}$C, $^{64}$Cu, $^{65}$Cu, and the like. FRET imaging agents include $^{64}$Cu, $^{65}$Cu, and the like. It appreciated that in the case of $^{18}$F or $^{11}$C, for example, the imaging isotope may be present on any part of the linker (L), or alternatively may be present on a structure attached to the linker (L). For example in the case of $^{18}$F, fluoroaryl groups, such as fluorophenyl, difluorophenyl, fluoronitrophenyl, and the like are described. For example in the case of $^{11}$C, alkyl and alkyl aryl are described.

In another aspect, the therapeutic agent is a cytotoxic compound. The cytotoxic compounds described herein operate by any of a large number of mechanisms of action. Generally, cytotoxic compounds disrupt cellular mechanisms that are important for cell survival and/or cell proliferation and/or cause apoptosis.

The drug (D) can be any therapeutic agent capable of modulating or otherwise modifying cell function, including pharmaceutically active compounds. Suitable therapeutic agents can include, but are not limited to: peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; cancer drugs including therapeutic agents.

Further, the drug (D) can be any drug known in the art which is cytotoxic, enhances tumor permeability, inhibits tumor cell proliferation, promotes apoptosis, decreases antiapoptotic activity in target cells, enhances an endogenous immune response directed to the pathogenic cells, or is useful for treating a disease state caused by any type of cancer cells. Drugs (D) suitable for use in accordance with this invention include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, taxanes, such as tamoxiphen, taxol, paclitaxel, paclitaxel derivatives, Taxotere®, and the like, maytansines and analogs and derivatives thereof, cyclophosphamide, daunomycin, doxorubicin, rhizoxin, T2 toxin, plant alkaloids, prednisone, hydroxyurea, teniposide, mitomycins, discodermolides, microtubule inhibitors, epothilones, tubulysins, and analogs and derivatives thereof, cyclopropyl benz[e]indolone, seco-cyclopropyl benz[e]indolone, O—Ac-seco-cyclopropyl benz[e]indolone, bleomycin and any other antibiotic, nitrogen mustards, nitrosureas, vinca alkaloids, vincristine, vinblastine, and analogs and derivative thereof such as deacetylvinblastine monohydrazide, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug.

Illustrative drugs and other therapeutic agents are described in U.S. Patent Application Publication Nos. US-2005-0002942-A1, US-2001-0031252-A1, and US-2003-0086900-A1. Illustrative imaging agents and diagnostic agents are described in U.S. Patent Application Publication No. US-2004-0033195-A1 and International Patent Application Publication No. WO 03/097647. The disclosures of each of the foregoing patent application publications are incorporated herein by reference.

In each of the foregoing and following embodiments, it is to be understood that the formulae include and represent not only all pharmaceutically acceptable salts of the compounds in the conjugates, but also include any and all hydrates and/or solvates of the formulae. It is appreciated that certain functional groups, such as the hydroxy, amino, and like groups form complexes and/or coordination compounds with water and/or various solvents, in the various physical forms of the compounds in the conjugates described herein. Accordingly, the formulae described herein are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and noncrystalline and/or amorphous forms of the compounds in the conjugates described herein.

Illustrative derivatives include, but are not limited to, both those derivatives that may be synthetically prepared from the B, L, and D as described herein, as well as those B, L, and D that may be prepared in a similar way as those described herein, but differing in the selection of starting materials.

It is to be understood that such derivatives may include prodrugs of the conjugates described herein and conjugates described herein that include one or more protection or protecting groups.

Illustrative analogs include, but are not limited to, the conjugates described herein that share functional and in some cases structural similarity to the conjugates described herein.

It is to be understood that each of the foregoing embodiments may be combined in chemically relevant ways to generate subsets of the embodiments described herein. Accordingly, it is to be further understood that all such subsets are also illustrative embodiments of the invention described herein.

The components of the conjugates described herein may contain one or more chiral centers, or may otherwise be capable of existing as multiple stereoisomers. It is to be understood that in one embodiment, the conjugates described herein are not limited to any particular sterochemical requirement, and may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the conjugates described herein may include geometric centers, such as cis, trans, E, and Z double bonds. It is to be understood that in another embodiment, the invention described herein is not limited to any particular geometric isomer requirement, and that the conjugates may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the conjugate and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylate and derivatives thereof" includes the group $CO_2H$ and salts thereof, and esters and amides thereof, and CN.

As used herein, the term "sulfinyl or a derivative thereof" includes $SO_2H$ and salts thereof, and esters and amides thereof.

As used herein, the term "sulfonyl or a derivative thereof" includes $SO_3H$ and salts thereof, and esters and amides thereof.

As used herein, the term "phosphinyl or a derivative thereof" includes $P(R)O_2H$ and salts thereof, and esters and amides thereof, where R is alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted.

As used herein, the term "phosphonyl or a derivative thereof" includes $PO_3H_2$ and salts thereof, and esters and amides thereof.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH heteroaryloxylNH heteroarylalkyloxylNH heteroarylalkenyloxylNH heteroarylalkynyloxylNH acyloxy, and the like, each of which is optionally substituted.

As used herein, the term "hydrazino and derivatives thereof" includes alkylNHNH, alkenylNHNH, alkynylNHNH, heteroalkylNHNH, heteroalkenylNHNH, heteroalkynylNHNH, cycloalkylNHNH, cycloalkenylNHNH, cycloheteroalkylNHNH, cycloheteroalkenylNHNH, arylNHNH, arylalkylNHNH, arylalkenylNHNH, arylalkynylNHNH, heteroarylNHNH, heteroarylalkylNHNH, heteroarylalkenylNHNH, heteroarylalkynylNHNH, acylNHNH, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical $-(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, $(C_1-C_6$ alkyl)$(C_1-C_6$ alkyl)amino, alkylcarbonylamino, N—$(C_1-C_6$ alkyl)alkylcarbonylamino, aminoalkyl, $C_1-C_6$ alkylaminoalkyl, $(C_1-C_6$ alkyl)$(C_1-C_6$ alkyl)aminoalkyl, alkylcarbonylaminoalkyl, N—$(C_1-C_6$ alkyl)alkylcarbonylaminoalkyl, cyano, and nitro; or $Z^X$ is selected from —$CO_2R^4$ and —$CONR^5R^6$, where $R^4$, $R^5$, and $R^6$ are each independently selected in each occurrence from hydrogen, $C_1-C_6$ alkyl, aryl-$C_1-C_6$ alkyl, and heteroaryl-$C_1-C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the conjugates described herein by attaching groups that ultimately cleave in vivo to one or more functional groups present on the conjugate, such as —OH—, —SH, —$CO_2H$, —$NR_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the conjugates described herein. Further illustrative prodrugs for amino groups include, but are not limited to, $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl$(C_2-C_{16})$alkanoyl; optionally substituted aroyl, such as unsubstituted aroyl or aroyl substituted by 1 to 3 substituents selected from the group consisting of halogen, cyano, trifluoromethanesulphonyloxy, $(C_1-C_3)$alkyl and $(C_1-C_3)$alkoxy, each of which is optionally further substituted with one or more of 1 to 3 halogen atoms; optionally substituted aryl$(C_2-C_{16})$alkanoyl and optionally substituted heteroaryl$(C_2-C_{16})$alkanoyl, such as the aryl or heteroaryl radical being unsubstituted or substituted by 1 to 3 substituents selected from the group consisting of halogen, $(C_1-C_3)$alkyl and $(C_1-C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the conjugate described herein that is biologically active or is a precursor of the biologically active conjugate. However, it is appreciated that in some cases, the prodrug is biologically active. It is also appreciated that prodrugs may often serve to improve drug efficacy or safety through improved oral bioavailability, pharmacodynamic half-life, and the like. Prodrugs also refer to derivatives of the compounds described herein that include groups that simply mask undesirable drug properties or improve drug delivery. It is appreciated herein that a prodrug, or other strategy using reversible derivatives, can be useful in the optimization of the clinical application of a drug.

It is to be understood that the embodiments described herein may be combined in all possible chemically relevant ways.

The term "imaging effective amount" as used herein, refers to that amount of conjugate that allows the imaging of cancer cells, tumor, or cancer cell containing tissue present in an animal or human.

The term "therapeutically effective amount" as used herein, refers to that amount of active conjugate that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the conjugates described herein may be decided by the attending physician within the scope of sound medical judgment. The specific therapeutically-effective dose level for any particular patient will depend upon a variety of factors, including the disorder being treated and the severity of the disorder; activity of the specific conjugate employed; the specific composition employed; the age, body weight, general health, gender and diet of the patient: the time of administration, route of administration, and rate of excretion of the specific conjugate employed; the duration of the treatment; drugs used in combination or coincidentally with the specific conjugate employed; and like factors well known to the researcher, veterinarian, medical doctor or other clinician of ordinary skill It is also appreciated that the therapeutically effective amount may be reduced with a combination therapy. Further, it is appreciated that the co-therapies described herein may allow for the administration of lower doses of conjugates than would otherwise be administered in the absence of a cotherapy.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated conjugates described herein or from salts, solutions, hydrates, solvates, and other forms of the conjugates described herein. It is also to be understood that the compositions may be prepared from various amorphous, non-amorphous, partially crystalline, crystalline, and/or other morphological forms of the conjugates described herein. It is also to be understood that the compositions may be prepared from various hydrates and/or solvates of the conjugates described herein. Accordingly, such pharmaceutical compositions that recite conjugates described herein are to be understood to include each of, or any combination of, the various morphological forms and/or solvate or hydrate forms of the conjugates described herein. Illustratively, compositions may include one or more carriers, diluents, and/or excipients. The conjugates described herein, or compositions containing them, may be formulated in a therapeutically effective amount in any conventional dosage forms appropriate for the methods described herein. The conjugates described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

The term "administering" as used herein includes all means of introducing the conjugates and compositions described herein to the patient, including, but not limited to intravenous (iv), intramuscular (im), subcutaneous (sc), transdermal, and the like. The conjugates and compositions described herein may be administered in unit dosage forms and/or formulations containing conventional nontoxic pharmaceutically-acceptable carriers, adjuvants, and vehicles.

Illustratively, administering includes local use, such as when administered locally to the site of disease. Illustrative local administration may be performed during open surgery, or other procedures when the site of disease is accessible. Alternatively, local administration may be performed using parenteral delivery where the conjugate or compositions described herein are deposited locally to the site without general distribution to multiple other non-target sites in the patient being treated. It is further appreciated that local administration may be directly in the disease site, or locally in the surrounding tissue. Similar variations regarding local delivery to particular tissue types, such as organs, and the like, are also described herein. Illustratively, conjugates may be administered intracerebral, intraventricular, intracerebroventricular, intrathecal, intracisternal, intraspinal and/or peri-spinal routes of administration by delivery via intracranial or intravertebral needles and/or catheters with or without pump devices.

Illustrative routes for parenteral administration include intravenous, intraarterial, intraperitoneal, epidurial, intraurethral, intrasternal, intramuscular and subcutaneous, as well as any other art recognized route of parenteral administration. Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates, alcohols, and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the conjugate incorporated into liposomes. In cases where the conjugate in itself is not sufficiently soluble to be dissolved, a solubilizer such as ethanol can be applied.

The dosage of each conjugate of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

In addition to the foregoing illustrative dosages and dosing protocols, it is to be understood that an effective amount of any one or a mixture of the conjugates described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including a human patient, its size, age, and general health, the specific disease or disorder involved, the degree of or involvement or the severity of the disease or disorder, the response of the individual patient, the particular conjugate administered, the mode of administration, the bioavailability characteristics of the preparation administered, the dose regimen selected, the use of concomitant medication, and other relevant circumstances.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier, or medium for the active ingredient. Thus, the formulation compositions can be in the form of suspensions, emulsions, solutions, sterile injectable solutions, and sterile packaged powders. The compositions may contain anywhere from about 0.1% to about 99.9% active ingredients, depending upon the selected dose and dosage form.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (generally regarded as safe) compounds.

Examples of emulsifying agents are naturally-occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol, and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE. Examples of chelating agents are sodium EDTA, citric acid, and phosphoric acid. Examples of gel forming agents are CARBOPOL, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN)).

Parenteral Compositions. The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active conjugate(s), the composition may include suitable parenterally acceptable carriers and/or excipients. The active conjugate(s) may be incorporated into micro spheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions described herein may be in the form suitable for sterile injection. To prepare such a composition, the suitable active conjugate(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the components of the composition is only sparingly or slightly soluble in water, a dissolution enhancing or solubilizing agent can be added, or the solvent may include 10-60% w/w of propylene glycol or the like.

Controlled Release Parenteral Compositions. Controlled release parenteral compositions may be in form of aqueous suspensions, microspheres, microcapsules, magnetic microspheres, oil solutions, oil suspensions, or emulsions. Alternatively, the active conjugates(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), or lipoproteins. Materials for use in implants can be non-biodegradable (e.g., polydimethyl siloxane) or biodegradable (e.g., poly(caprolactone), poly(lactic acid), poly (glycolic acid) or poly(ortho esters)).

Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between about 2 to about 9, and more preferably about 4 to about 8. As such the buffering agent may be as much as about 5% by weight of the total composition.

Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. Such agents may be present in amounts as needed, such as from about 0.001 to about 5% by weight, or from about 0.01 to about 2% by weight.

The following examples further illustrate specific embodiments of the invention; however, the following illustrative examples should not be interpreted in any way to limit the invention.

During an analysis of various folate analogs and derivatives, it was discovered that dimethyltetrahydrofolate (DMTHF) appeared to bind preferentially to FR-α. A radiolabeled ($^{99m}$Tc)-chelate complex of DMTHF ($^{99m}$Tc-DMTHF-chelate) was prepared; see Scheme 1. Its affinity for cells expressing FR-α versus FR-β was measured and compared to a $^{99m}$Tc complex of a folate-chelate conjugate (EC20-$^{99m}$Tc). For evaluation of its affinity for FR-α, increasing concentrations of $^{99m}$Tc-DMTHF-chelate were incubated with KB cells, a human nasopharyngeal cancer cell line known to over-express FR-α. The level of bound radioactivity was analyzed using a gamma counter. As shown in FIG. 1, $^{99m}$Tc-DMTHF-chelate associated with KB cells with an apparent $K_d$ of 38 nM in a manner that was quantitatively inhibited by 100-fold molar excess of free folic acid. Parallel binding studies with EC20 (a $^{99m}$Tc chelating agent targeted with folic acid) yielded a $K_d$ of 23 nM that was also competed by excess free folic acid.

Because FR-β expressing monocytes and macrophages constitute only a small fraction of the total cell population in any tissue, they are difficult to isolate for direct binding studies. Therefore, two DMTHF-dye conjugates (Scheme 2) were employed in conjunction with macrophage markers to assess the binding of DMTHF to FR-β+ macrophages in a heterogeneous cell suspension by flow cytometry. As seen in

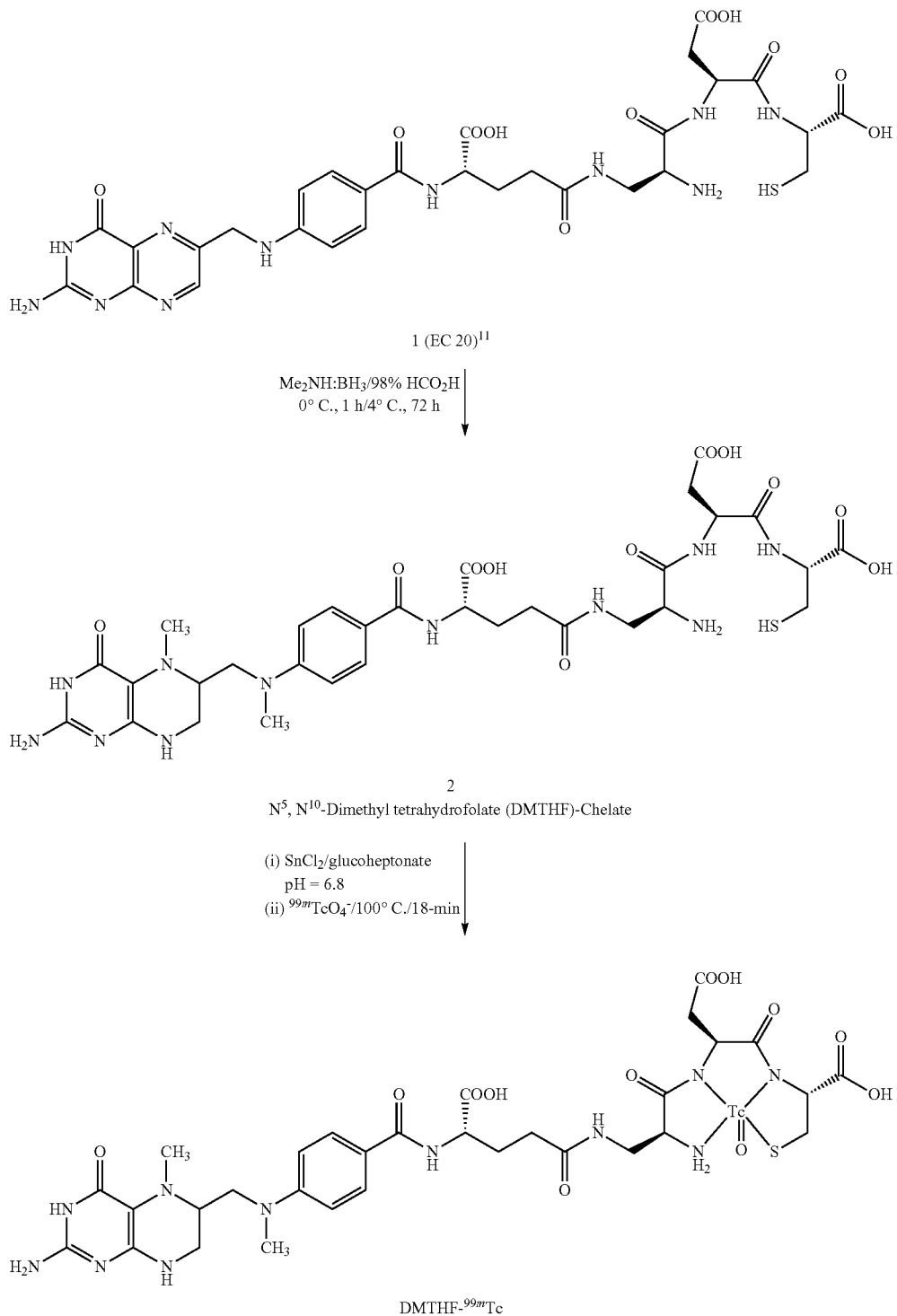

Figures 1, 12:
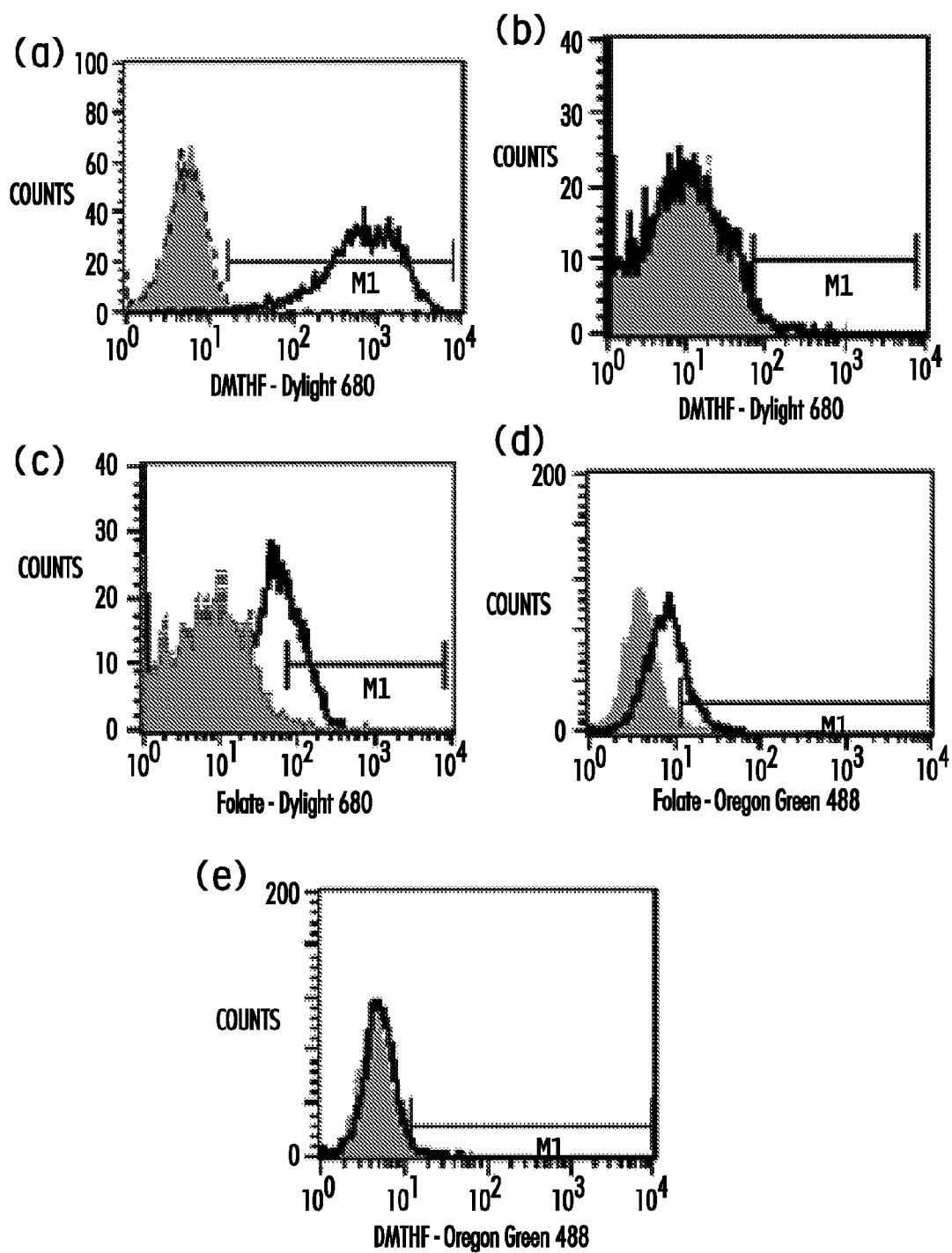
Figures 2, 12:
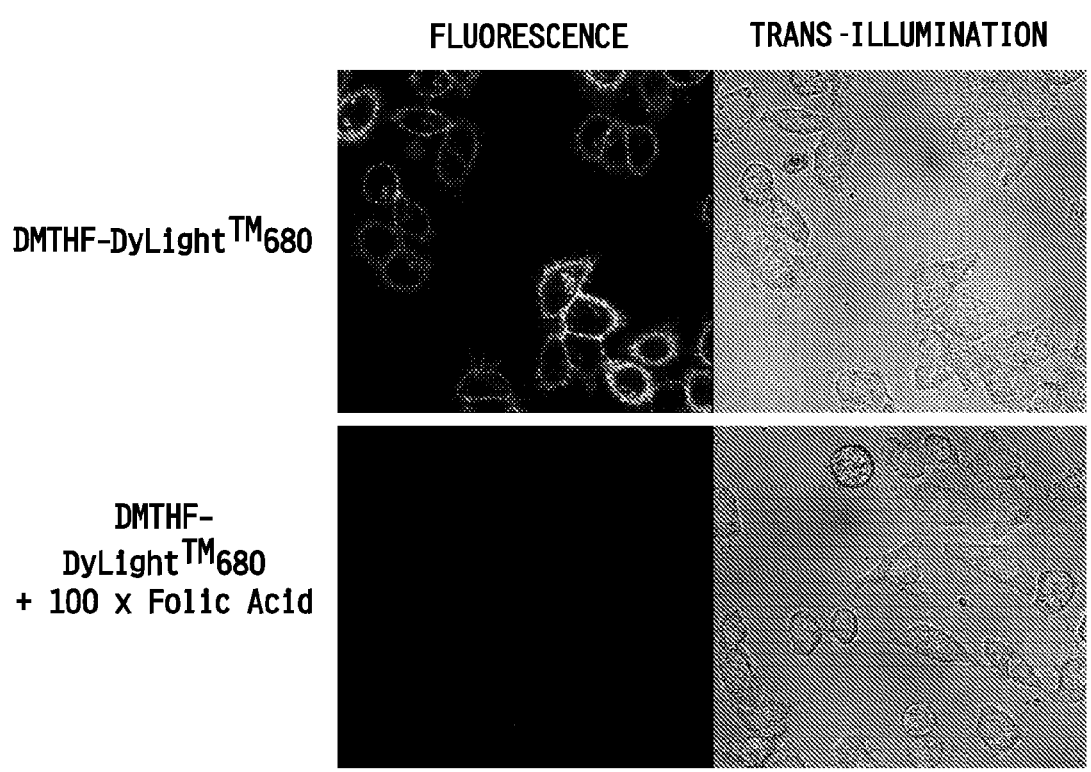

FIG. 12-1(a), DMTHF-DyLight 680 conjugate binds avidly to FR-α+ human KB cells, a demonstrating that the conjugate exhibits the expected affinity for the alpha isoform of FR. In contrast, DMTHF-DyLight 680 shows no measurable affinity for CD 11b+ rat peritoneal macrophages, even though the same cell population binds aggressively and avidly to folate-DyLight 680 (FIG. 12-1(b) and 12-1(c), respectively). These data demonstrate that DMTHF binds FR-α, but displays little affinity for FR-β.

To confirm FR-α selectivity with human peripheral blood monocytes, a DMTHF-Oregon Green conjugate was synthesized in order to allow simultaneous labeling with the human monocyte marker, anti-human CD11b (Tricolor labeled). Adding a folate-Oregon Green conjugate caused a shift in the CD11b+ subpopulation of human peripheral blood leucocytes, whereas DMTHF-Oregon Green did not (FIG. 12-1(d) and 12-1(e)), corroborating the lack of affinity of DMTHF for FR-β expressing myeloid cells.

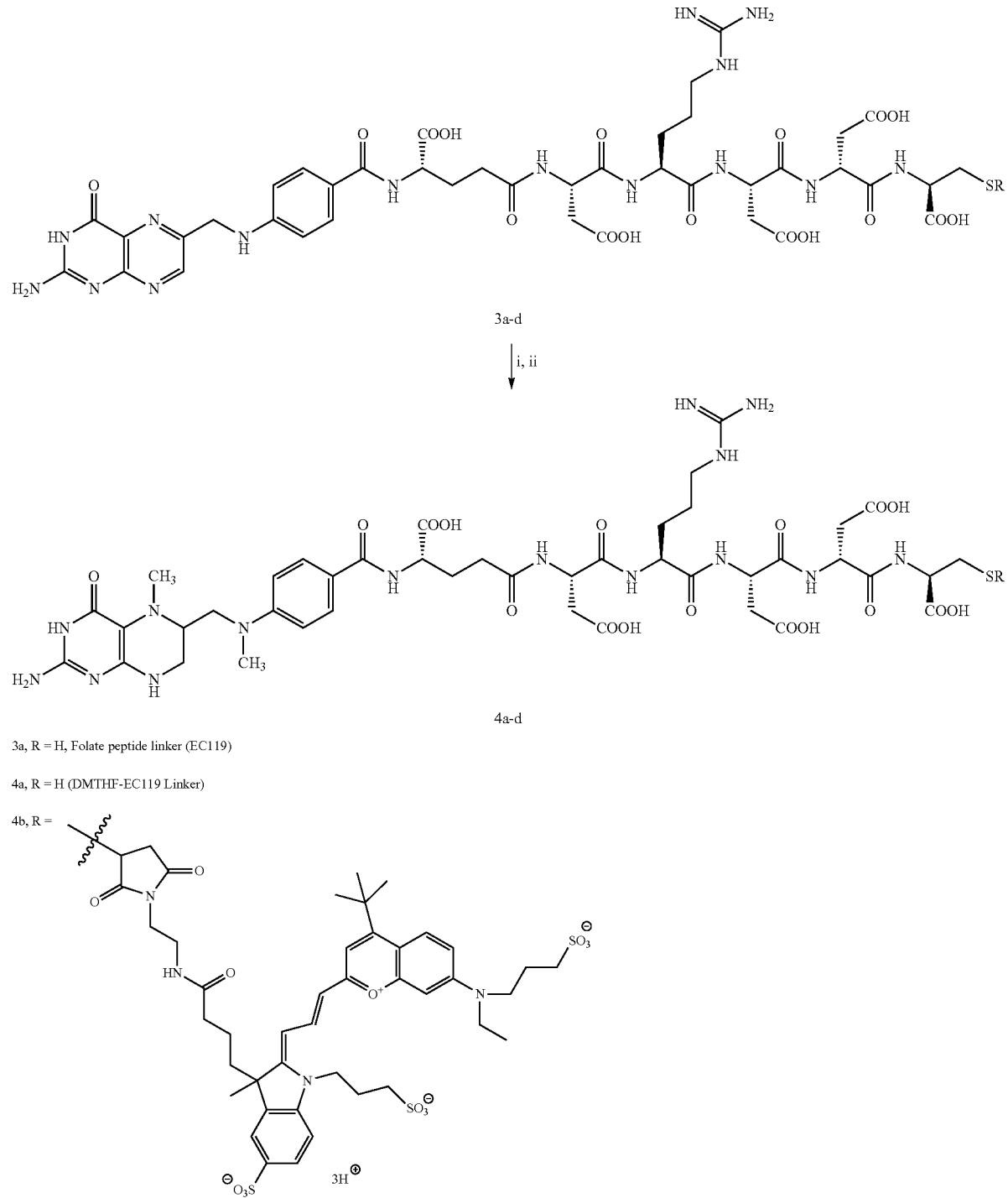

Scheme 2

3a-d i, ii 4a-d

3a, R = H, Folate peptide linker (EC119)

4a, R = H (DMTHF-EC119 Linker)

4b, R =

4c, R = 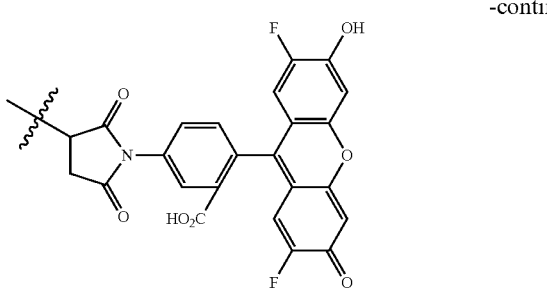

4d, R = 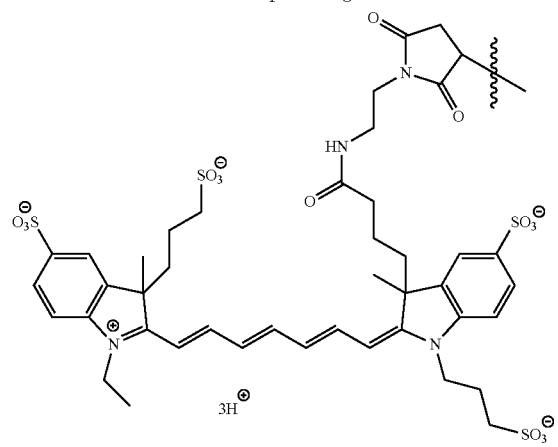

Reagents and conditions: i) (a) BH$_3$.NMe$_2$, 98% HCO$_2$H, 0° C., 1 h, stir (b) 4° C., 72 h, dark; ii) Dylight™ 680 maleimide or Oregon Green™ 488 maleimide, or Dylight 750 maleimide, DIPEA/DMSO.

Figure 3:
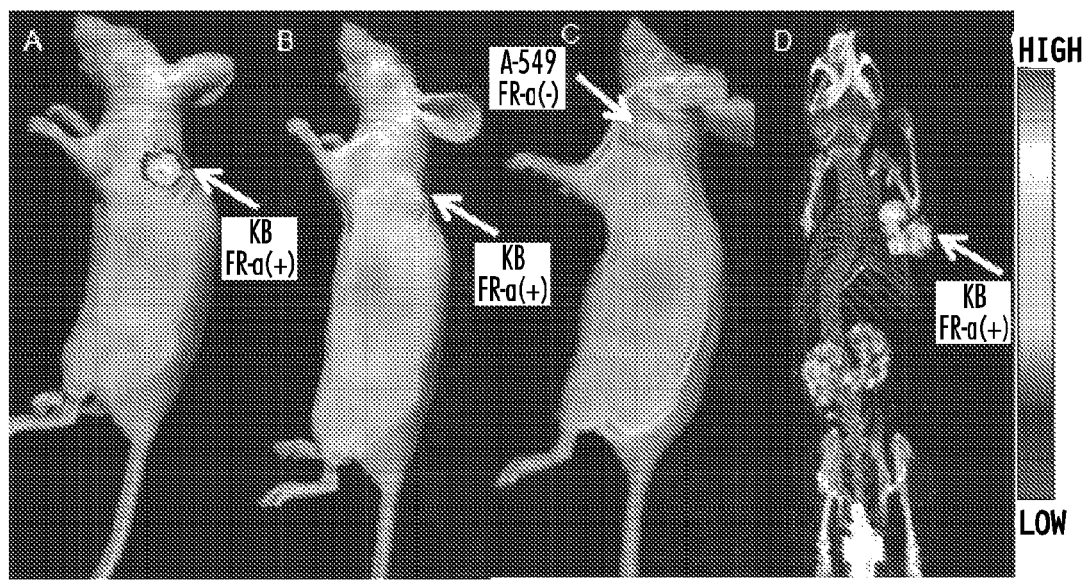
FIG. 3 Shows an overlay of whole body $N^5,N^{10}$-dimethyltetrahydrofolic acid-$^{99m}$Tc conjugate (DMTHF-$^{99m}$Tc) radioimages on white light images of nu/nu mice bearing (A) FR-α positive KB tumor, (B) FR-α positive KB tumor pretreated with excess folic acid to block all FR, and (C) FR-α negative A549 tumor. In images A-C, radio-emissions from the kidneys were blocked to permit easier visualization of conjugate distribution in other tissues. In the SPECT/CT image of the KB tumor-bearing nu/nu mouse in panel D, DMTHF-$^{99m}$Tc (11 MBq or 300 μCi) was injected 2 h prior to imaging on a MiLabs U-SPECT-II.

To evaluate the specificity of DMTHF for FR-α expressing tumors in vivo, we implanted both KB (FR-α$^+$) and A549 (FR-α$^-$) tumor xenografts on the shoulders of athymic nu/nu mice and examined the uptake of DMTHF-$^{99m}$Tc in both tumor models. As shown in FIG. 3, the DMTHF ligand displays excellent specificity for KB tumor (FR-α$^+$) but no affinity for A-549 tumor (FR-α$^-$) [panel (A) and panel (C) respectively].

Figure 4:
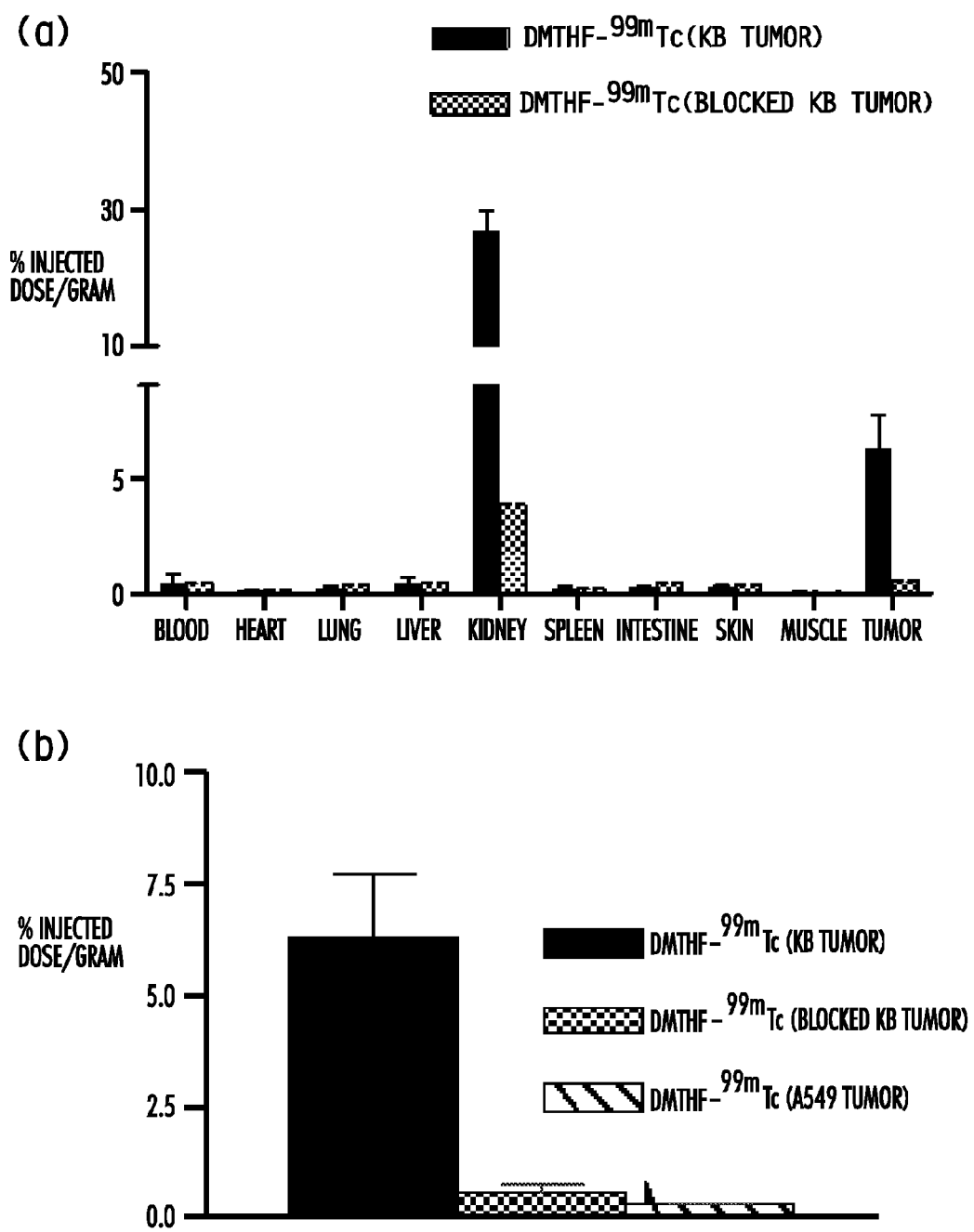
FIG. 4. Panel (a) shows the results of a biodistribution study of DMTHF-$^{99m}$Tc chelate conjugate in nu/nu mice bearing KB tumors in the presence and absence of excess folic acid. Error bars represent SD (n=5 mice/group). Panel (b) Shows a comparison of tumor uptake of DMTHF-$^{99m}$Tc in nu/nu mice bearing KB, tumor uptake of DMTHF-$^{99m}$Tc in nu/nu mice bearing KB with co-administered excess folic acid, and A-549 tumors. Error bars represent SD (n=4 mice/group).

The FR-α specificity of DMTHF-$^{99m}$Tc is further confirmed by pre-injection of excess folic acid to block all of the folate receptors in tumor tissue prior to DMTHF-$^{99m}$Tc administration. Blocked KB tumor (FR-α$^+$) failed to show any uptake of DMTHF-$^{99m}$Tc thereby demonstrating the in vivo specificity of the new ligand [FIG. 3, panel (B)]. Quantitative confirmation of this specificity was further provided by the biodistribution studies, where competitive binding was seen in the FR$^+$ tumor (FIG. 4(a)) but no significant binding was detected in the FR$^-$ tumor (FIG. 4(b)).

Only the tumor and kidneys showed high levels of accumulation of the radiotracer in mice with KB tumors. The percent injected dose per gram of wet tissue (% ID/g) for tumor and kidneys were 6 and 22, respectively. Other organs had significantly lower uptake with less than 1% ID/g yielding excellent tumor to non-tumor tissue ratios; e.g. 72:1 (tumor to muscle), 50:1 (tumor to heart), 14:1 (tumor to liver), 25:1 (tumor to spleen).

Several inflammatory animal models were examined demonstrating the receptor selectivity of DMTHF-$^{99m}$Tc for FR-α over FR-β. In each of the inflammatory animal model experiments, an equal dose of EC20-$^{99m}$Tc was administered to another group of mice as a positive control for comparison. EC20-$^{99m}$Tc bind to both FR-α and FR-β.

Figure 5:
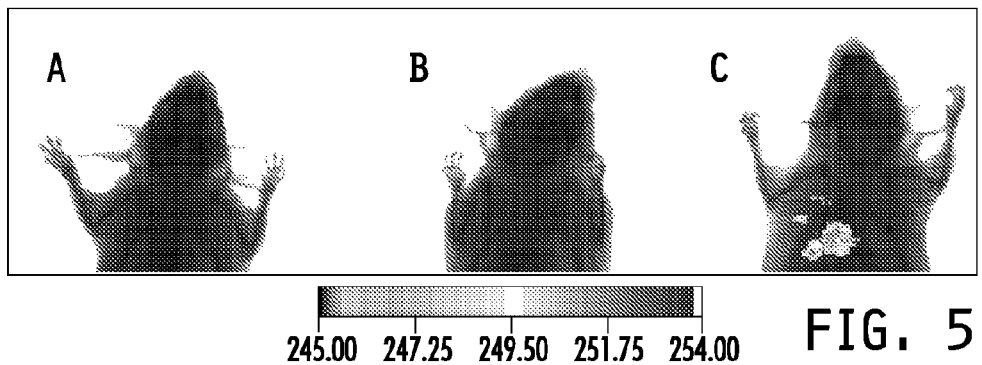
FIG. 5. Radio imaging of EC20-$^{99m}$Tc and DMTHF-$^{99m}$Tc in atherosclerotic ApoE$^{-/-}$ mice fed a western diet for 25 weeks and then injected with (A) 50 nmol/kg DMTHF-$^{99m}$Tc, (B) 250 nmol/kg DMTHF-$^{99m}$Tc, and (C) 50 nmol/kg EC20-$^{99m}$Tc in their respective groups. Radio images were obtained on a Kodak Imaging Station.
Figure 6:
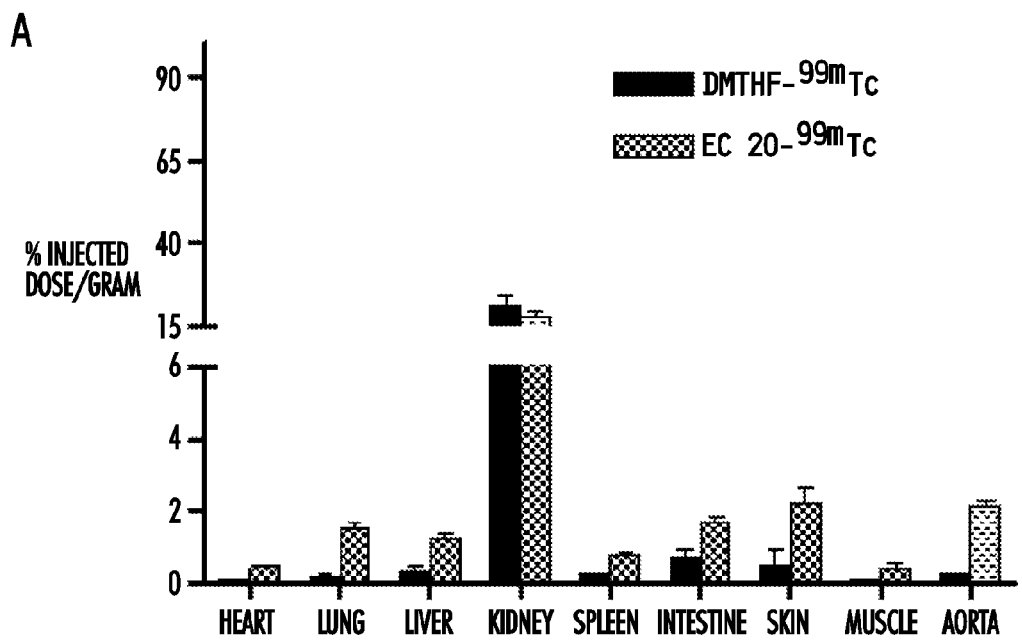
FIG. 6 Panel A. Biodistribution studies of ApoE$^{-/-}$ atherosclerotic mice injected with EC20-$^{99m}$Tc, DMTHF-$^{99m}$Tc and 5× molar DMTHF-$^{99m}$Tc (5×) (n=5). Panel B. Statistical analysis presented as p-values<0.05.
Figure 6:
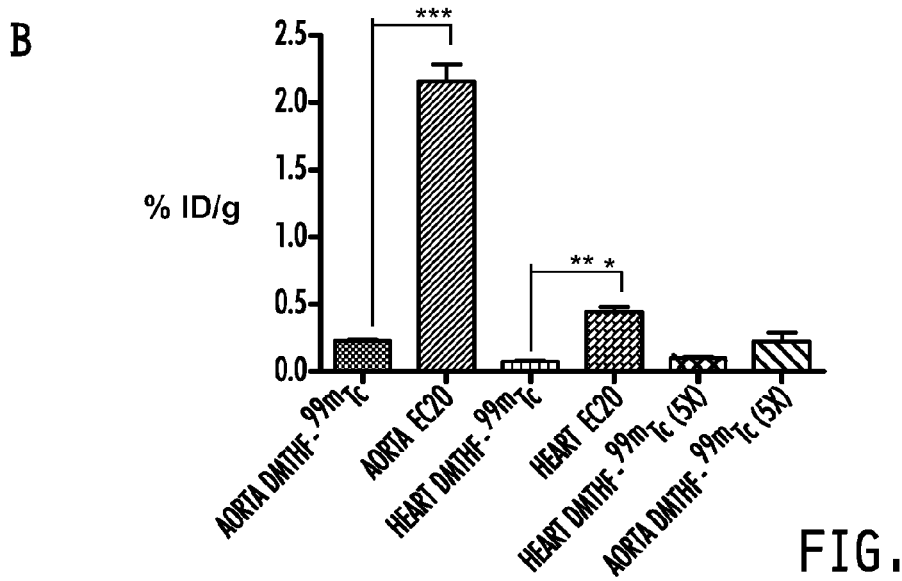

In an atherosclerosis model, ApoE−/− mice fed a high fat diet were treated with DMTHF-$^{99m}$Tc and, 4 h post-injection, radio-imaged in a Kodak Imaging Station. It was observed that mice injected with EC20-$^{99m}$Tc (positive control) had significant uptake of the EC20-$^{99m}$Tc in the aorta-cardiac region (see FIG. 5C) whereas similarly fed mice injected with DMTHF-$^{99m}$Tc displayed negligible uptake of the radiotracer (see FIGS. 5A and 5B). The absence of signal intensity in the mice treated with DMTHF-$^{99m}$Tc demonstrates the lower affinity of the radiotracer towards the FR-β expressed by the activated macrophages present in the aortic plaques. In addition, biodistribution studies revealed a statistically low % ID/g ratio of DMTHF-$^{99m}$Tc to EC20-$^{99m}$Tc radiotracer in the aorta (1:10) and the heart (1:6) as shown in Panel B of FIG. 6.

Figure 7:
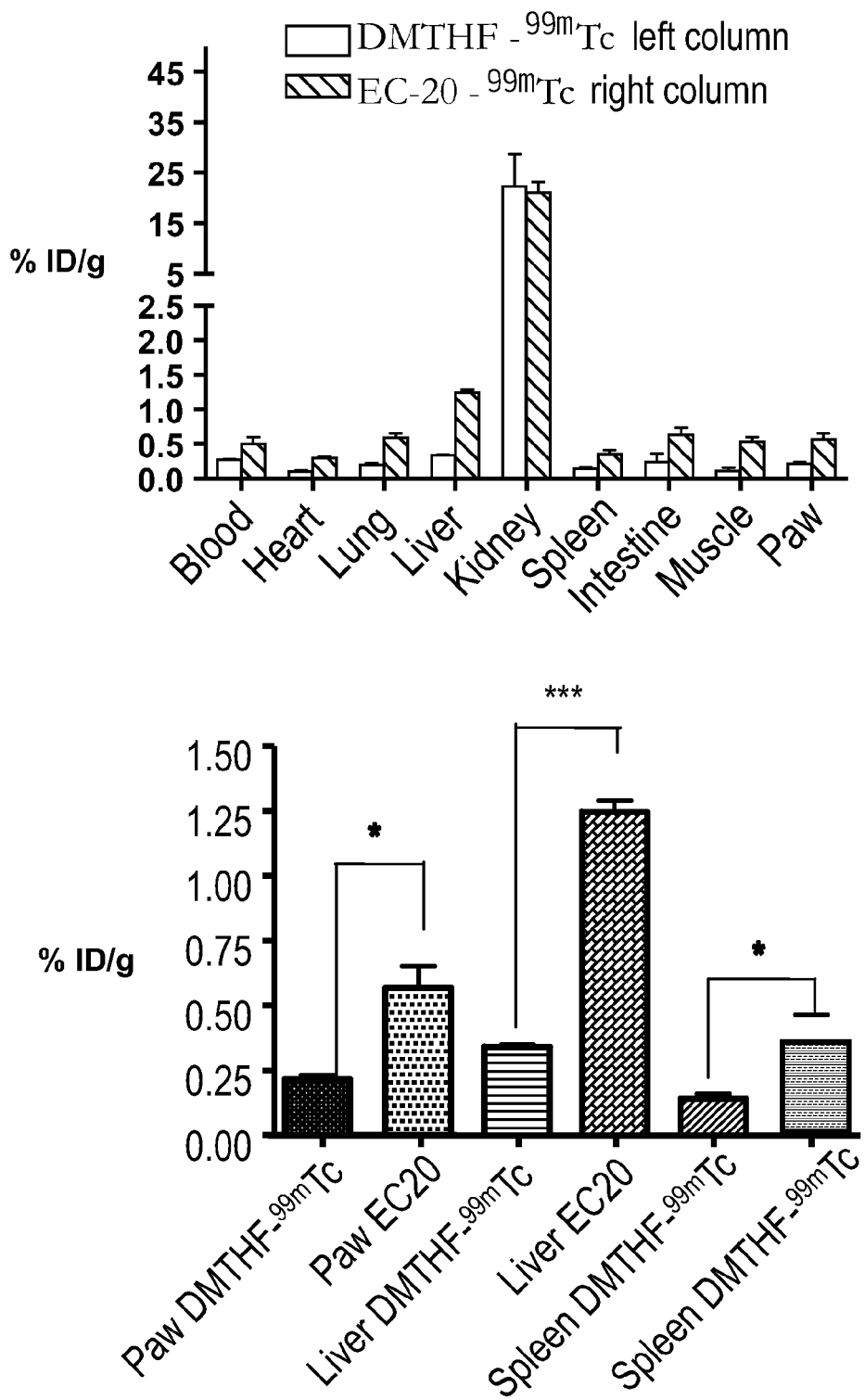
FIG. 7 Panel A. Biodistribution studies of EC20-$^{99m}$Tc and DMTHF-$^{99m}$Tc in DBA/1J mice with collagen induced arthritis. Panel B. Statistical analysis p-values<0.05

To further assess the folate receptor alpha in vivo selectivity of DMTHF-$^{99m}$Tc, male DBA/1 LacJ mice were induced to develop experimental autoimmune arthritis using the well-known procedure for collagen induced arthritis (CIA). After seven days of induction of the disease, the experimental animals were imaged after treatment with DMTHF-$^{99m}$Tc or EC20-$^{99m}$Tc (positive control). Systemic inflammation of liver and spleen as well as the joints allowed the accumulation of EC20-$^{99m}$Tc in the inflamed tissues, whereas the uptake of DMTHF-$^{99m}$Tc in these tissues was lower (see FIG. 7, Panels A and B). These data further support the lower affinity of DMTHF-$^{99m}$Tc at the sites of inflammation.

Figure 8:
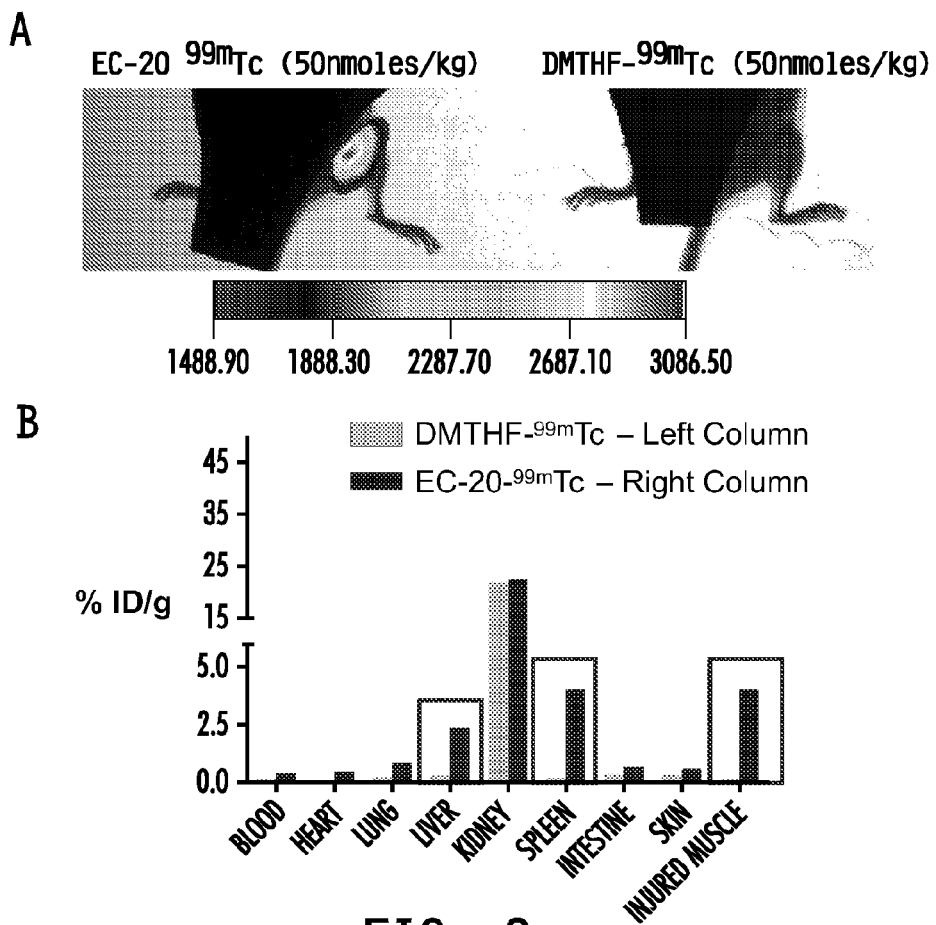
FIG. 8 Panel A. Radio imaging after administering EC20-$^{99m}$Tc or DMTHF-$^{99m}$Tc (50 nmol/kg) of C57BL/6J mice with muscle injury induced by cardiotoxin - - - . Radio images were obtained on a Kodak Imaging Station (n=5). Panel B. Biodistribution studies of EC20-$^{99m}$Tc and DMTHF-$^{99m}$Tc treated C57BL/6J mice with muscle injury.
Figures 1, 8:
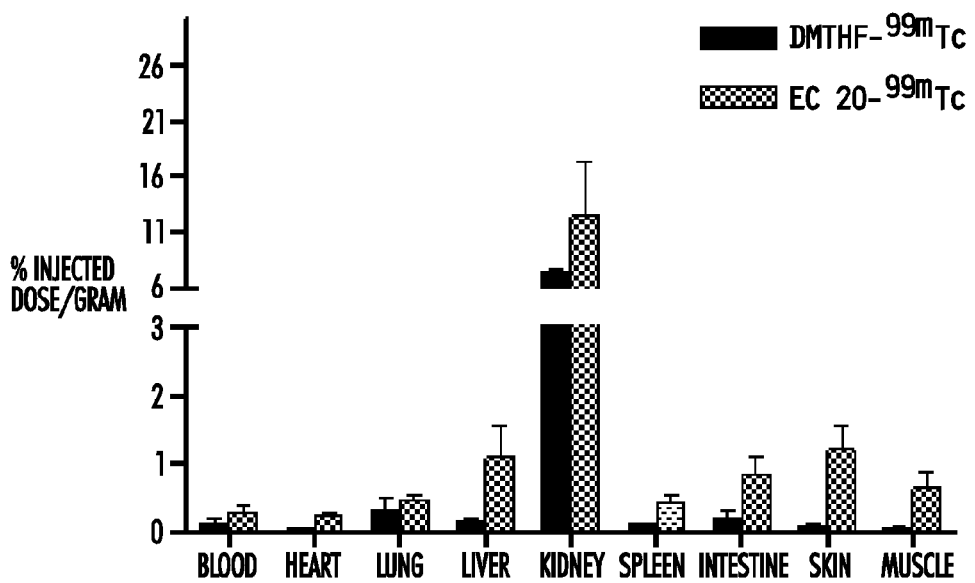

Muscle injury is another animal model for inflammatory diseases that enables visualization of the involvement of activated macrophages in muscle repair and myogenesis. Muscle injury was induced by injection of cardiotoxin at the tibia region of the hind leg of C57BL6J mice. After a three day induction period, the mice were treated with DMTHF-$^{99m}$Tc or EC20-$^{99m}$Tc. As shown in Panel A of FIG. 8, only the mice treated with EC-20-$^{99m}$Tc show an appreciable uptake in the injured muscle and little uptake was observed in DMTHF-$^{99m}$Tc treated mice. The difference in uptake of the two conjugates is evident in the biodistribution data shown in Panel B of FIG. 8.

Figure 9:
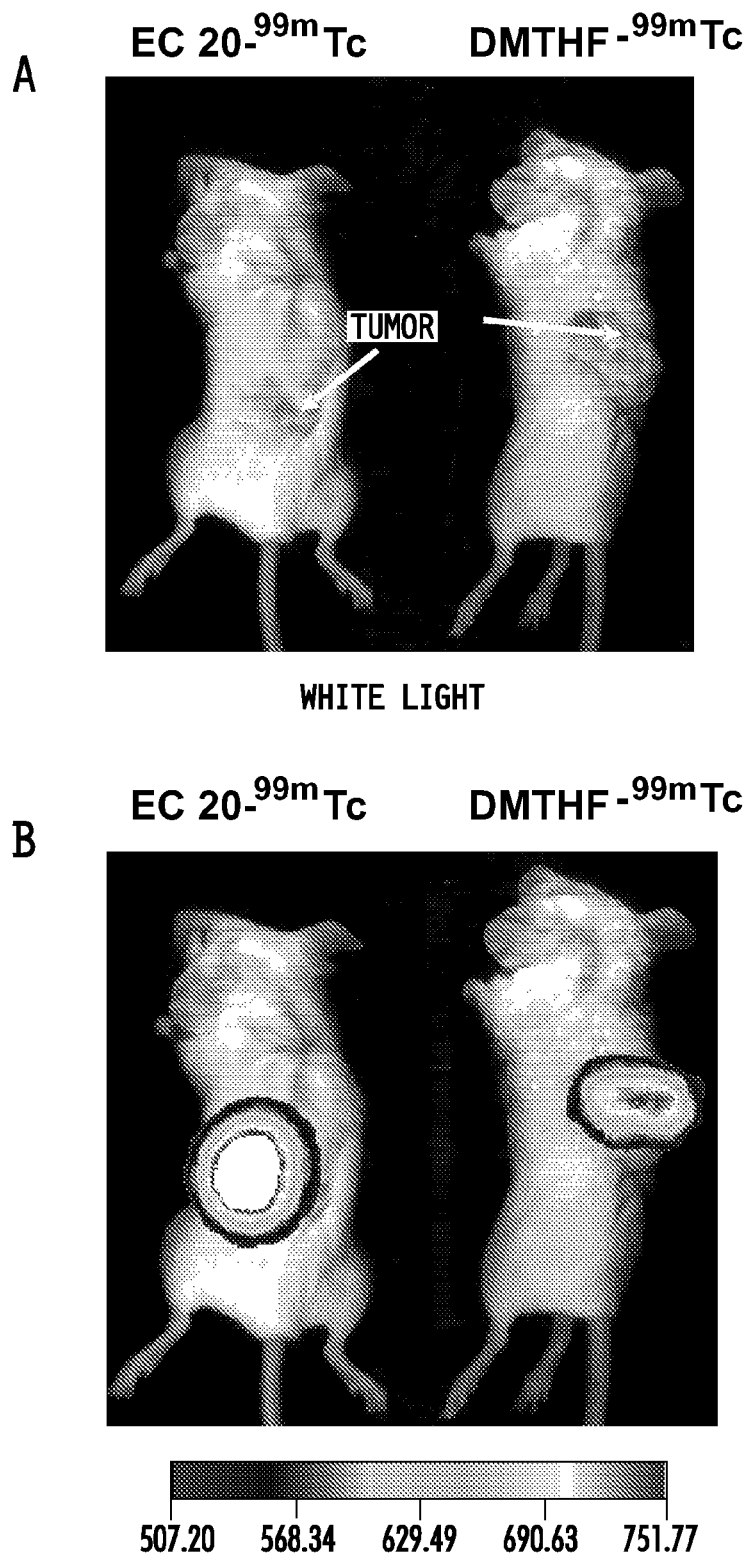
FIG. 9 Panel A) White light images of Balb/c mice bearing M109 tumors and induced ulcerative colitis. Panel B an overlay of whole body radioimages on white light images of Balb/c mice bearing M109 tumors and induced ulcerative colitis 4 hours after administration of 50 nmol/kg of EC20-$^{99m}$Tc or DMTHF-$^{99m}$Tc, 4 h.
Figure 10:
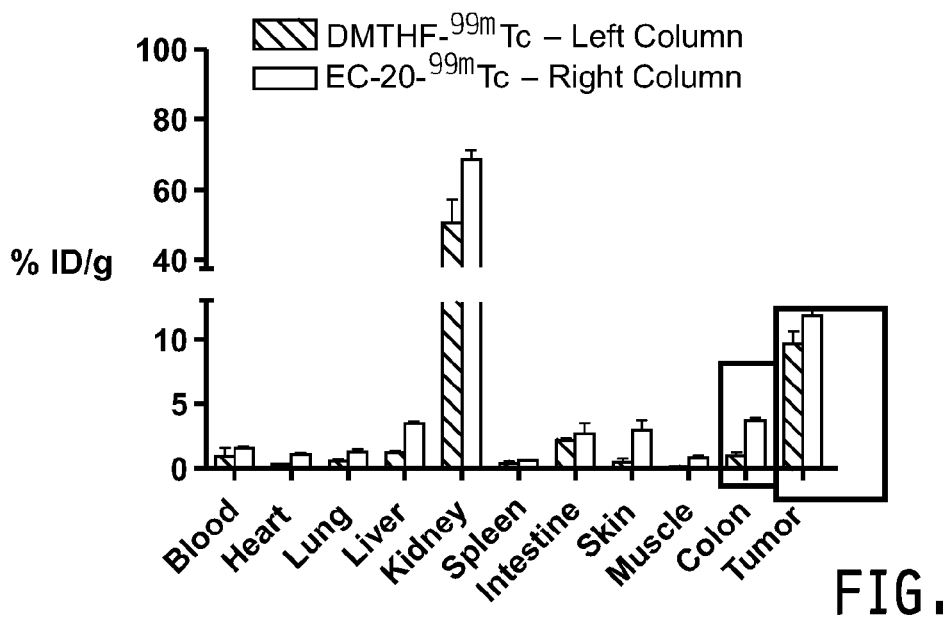
FIG. 10 Biodistribution studies of EC20-$^{99m}$Tc and DMTHF-$^{99m}$Tc treated Balb/C mice with M109 tumor and DSS induced ulcerative colitis.
Figure 11:
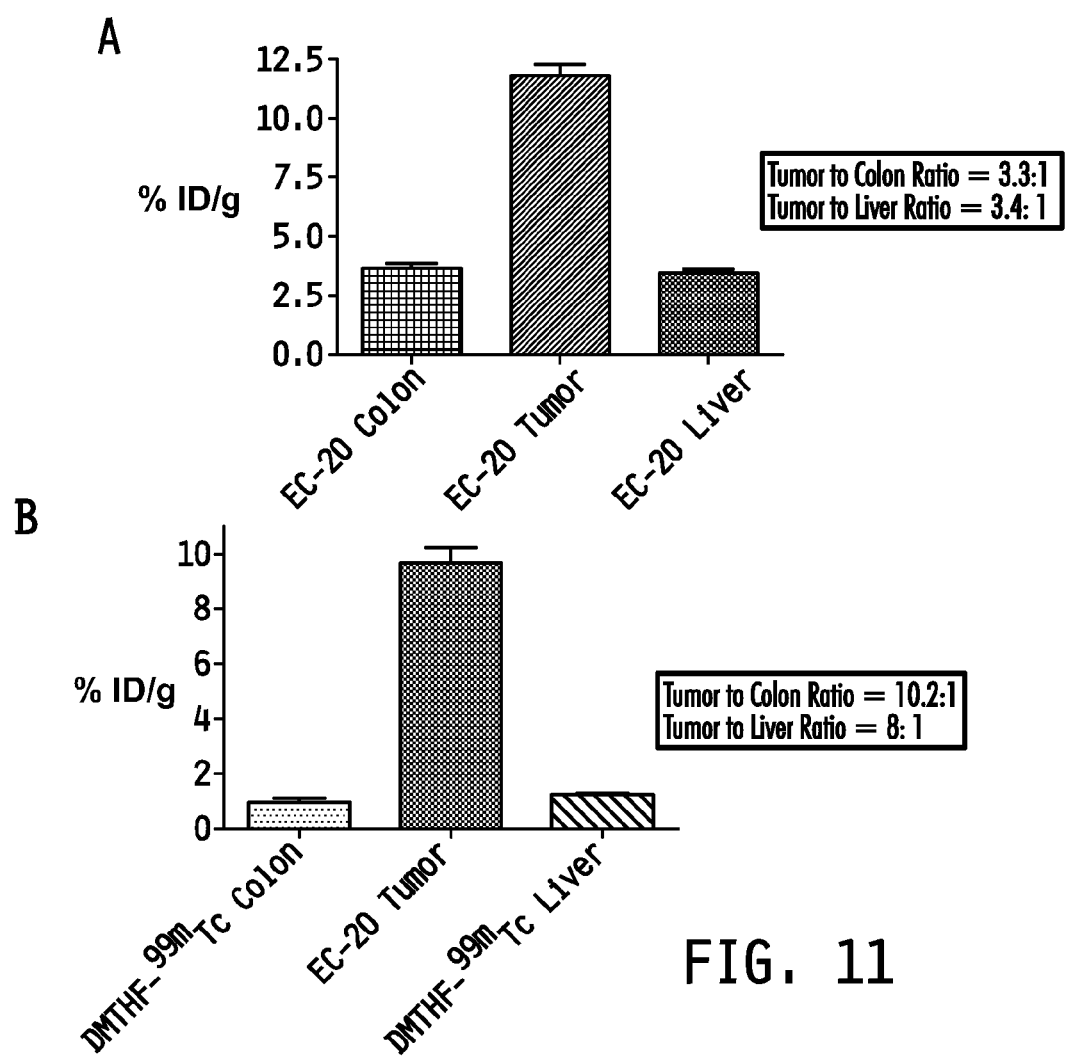
FIG. 11 Panel A. Tumor to non-tumor ratios of EC20-$^{99m}$Tc treated Balb/C mice with M109 tumor and DSS induced ulcerative colitis (tumor:colon—3.3:1 and tumor:liver—3.4:1). Panel B. Tumor to non-tumor ratios of DMTHF-$^{99m}$Tc treated Balb/C mice with M109 tumor and DSS induced ulcerative colitis (tumor:colon—10.2:1 and tumor:liver—8:1).

The in vivo efficacy and specificity of the DMTHF-$^{99m}$Tc conjugate was further evaluated in male Balb/C mice bearing FR-α M109 tumor xenografts along with FR-β expressing ulcerative colitis. As shown in Panel B of FIG. 9 and in FIG. 10, tumor uptake of DMTHF-$^{99m}$Tc was comparable to the uptake of EC20-$^{99m}$Tc in M109 tumors, but there was a significant difference in uptake of EC20-$^{99m}$Tc in the colon tissues. It is believed that this difference in uptake is due to the weaker affinity of DMTHF-$^{99m}$Tc towards FR-β receptors that is clearly evident from biodistribution data (see FIG. 10). The percent injected dose per gram of wet tissue (% ID/g) for tumor to colon ratio for DMTHF-$^{99m}$Tc was found to be 10.2:1, whereas EC20-$^{99m}$Tc had a tumor to colon ratio of 3.3:1. These data support that EC20-$^{99m}$Tc binds to both tumor tissue and sites of inflammation, whereas the DMTHF-$^{99m}$Tc is concentrated in tumor tissue.

Figure 2:
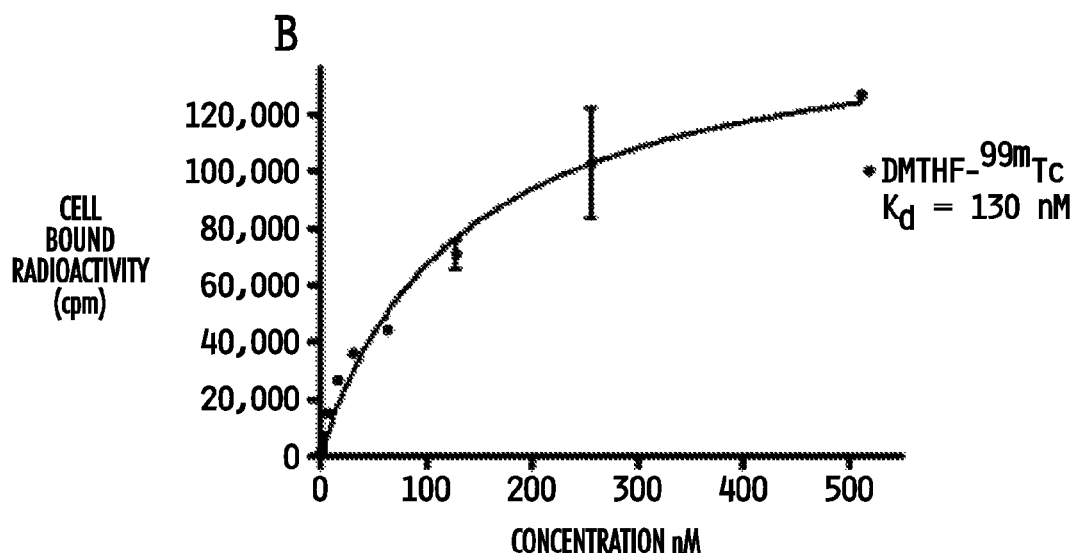
FIG. 2 Binding affinity of (B) DMTHF-$^{99m}$Tc for FR-β positive CHO-13 cells - - - ; (D) EC20-$^{99m}$Tc for FR-β positive CHO-13 cells; error bars SD (n=2).
Figure 2:
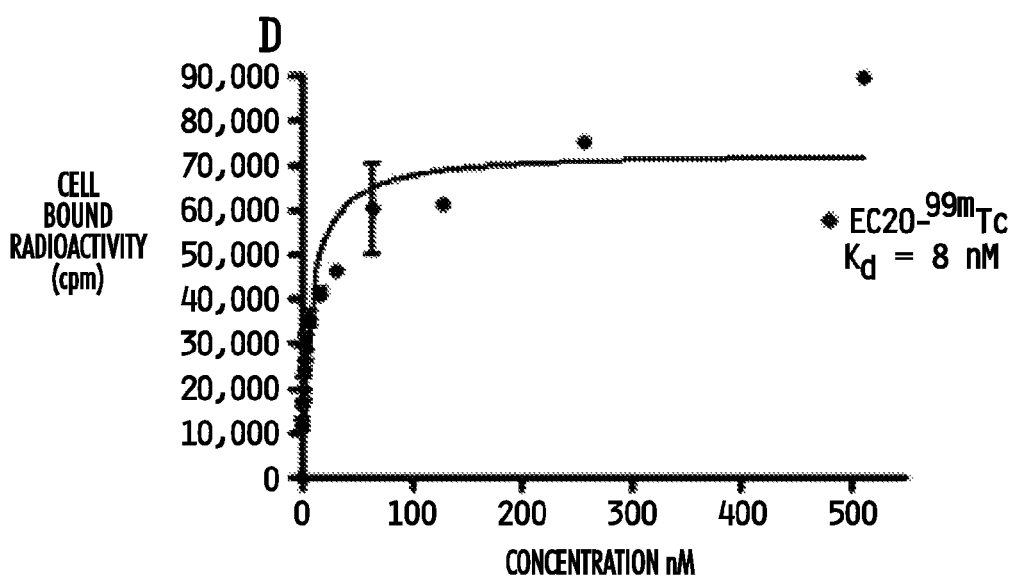
Figure 13:
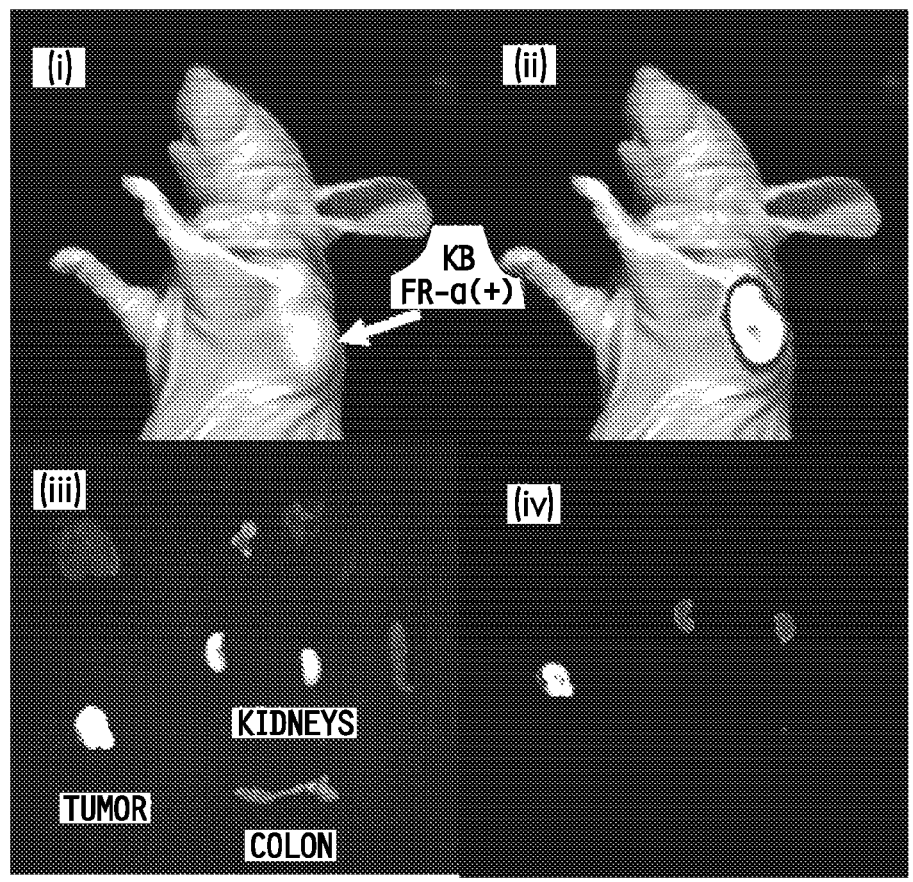
FIG. 13 Overlay of fluorescent image (ii) with white light image (i) of nu/nu mice bearing KB tumors, 4 h after administration of DMTHF-Dylight™ 680, (iii) White light images of regions of interest (ROI) of different tissues/organs and (iv) fluorescent image of ROI of different tissues/organs.
Figures 1, 14:
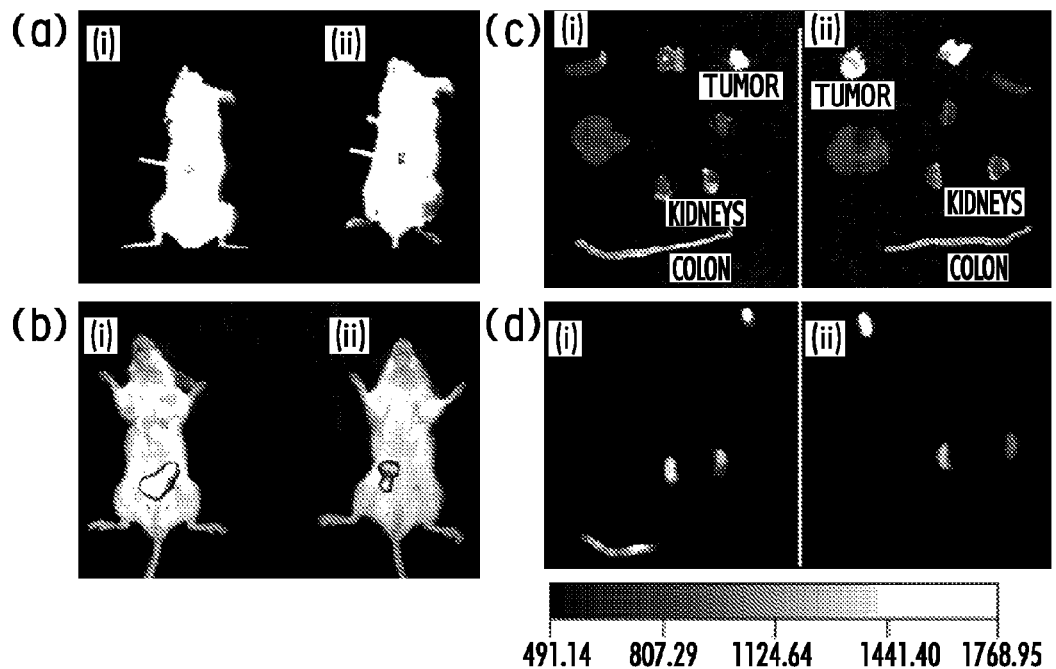
Figures 2, 14:
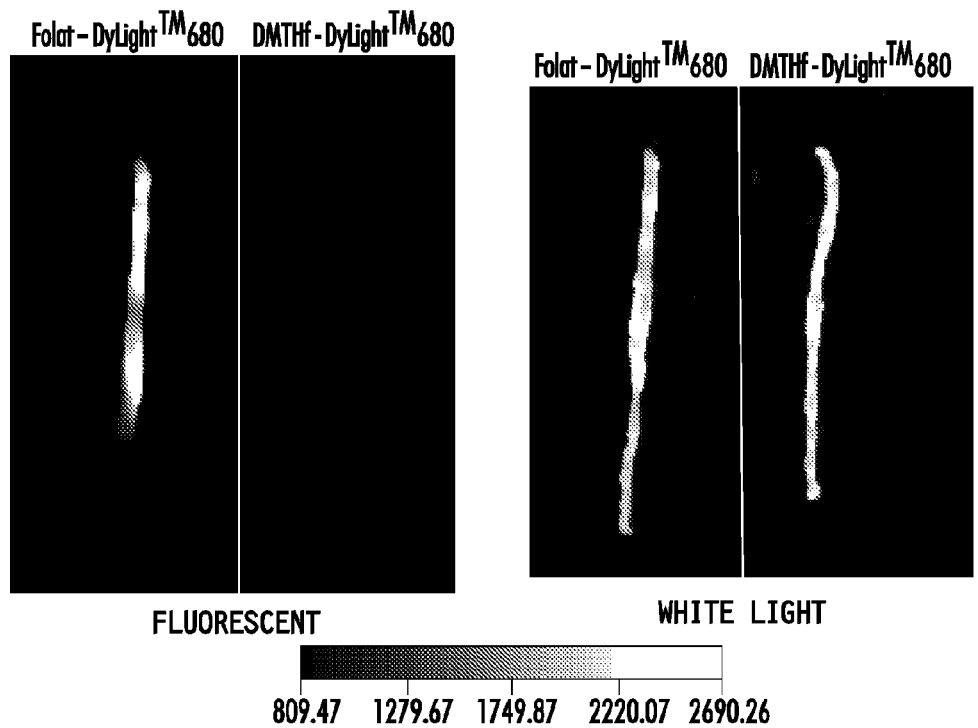

It has also been discovered that non-radioactive DMTHF- conjugates that employ near infrared (NIR) dyes as a non-invasive diagnostic tool can be used to selectively image cells or tissues expressing, over-expressing, or selectively expressing FR-α. Several novel DMTHF-NIR dye conjugates were prepared. Illustrative examples DMTHF-Dylight™ 680 (compound 4b) and DMTHF-Dylight 750 (compound 4d) demonstrate the selective affinity of the modified folate targeting ligand for FR-α. In an illustrative example, optical imaging was performed in athymic nude mice bearing a xenograft KB tumor (see FIG. 13) and Balb/C mice bearing M109 tumor along with DSS induced ulcerative colitis (see FIG. 14-1) showing tumor selective uptake of DMTHF-Dylight™ 680. Folate-Dylight™ 680 (compound 3b) was used as a positive control to show non-selectivity for FR-α and FR-β. As seen in the region of interest (ROI) analysis of various organs/tissues from the respective set of mice, in the presence of ulcerative colitis there was a significant uptake of folate-Dylight™ 680 in both tumor and colon (see FIG. 14-1d(i)) whereas the DMTHF-Dylight™ 680 was accumulated mainly in tumors (see FIG. 14-1d(ii)). The lack of observable fluorescent uptake in the inflamed colon provides additional evidence for the lower FR-β selectivity and high affinity for FR-α of DMTHF-NIR dye conjugates (see FIG. 14-2).

Illustrative conjugates containing tubulysin B hydrazide (a microtubule inhibitor) or desacetylvinblastine hydrazide (a vinca alkaloid) linked to DMTHF via a peptide spacer and releasable disulfide bond (see Scheme 3) were prepared. For example, DMTHF-EC-119-TubH (compound 6a) and DMTHF-EC-119-DAVBH (compound 6b) drug conjugates were synthesized by the reaction of DMTHF-EC-119 linker with activated tubulysin B hydrazide compound 5a and activated desacetylvinblastine hydrazide compound 5b, respectively, following the methods described below.

Figure 15:
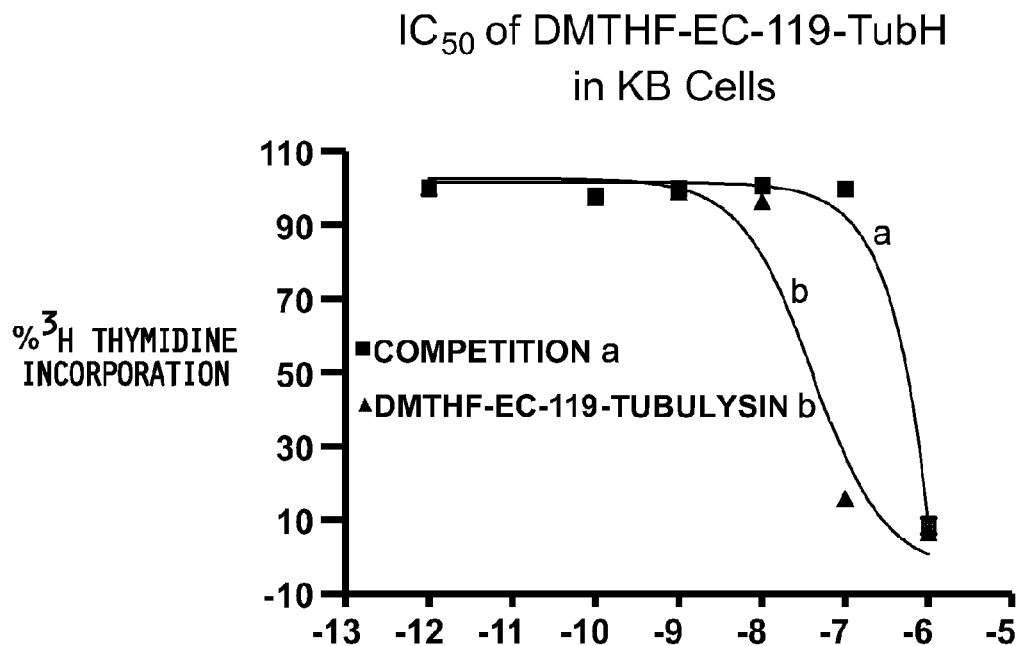
FIG. 15 Dose-dependent in vitro cytotoxicity study of DMTHF-EC-119-tubulysin B hydrazide ($IC_{50}$=41 nM) in KB-cells. Triangles indicate treatment with increasing concentrations of drug conjugate DMTHF-EC-119-tubulysin B hydrazide; Squares indicate treatment with increasing concentrations of drug conjugate DMTHF-EC-119-tubulysin B hydrazide of KB-cells pretreated with 100 μM folic acid for 1 h prior to addition of DMTHF-EC-119-tubulysin B hydrazide.

The in vitro toxicity of DMTHF-EC-119-TubH, compound 6a, (See FIG. 15) was analyzed in KB cells which were pulsed for 2 h with increasing concentrations of DMTHF-EC-119-TubH in the presence or absence of 100 μM folic acid. After washing to remove unbound conjugate, cells were incubated for an additional 66 h in fresh medium before addition of tritiated thymidine. Thymidine incorporation (a means of determining live cells) dramatically decreased with increasing concentrations of DMTHF-EC-119-TubH. The IC$_{50}$ value from the plot of % [$^3$H]-thymidine incorporation versus log concentration was found to be 41 nM. The cytotoxicity of DMTHF-EC-119-TubH was inhibited by excess folic acid. It is believed that this indicates that the observed cytotoxicity was folate receptor mediated.

Figure 16:
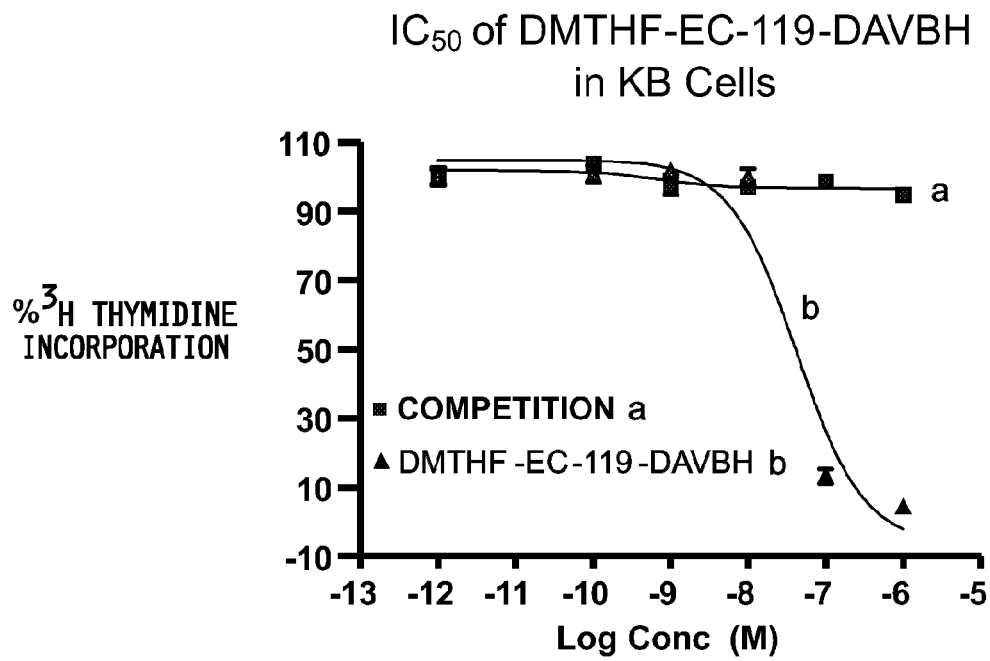
FIG. 16 Dose-dependent in vitro cytotoxicity study of DMTHF-EC-119-desacetylvinblastine hydrazide ($IC_{50}$=42 nM) in KB-cells. Triangles indicate treatment with an increasing concentration of drug conjugate DMTHF-EC-119-desacetylvinblastine hydrazide; squares indicate treatment with the DMTHF-drug conjugate of KB-cells pretreated with 100 μM folic acid for 1 h prior to addition of DMTHF-EC-119-desacetylvinblastine hydrazide.
Figure 17:
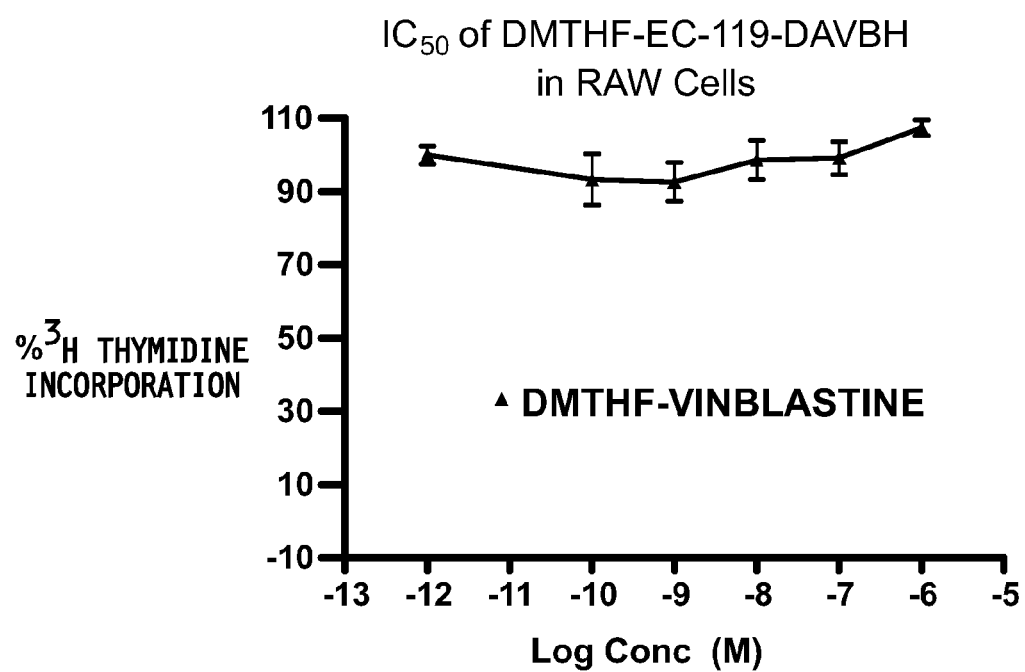
FIG. 17 Dose-dependent in vitro cytotoxicity study of DMTHF-EC-119-desacetylvinblastine hydrazide in RAW 264.7 cells (a murine macrophage cell line). Triangles indicate treatment with an increasing concentration of drug conjugate DMTHF-EC-119-desacetylvinblastine hydrazide.
Figure 20:
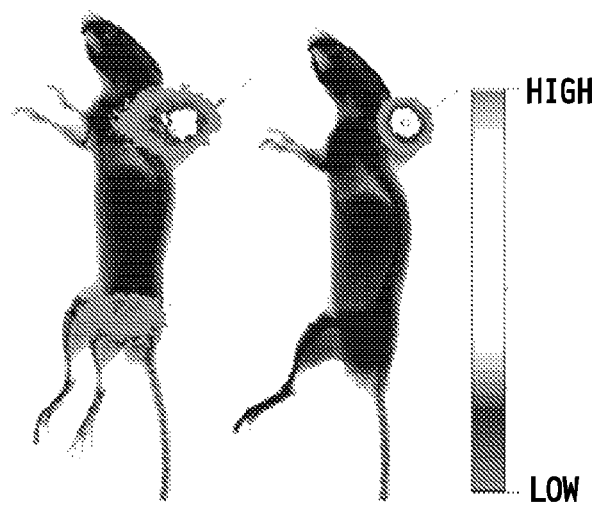
FIG. 20 Overlay of radioimages onto soft X-ray images of M109 tumor-bearing balb/c mice (indicated by arrows) induced with DSS to develop ulcerative colitis. Mice were injected intravenously with either EC 20-$^{99m}$Tc (left) or DMTHF-$^{99m}$Tc (right) 4 h prior to radioimaging. Kidneys were shielded in both cases to allow better visualization of the tumors and inflamed colon.
Figure 21A:
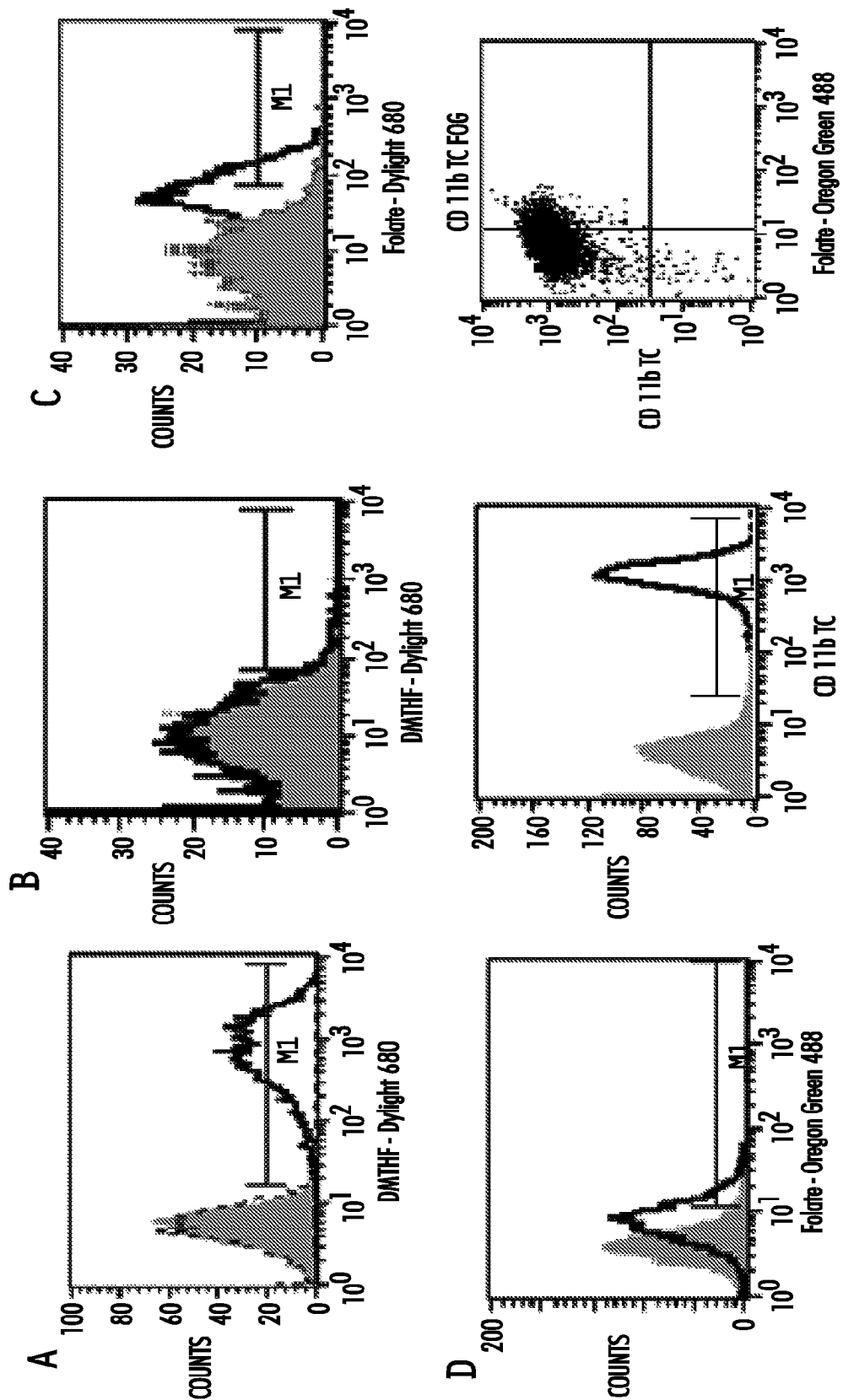
FIG. 21 Flow cytometry analysis of DMTHF-dye conjugate binding to human cancer cells, human monocytes, and activated rat peritoneal macrophages: (A) Binding of DMTHF-DyLight680 to FR-α positive KB cells; (B) Binding of DMTHF-DyLight680 to FR-β positive rat peritoneal macrophages that had been activated in vivo by intraperitoneal injection of thioglycollate; (C) Binding of folate-DyLight680 to FR-β positive rat peritoneal macrophages; (D & E) Binding of folate-Oregon Green (D) or DMTHF-Oregon Green (E) to FR-β positive CD11b positive human peripheral blood monocytes.
Figure 21B:
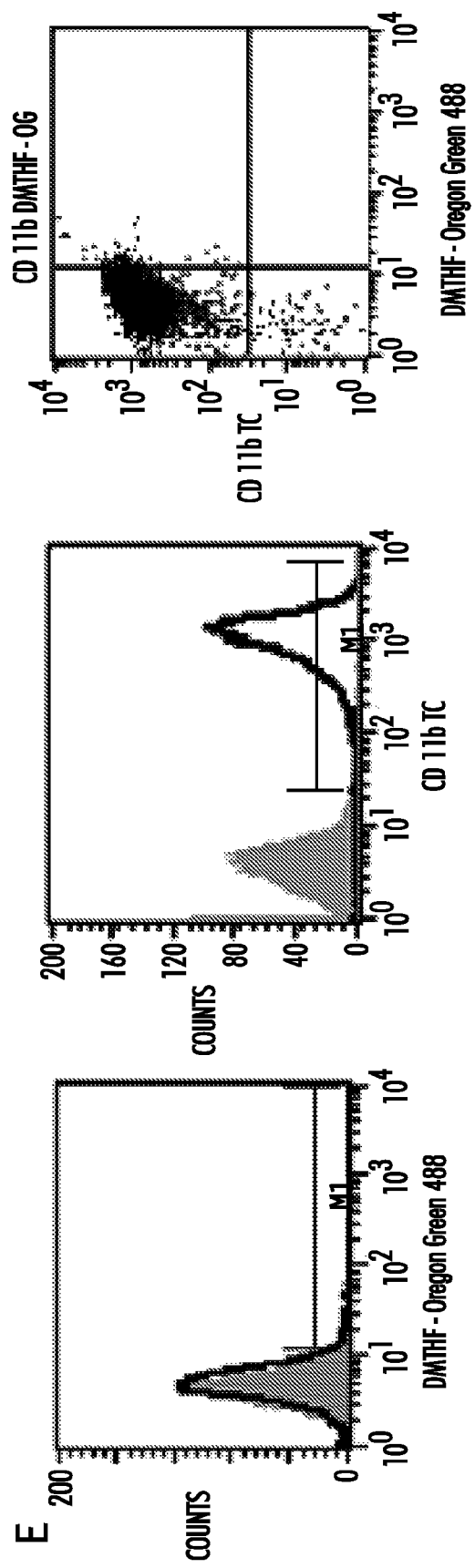

Replacing compound 6a with DMTHF-EC-119-DAVBH, compound 6b, in the cytotoxicity assay for KB cells described above gave similar results. The IC$_{50}$ value from the plot of % [$^3$H]-thymidine incorporation versus log concentration was found to be 42 nM (see FIG. 16). An analogous toxicity study of DMTHF-EC-119-DAVBH in RAW 264.7 cells, a murine macrophage cell line, did not show any cytotoxicity (See FIG. 17). The DMTHF drug conjugates of tubulysin B hydrazide and desacetylvinblastine hydrazide failed to show appreciable cytotoxicity in IGROV cells, a human ovarian cancer cell line (see FIGS. 18 and 19). It is believe that this may be attributed to the lower number of folate receptors (45.3 pmol per mg of protein) in the IGROV cell line compared to KB-cells. Selectivity of DMTHF towards FR-α$^+$ renders it an attractive new ligand for differential diagnosis of cancer from inflammation.

Scheme 3

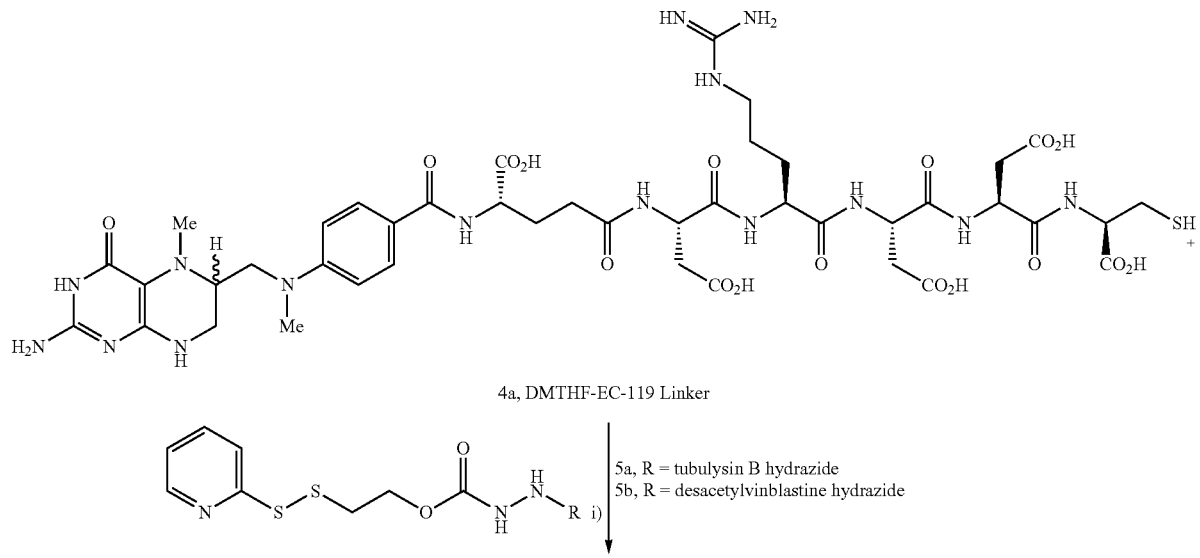

4a, DMTHF-EC-119 Linker

5a, R = tubulysin B hydrazide
5b, R = desacetylvinblastine hydrazide

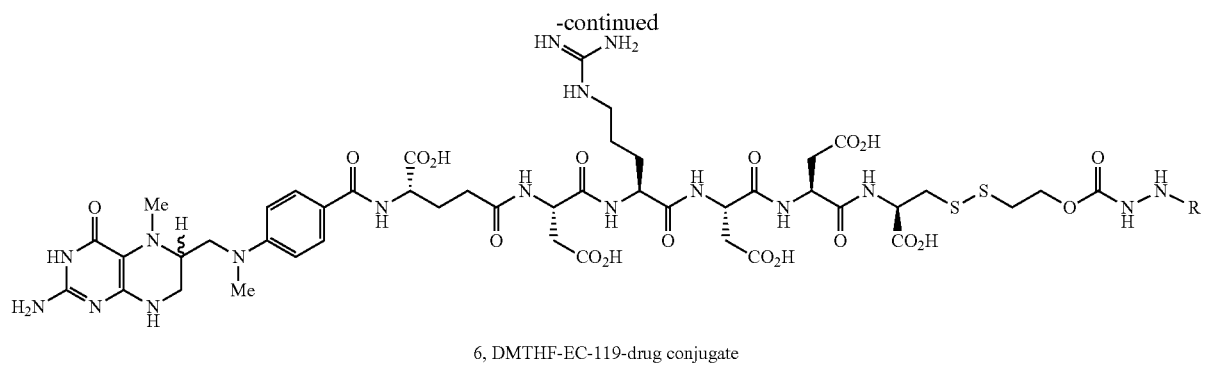

6, DMTHF-EC-119-drug conjugate

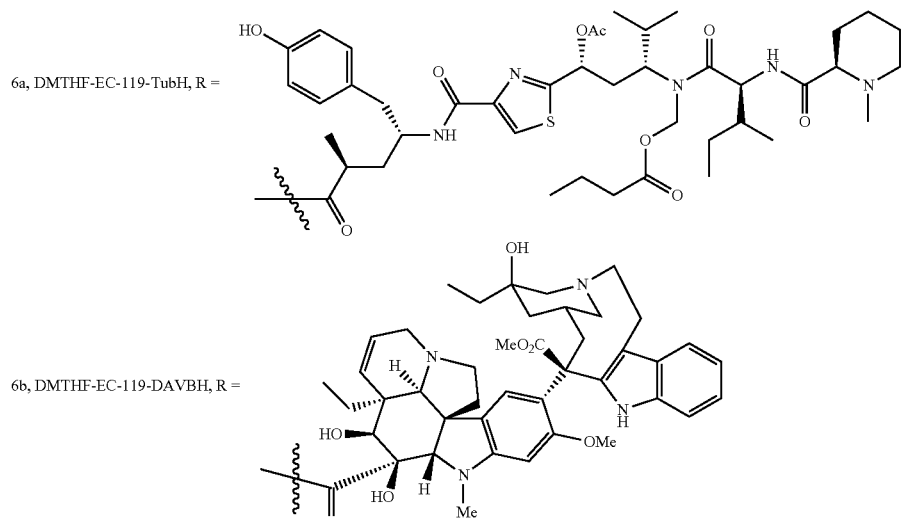

6a, DMTHF-EC-119-TubH, R =

6b, DMTHF-EC-119-DAVBH, R =

Reagent and conditions: i) (a) H₂O/THF (1:1), pH = 7.0 (adjusted using sat•NaHCO₃), argon purge, 45-min.

MATERIALS AND METHODS

CONJUGATE EXAMPLES

Unless otherwise specified, all chemicals were purchased from Sigma-Aldrich (St. Louis, Mo.). All chemicals and reagents for peptide synthesis were purchased from Novabiochem (La Jolla, Calif.). EC20 vials were a generous gift from Endocyte, Inc. Sodium pertechnetate was purchased from Cardinal Health (Indianapolis, Ind.). Dextran Sulphate Sodium (DSS) was obtained from MP Biochemicals (Akron, Ohio). Folate-deficient RPMI medium and phosphate buffered saline (PBS) were purchased from Invitrogen (Eugene, Oreg.). All final products were purified by reverse phase preparative HPLC (Waters, xTerra $C_{18}$ 10 μm; 19×250 mm). Purified compounds were analyzed by reverse phase analytical LC-MS (Waters, x-bridge $C_{18}$ 5 μm; 3.0×15 mm). NMR spetra were recorded using a Bruker 500 MHz cryoprobe (DMSO-$d_6$/$D_2O$), where presaturation was performed to reduce the intensity of the residual H2O peak. SPECT/CT imaging is recorded using MILab's (Utrecht, The Netherlands) ultrahigh resolution 3D U-SPECT-II instrument employing 75 pinholes technology, fully integrated with 3D X-ray CT scan of high resolution (80 μm and 160 μm pixel size).

Example

Synthesis, Purification and Characterization of $N^5,N^{10}$-Dimethyl Tetrahydrofolic Acid (DMTHF)-Chelate Conjugate For radioimaging purposes, the targeting ligand, $N^5,N^{10}$-dimethyl-tetrahydrofolic acid was linked to a chelating agent comprising the peptide sequence: β-L-diaminopropionic acid (β-DAP), L-aspartic acid (L-Asp), L-cysteine (L-Cys). EC20 (pteroic acid-Glu-DAP-Asp-Cys) was prepared and purified according to a reported procedure (Leamon, et al., 2002). Briefly, acid-sensitive Wang resin loaded with 0.106 mmol of fluorenylmethoxy carbonyl-trityl-L-cysteine (Fmoc-L-Cys(Trt)-OH) was reacted first with 0.265 mmol of HOBT and 0.265 mmol HBTU, followed by sequential addition of 0.265 mmol of the desired protected monomer. Fmoc protecting groups were removed after each coupling step under standard conditions (20% piperidine in dimethyl formamide), and the N10-trifluoroacetyl moiety on the pteroic acid was removed using 2% hydrazine in dimethyl formamide before cleaving the conjugate from the resin. Removal of the partially deprotected conjugate from the polymeric support was finally accomplished by treatment with 92.5% trifluoroacetic acid (TFA) containing 2.5% 1,2-ethanedithiol, 2.5% triisopropylsilane, and 2.5% deionized water. This reaction also resulted in simultaneous removal of all t-butyl (t-Bu), t-butoxycarbonyl (t-Boc) and trityl protecting groups.

The crude product was purified by preparative reverse-phase high-performance liquid chromatography (RP-HPLC) using a Waters, xTerra C18 10 μm; 19×250 mm column with a gradient mobile phase of A=0.1% trifluoroacetic acid and B=methanol; λ=285 nm; solvent gradient 1% B to 50% B in 30 minutes. The pure compound 1 was analyzed by LC-MS (ESI) mass spectrometry. Major positive ion peak (m/z, relative intensity): 745

Reduction of the pteridine nucleus to the dimethylated, tetrahydro-derivative was achieved by dissolving purified compound 1 (0.33 mmol) in 1 mL of 98% formic acid, followed by slow addition of borane-dimethylamine ($BH_3.NMe_2$) (16.5 mmol) at 0° C. over a period of 60 minutes. After the completion of addition, the reaction mixture was left to stand at 4° C. for 3-days and monitored by LC-MS. The crude product was purified as a mixture of diastereomers by preparative reverse-phase HPLC using a Waters, xTerra $C_{18}$ 10 μm; 19×250 mm column with a gradient mobile phase of A=10 mM ammonium acetate (pH 5.0) and B=methanol; λ=285 nm; solvent gradient 1% B to 50% B in 30 minutes. The pure compound 2 was analyzed by LC-MS (ESI) mass spectrometry. Major positive ion peak (m/z): $(M+H)^+$ 778. $^1H$ NMR ($D_2O$) δ 1.98 (m, 2H); 2.18 (m, 2H); 2.34 (m, 2H); 2.54 (m, 1H); 2.66 (m, 2H); 2.72 (m, 2H); 2.86 (s, 3H); 2.93 (s, 3H); 3.53 (m, 2H); 3.68 (m, 2H); 3.78 (m, 2H); 4.12 (dd, 2H); 4.32 (dd, 2H); 4.60 (dd, 2H); 6.73 (d, J=9.15 Hz, 2H); 7.63 (d, J=9.15 Hz, 2H). Yield=18-35%

Example

Synthesis, Purification and Characterization of $N^5,N^{10}$-Dimethyl Tetrahydrofolate-DyLight™ 680/DyLight 750 for Near Infrared Optical Imaging Synthesis of DMTHF-DyLight™ 680 and DMTHF-DyLight 750 are outlined in Scheme 2. The folate peptide linker 3 (0.33 mmol) (folate-γ-Asp-Arg-Asp-Asp-Cys-SH or EC-119) was synthesized as reported earlier, and dissolved in 1 mL of 98% formic acid, cooled to 0° C. on ice bath and treated with borane-dimethylamine complex (0.167 mmol) over a period of 60 minutes. The reaction mixture was left to stand in the refrigerator at 4° C. for 72 hours in the dark monitored by LC-MS. The crude product was then purified by preparative reverse-phase high-performance liquid chromatography (RP-HPLC) using a Waters, xTerra $C_{18}$ 10 μm; 19×250 mm column with a gradient mobile phase of A=10 mM ammonium acetate (pH 5.0) and B=methanol; λ=285 nm; solvent gradient 1% B to 50% B in 30 minutes. The pure compound was analyzed by LC-MS (ESI) mass spectrometry. Major positive ion peak (m/z, relative intensity): 1078. The purified product 4a was lyophilized and stored at 4° C. until use in preparation of dye conjugates.

1 mg DyLight™ 680 maleimide or 1 mg Dylight 750 maleimide (Thermo Scientific) was dissolved in anhydrous DMSO (100 μL) containing one equivalent of diisopropylethylamine, after which a threefold molar excess of 4a was added and the mixture stirred at room temperature overnight as outlined in Scheme 2. The crude products were purified by preparative RP-HPLC using a Waters, xTerra $C_{18}$ 10 μm;

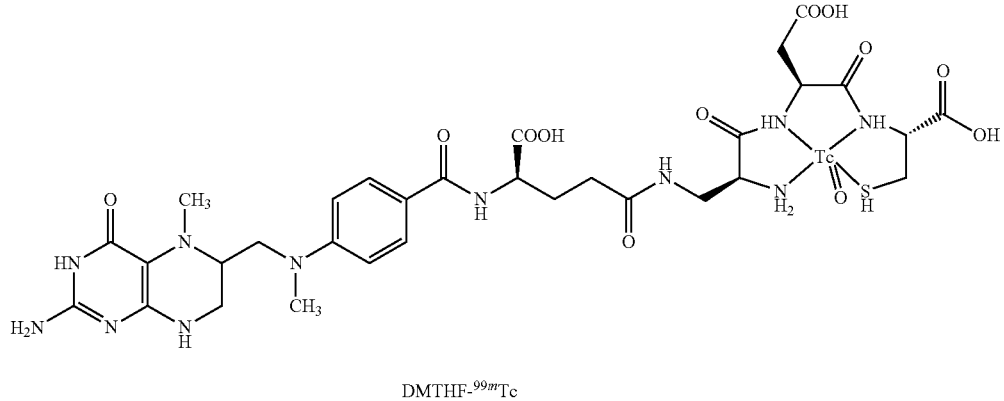

DMTHF-$^{99m}$Tc

Example

Formulation of $N^5,N^{10}$-Dimethyl Tetrahydrofolic Acid-$^{99m}$Tc Radiolabeling Kit An aqueous solution of 0.1 mg of DMTHF-chelate (1 mL), 80 mg sodium α-D-glucoheptonate, 80 μg tin (II) chloride dihydrate and sufficient 0.1 N sodium hydroxide to adjust the pH to 6.8±0.2, was lyophilized and sealed under argon atmosphere. Chelation of $^{99m}$Tc by the conjugate was achieved by injecting 1 mL of a solution of $^{99m}$Tc-labeled sodium pertechnetate (15mCi) into the vial and heating for ~18 min in a boiling water bath. The solution was allowed to cool to room temperature and stored in the dark until use on the same day. The final chelate complex is referred to as DMTHF-$^{99m}$Tc.

19×250 mm column with a gradient mobile phase of A=0.1% trifluoroacetic acid and B=methanol; λ=285 nm; solvent gradient 1% B to 50% B in 30 minutes. The dye conjugates 4b, 4d were analyzed by LC-MS (ESI) mass spectrometry. Major positive ion peak (m/z): 1005, the doubly charged molecular ion (4b); 1037, the doubly charged molecular ion (4d);

Example

Synthesis of $N^5,N^{10}$-Dimethyl Tetrahydrofolate-Oregon Green™ 488

$N^5,N^{10}$-Dimethyl tetrahydrofolate-Oregon Green™ 488 was synthesized for analysis of the ligand's affinity for FR-β expressing human peripheral blood monocytes, as outlined in Scheme 2. Briefly, 1 mg of Oregon Green™ 488 maleimide (Thermo Scientific) was dissolved in anhydrous DMSO (100 µL) containing one equivalent of diisopropyl ethylamine, and a threefold molar excess of 4a was added and stirred at room temperature overnight. The crude product was purified by preparative reverse-phase high-performance liquid chromatography (RP-HPLC) using a Waters, xTerra $C_{18}$ 10 µm; 19×250 mm column with a gradient mobile phase of A=0.1% trifluoroacetic acid and B=methanol; λ=285 nm; solvent gradient 1% B to 50% B in 30 minutes. The pure compound 4c obtained as a diastereomeric mixture was analyzed by LC-MS (ESI) mass spectrometry. Major positive ion peak (m/z): 771, the doubly charged molecular ion.

Example

Synthesis of DMTHF-EC-119-Tubulysin B Hydrazide (6a)

Argon was bubbled through a solution of saturated sodium bicarbonate (4 mL) and HPLC grade water (10 mL) for 45 min. With continuous bubbling of argon, DMTHF-EC-119 linker (10 mg, 0.0093 mmol) was dissolved in argon purged HPLC grade water (2.0 mL) and the pH of the reaction mixture was increased to approximately 7.0 by addition of argon purged bicarbonate. A solution of disulfide activated tubulysin B hydrazide 5a (9.8 mg, 0.0093 mmol) in THF (2.0 mL) was added to the reaction mixture, and the solution was stirred for 45 min and monitored by LC-MS. After removal of THF under reduced pressure, DMTHF-EC-119-tubulysin B hydrazide (DMTHF-EC-119-TubH) was purified by preparative RP-HPLC [A=10 mM ammonium acetate (pH=7.2), B=CH$_3$CN, solvent gradient: 5% B to 80% B in 30 min], yielding the desired product (10.3 mg, yield=55%). LRMS (LC/MS) (m/z): 1013.0 $(M+H)^{2+}$; UV/Vis: $\lambda_{max}$=280 nm.

Example

Synthesis of DMTHF-EC-119-Desacetylvinblastine Hydrazide (6b)

Following a similar procedure as described for preparation of (6a), DMTHF-EC-119-desacetylvinblastine hydrazide (6b) was synthesized from activated vinblastine hydrazide 5b. DMTHF-EC-119-desacetylvinblastine hydrazide (DMTHF-EC-119-DAVBH) was purified by preparative RP-HPLC [A=10 mM ammonium acetate (pH=7.2), B=CH$_3$CN, solvent gradient: 5% B to 80% B in 30 min], yielding the desired product (8.3 mg, yield=45%). LRMS (LC/MS) (m/z): 975.5 $(M+H)^{2+}$; UV/Vis: $\lambda_{max}$=280 nm.

METHOD EXAMPLES

Example

General Procedure for In Vitro Cytotoxicity Assay of DMTHF-EC-119 Drug Conjugates (6)

KB, RAW or IGROV cells were seeded in 24-well (100,000 cells/well) Falcon plates and allowed to form monolayers overnight. Spent medium was then replaced with fresh medium (0.5 mL) containing increasing concentrations of drug conjugate in the presence or absence of excess folic acid, and cells were incubated for an additional 2 h at 37° C. Cells were washed 3× with fresh medium (0.5 mL) and incubated in fresh medium (0.5 mL) for another 66 h at 37° C. Spent medium in each well was replaced with fresh medium (0.5 mL) containing [$^3$H]-thymidine (1 mCi/mL) and the cells were incubated for additional 4 h at 37° C. to allow [$^3$H]-thymidine incorporation. Cells were then rinsed with medium (3×0.5 mL) and treated with 5% trichloroacetic acid (0.5 mL) for 10 min at room temperature. After replacing trichloroacetic acid with 0.25 N NaOH (0.5 mL), cells were transferred to individual scintillation vials containing Ecolume scintillation cocktail (3.0 mL) and counted in a liquid scintillation counter. IC$_{50}$ values were calculated by plotting %[$^3$H]-thymidine incorporation versus log concentration of DMTHF-EC-119-drug conjugate in GraphPad Prism 4.

Example

Cell Culture and Animal Husbandry

KB and A549 cells were obtained from American Type Culture Collection. M109 cells were a kind gift from Alberto Gabizon. CHO-β cells were a kind gift from Endocyte Inc. The cell lines were grown continuously as a monolayer in folate-free RPMI medium containing 10% fetal calf serum and 1% penicillin/streptomycin antibiotic cocktail in a 5% $CO_2$: 95% air-humidified atmosphere at 37° C. M109 cells were regenerated as reported earlier.

All animal procedures were approved by the Purdue Animal Care and Use Committee in accordance with NIH guidelines. Normal rodent diets were not used, because they contain excessive amounts of folic acid that elevate serum folate levels significantly above normal physiological concentrations. All animals were maintained on a folate deficient diet (Harlan Teklad laboratories, WI) for at least 3 weeks prior to each study to lower their serum folate levels into the physiological range. Control animals were also maintained on a folate deficient diet.

Example

Binding Affinity and Specificity of DMTHF-$^{99m}$Tc Conjugate

KB or CHO-β cells (100,000 cells/well in 500 µl) were plated into 24 well Falcon plates and allowed to form adherent monolayers (ca. 70% confluent) overnight. Spent medium in each well was replaced with fresh medium (0.5 ml) containing increasing concentrations of EC20-$^{99m}$Tc or DMTHF-$^{99m}$Tc in the presence or absence of 100-fold molar excess of folic acid, and the cells were incubated for 1 hour at 37° C. Cells were washed with PBS (3×1.0 mL), after which 0.25 M aqueous NaOH (0.5 ml) was added to dissolve the cells. After 10 minutes incubation, 450 µl from each well were transferred polypropylene tubes and counted for radioactivity in a γ counter (Packard Instrument Company). The binding affinity, $K_d$, was calculated using GraphPad Prism 4 by plotting cell bound radioactivity versus the concentration of radiotracer added.

Example

Flow Cytometry Analysis of KB and Rat Peritoneal Macrophages

KB cells were allowed to form monolayers in a T75 falcon flask for 48 hours in folate-deficient RPMI 1640 culture medium (FDRPMI). The confluent cells were trypsinized and 1×10$^6$ cells were transferred into each Eppendorf tube and centrifuged. Spent medium was removed and the pelleted cells were resuspended in fresh medium containing either DMTHF-DyLight™ 680 conjugate (100 nM) or folate-DyLight™ 680 conjugate (100 nM), either in the presence or absence of 100-fold molar excess of free folic acid. After incubation for 1 h at 37° C., the cells were washed 3 times with PBS (0.5 ml) and re-suspended in fresh PBS (0.4 ml). Bound fluorescence was analyzed using a flow cytometer (Cytomics F500; Beckman Coulter).

For similar analysis of rat peritoneal macrophages, experimental adjuvant-induced arthritis was induced in Lewis rats according to a previously reported procedure. After 25 days of arthritis induction, the rats were sacrificed by $CO_2$ asphyxiation and peritoneal macrophages were harvested by injecting 60 mL PBS into the peritoneal cavity, and after brief massage of the abdomen, removing the cells using the injection syringe. Peritoneal cells were transferred to Eppendorf tubes, washed and stained as described above, except CD11b+ macrophages that were identified by co-staining with anti-CD 11b-PE (phycoerythrin-labeled antibody to CD11b).

Example

Flow Cytometry Analysis of Human Peripheral Blood Monocytes

Human peripheral blood monocytes were isolated from whole human blood by a known procedures. Briefly, whole human blood in anticoagulant was collected from healthy volunteers following informed consent and the mononuclear cells were separated by Ficoll-Paque centrifugation. Cells were re-suspended in Eppendorf tubes in FDRPMI medium containing either DMTHF-Oregon Green™ 488 (100 nM) or folate-Oregon Green™ 488 (100 nM) plus CD 11b Tricolor to label human monocytes. For competition studies 100-fold molar excess of free folic acid was included in the suspension. After incubation for 1 h at 37° C., the cells were washed 3 times with PBS (0.5 ml) and re-suspended in fresh PBS (0.4 ml). Bound fluorescence was analyzed by flow cytometry as described above.

Example

Optical and Radioimaging of Animal Models of Cancer and Inflammatory Diseases

Radioimages of murine models of human diseases were acquired with a Kodak Imaging Station coupled to a CCD camera operated with Kodak Molecular Imaging Software v 4.0 (Carestream Molecular Imaging). Abdomens were generally shielded with a lead plate in order to mask radioactivity emitted from the kidneys and bladder. The parameters used for radioimaging were: acquisition time=2 min, f-stop=4, focal plane=7, FOV=200, binning=4. For white light imaging, the parameters were: acquisition time=0.05 s, f-stop=11, focal plane=7, FOV=200, with no binning. For fluorescent imaging, abdomens were shielded with black construction paper to block fluorescence emitted from the kidneys and bladder. The parameters used were: acquisition time=30 s, excitation filter of $\lambda$=625 nm, emission filter of $\lambda$=700 nm, f-stop=4, focal plane=7, FOV=200, and binning=4.

Example

Biodistribution of Radioimaging Agents

Following the above radioimaging studies, animals were dissected and selected organs/tissues were collected into pre-weighed γ-counter tubes. Radioactivity of weighed tissues and test compounds were counted in a γ-counter. CPM values were decay corrected and results were calculated as % injected dose per gram of wet tissue (% ID/g).

Example

Analysis of Tumor-Bearing Mice

Six-week-old female nu/nu mice (Harlan Laboratories, IN) were inoculated subcutaneously on their shoulders with KB or A549 cells ($1.0 \times 10^6$ cells/mouse in RPMI medium) using a 25-gauge needle. Growth of the tumors was measured in two perpendicular directions every 2 days using a caliper, and the volumes of the tumors were calculated as $0.5 \times L \times W^2$ (L=measurement of longest axis, and W=measurement of axis perpendicular to L in millimeters). Radiotracer biodistribution studies were performed 12 to 15 days after tumor cell implantation, when the tumors reached approximately 50 $mm^3$ in volume. The mice were randomly assigned to different treatment groups and injected intraperitoneally with DMTHF-$^{99m}$Tc (50 nmol, 150 μCi in 100 μl of PBS). Four hours post injection, animals were sacrificed by $CO_2$ asphyxiation, and imaging and biodistribution studies were performed as described above.

Example

Analysis of Atherosclerotic Mice

B6.129-ApoE$^{tm1/Unc}$/J mice (apoE−/−) breeding trios were purchased from the Jackson Laboratory and maintained in a temperature and humidity controlled environment with a 12 h dark-light cycle. Female mice were weaned at 3 weeks of age and maintained on either normal rodent chow or transferred at five weeks of age to a western diet consisting of 2% cholesterol and 21.2% fat (TD.88137, Harlan-Teklad, Wis.) to accelerate the induction of atherosclerosis. After 16 weeks on high fat diet, the mice were randomly assigned to different treatment groups and treated (ip) with EC20-$^{99m}$Tc or DMTHF-$^{99m}$Tc (50 nmol, 150 μCi in 100 μl of PBS). Four hours post injection, animals were sacrificed by $CO_2$ asphyxiation, and imaging and biodistribution studies were performed as described earlier.

Example

Analysis of Collagen-Induced Arthritic Mice

Seven week old male DBA/1 LacJ mice were purchased from Harlan Laboratories and maintained on a folate deficient diet (Harlan-Teklad, Wis.). Collagen-induced arthritis (CIA) was initiated as described elsewhere. Arthritis scores were recorded by following the weighted criterion established by Chondrex, Inc. W.A. When the mice attained an arthritis score of 7, they were randomly assigned to different treatment groups and injected with EC20-$^{99m}$Tc or DMTHF-$^{99m}$Tc (50 nmol, 150 μCi in 100 μl of PBS). Four hours post injection, animals were sacrificed by $CO_2$ asphyxiation, and imaging and biodistribution studies were performed as described earlier.

Example

Analysis of Muscle Injury Model in Mice

Six week old male C57BL6J mice were purchased from Harlan Laboratories and maintained on a folate deficient diet (Harlan-Teklad, Wis.) for at least 3 weeks prior to analysis. Muscle injury was caused by injection of cardiotoxin from Naja atra, as reported elsewhere. Briefly, mice were anesthetized with 3% isoflurane and the right tibialis anterior (TA) muscle of each mouse was injected with 100 µl cardiotoxin I (10 µM, Sigma-Aldrich). Three days post injection, the mice were randomly assigned to different treatment groups and injected (i.p) with EC20-$^{99m}$Tc or DMTHF-$^{99m}$Tc as described above.

Example

Analysis of Tumor-Bearing Mice with Induced Ulcerative Colitis

Six week old female Balb/c mice were purchased from Harlan laboratories and maintained on a folate deficient diet (Harlan-Teklad, Wis.). After one week of acclimation, the mice were inoculated subcutaneously on the shoulder with 0.1 mL of M109 tumor cell suspension (1×10$^6$ cells). Subcutaneous tumor growth was monitored daily and on day 10 post tumor inoculation, 4% dextran sulfate sodium was added to their drinking water for 6 days to induce experimental ulcerative colitis. After colitis induction, the animals were randomly divided into different treatment groups and injected with EC20-$^{99m}$Tc or DMTHF-$^{99m}$Tc as described above.

Example

Preparation of Animals for Optical Imaging

Animals bearing tumors and/or inflammatory diseases were prepared as described above and injected intraperitoneally with DMTHF-DyLight™ 680 or folate-DyLight™ 680 conjugate (4 nmol in 100 µl of PBS). Four hours post injection, animals were sacrificed by CO$_2$ asphyxiation and images were acquired with a Kodak Imaging Station using the same parameters described earlier. To evaluate accumulation of test compounds in specific organs/tissues, animals were dissected and organs/tissues of interest were excised and selected regions of interest were analyzed in the Kodak Imaging Station.

What is claimed is:

1. A folate receptor alpha selective binding ligand drug conjugate of the formula

B-L-D or a pharmaceutically acceptable salt thereof, wherein
B is a folate receptor alpha selective binding ligand having the formula wherein * indicates the point of attachment to the linker;
X and Y are each independently selected from the group consisting of halo, $R^2$, $OR^2$, $SR^3$, and $NR^4R^5$;
U, V, and W represent divalent moieties each independently selected from —$(R^{6a})C(R^{7a})$— and —$N(R^{4a})$—; Q is CH; T is selected from the group consisting of S, O, $NR^{4b}$, and —HC=CH—;

$A^1$ and $A^2$ are each independently selected from the group consisting of oxygen, sulfur, —C(Z)—, —C(Z)O—, —OC(Z)—, —$N(R^{4b})$—, —$C(Z)N(R^{4b})$—, —$N(R^{4b})C(Z)$—, —$OC(Z)N(R^{4b})$—, —$N(R^{4b})C(Z)O$—, —$N(R^{4b})C(Z)N(R^{5b})$—, —S(O)—, —S(O)$_2$—, —$N(R^{4b})S(O)_2$—, —$C(R^{6b})(R^{7b})$—, —N(C≡CH)—, —N(CH$_2$C≡CH)—, C$_1$-C$_{12}$ alkylene, and C$_1$-C$_{12}$ alkyeneoxy, where Z is oxygen or sulfur;
$A^3$ is an amino acid; q is an integer from 0 to 3;
$R^1$ is selected from the group consisting of hydrogen, halo, C$_1$-C$_{12}$ alkyl, and C$_1$-C$_{12}$ alkoxy;
$R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, C$_1$-C$_{12}$ alkyl, C$_1$-C$_{12}$ alkoxy, C$_1$-C$_{12}$ alkanoyl, C$_1$-C$_{12}$ alkenyl, C$_1$-C$_{12}$ alkynyl, (C$_1$-C$_{12}$ alkoxy)carbonyl, and (C$_1$-C$_{12}$ alkylamino)carbonyl;
$R^6$ and $R^7$ are each independently selected from the group consisting of hydrogen, halo, C$_1$-C$_{12}$ alkyl, and C$_1$-C$_{12}$ alkoxy; or, $R^6$ and $R^7$ are taken together to form a carbonyl group; $R^{6a}$ and $R^{7a}$ are each independently selected from the group consisting of hydrogen, halo, C$_1$-C$_{12}$ alkyl, and C$_1$-C$_{12}$ alkoxy; or $R^{6a}$ and $R^{7a}$ are taken together to form a carbonyl group; and
p, r, s and t are each independently either 0 or 1;
L is a linker or is absent; and
D represents one or more drugs each independently selected from the group consisting of a therapeutic agent and an imaging agent.

2. The conjugate of claim 1 wherein the drug is a therapeutic agent.

3. The conjugate of claim 1 wherein the drug is an imaging agent.

4. The conjugate of claim 1 wherein X is OH and Y is NH$_2$.

5. The conjugate of claim 1 wherein W and U are —$N(R^{4a})$—; Q is CH; V is CH$_2$; $A^1$ is —$N(R^{4b})$—; s is 1; p is 1; and t is 0.

6. The conjugate of claim 5 wherein $R^{4a}$ and $R^{4b}$ are methyl.

7. The conjugate of claim 1 wherein the linker includes a releasable linker.

8. The conjugate of claim 1 wherein the linker does not include a releasable linker.

9. The conjugate of claim 1 wherein the drug is an imaging agent.

10. The conjugate of claim 9 wherein the imaging agent is a positron-emitting radioisotope attached to the linker selected from group consisting of $^{34}$Cl, $^{45}$Ti, $^{51}$Mn, $^{61}$Cu, $^{63}$Zn, $^{68}$Ga, $^{11}$C, $^{13}$N, $^{15}$O, and $^{18}$F.

11. The conjugate of claim 9 wherein the imaging agent is a radioactive isotope of a metal coordinated to a chelating group, where the radioactive metal isotope is selected from the group consisting of technetium, rhenium, gallium, gadolinium, indium, and copper.

12. The conjugate of claim 11 wherein the chelating group has the formula wherein * indicates the site of attachment to the linker L.

13. The conjugate of claim 9 wherein the imaging agent is a fluorescent dye.

14. The conjugate claim 1 wherein the drug is a therapeutic agent.

15. The conjugate of claim 14 wherein the therapeutic agent is a vinca alkaloid or a tubulysin.

16. A pharmaceutical composition comprising an imaging effective or therapeutically effective amount of one or more conjugates of claim 1.

17. A method for imaging cancer cells in a patient, the method comprising the steps of
administering to the patient an imaging effective amount of the conjugate of claim 1, wherein D is an imaging agent and
imaging the cancer cells.

18. A folate receptor alpha selective binding ligand drug conjugate of the formula

B-L-D or a pharmaceutically acceptable salt thereof, wherein
B is a folate receptor alpha selective binding ligand having the formula

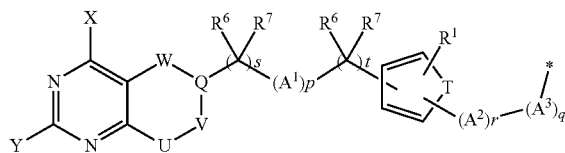

wherein * indicates the point of attachment to the linker;
X and Y are each independently selected from the group consisting of halo, $R^2$, $OR^2$, $SR^3$, and $NR^4R^5$;
U, V, and W represent divalent moieties each independently selected from —$(R^{6a})C(R^{7a})$— and —$N(R^{4a})$—; Q is CH; T is selected from the group consisting of S, O, $NR^{4b}$, and —HC=CH—;
$A^1$ and $A^2$ are each independently selected from the group consisting of oxygen, sulfur, —C(Z)—, —C(Z)O—, —OC(Z)—, —$N(R^{4b})$—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4b}$)S(O)$_2$—, —C($R^{6b}$)($R^{7b}$)—, —N(C≡CH)—, —N(CH$_2$C≡CH)—, $C_1$-$C_{12}$ alkylene, and $C_1$-$C_{12}$ alkyeneoxy, where Z is oxygen or sulfur;
$A^3$ is an amino acid; q is an integer from 0 to 3;
$R^1$ is selected from the group consisting of hydrogen, halo, $C_1$-$C_{12}$ alkyl, and $C_1$-$C_{12}$ alkoxy;
$R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;
$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group; $R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group; and
p, r, s and t are each independently either 0 or 1;
L is a linker that includes a peptide having from 2 to about 20 amino acids, or L is absent; and
D is a chelating group of the formula

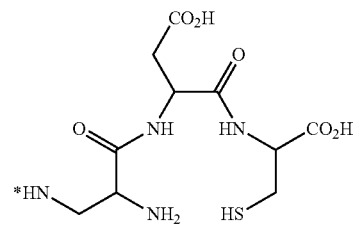

wherein * indicates the site of attachment to the linker L, wherein
a radioactive isotope selected from the group consisting of technetium, rhenium, gallium, gadolinium, indium, and copper is coordinated to the chelating group.

19. A folate receptor alpha selective binding ligand drug conjugate of the formula

B-L-D or a pharmaceutically acceptable salt thereof, wherein
B is a folate receptor alpha selective binding ligand having the formula

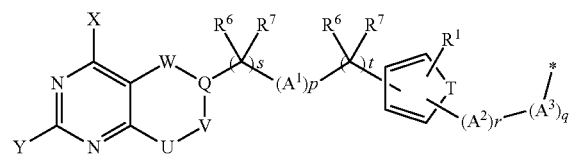

wherein * indicates the point of attachment to the linker;
X and Y are each independently selected from the group consisting of halo, $R^2$, $OR^2$, $SR^3$, and $NR^4R^5$;
U, V, and W represent divalent moieties each independently selected from —$(R^{6a})C(R^{7a})$— and —$N(R^{4a})$—; Q is CH; T is selected from the group consisting of S, O, $NR^{4b}$, and —HC=CH—;
$A^1$ and $A^2$ are each independently selected from the group consisting of oxygen, sulfur, —C(Z)—, —C(Z)O—, —OC(Z)—, —$N(R^{4b})$—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4b}$)S(O)$_2$—, —C($R^{6b}$)($R^{7b}$)—, —N(C≡CH)—, —N(CH$_2$C≡CH)—, $C_1$-$C_{12}$ alkylene, and $C_1$-$C_{12}$ alkyeneoxy, where Z is oxygen or sulfur;
$A^3$ is an amino acid; q is an integer from 0 to 3;
$R^1$ selected from the group consisting of hydrogen, halo, $C_1$-$C_{12}$ alkyl, and $C_1$-$C_{12}$ alkoxy;
$R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;
$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group; $R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group; and
p, r, s and t are each independently either 0 or 1;
L is a linker that includes a peptide having from 2 to about 20 amino acids and a releasable linker; and
D is a vinca alkaloid or a tubulysin.

20. The conjugate of claim 1 wherein B is dimethyltetrahydrofolate.

* * * * *